United States Patent
O'Neill et al.

(10) Patent No.: US 11,840,543 B2
(45) Date of Patent: Dec. 12, 2023

(54) COMPOUNDS AND USES

(71) Applicants: The University of Queensland, Queensland (AU); THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH NEAR DUBLIN, Dublin (IE)

(72) Inventors: Luke O'Neill, Dublin (IE); Rebecca Coll, West End (AU); Matthew Cooper, Chapel Hill (AU); Avril Robertson, Kenmore (AU); Kate Schroder, Fairfield (AU); Angus Murray MacLeod, Cambridge (GB); David John Miller, Cambridge (GB)

(73) Assignees: THE UNIVERSITY OF QUEENSLAND, Queensland (AU); THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH NEAR DUBLIN, Dublin (IE)

( * ) Notice: Subject to any disclaimer, the term of this patent is extended or adjusted under 35 U.S.C. 154(b) by 40 days.

(21) Appl. No.: 16/614,776

(22) PCT Filed: May 24, 2017

(86) PCT No.: PCT/IB2017/053059
§ 371 (c)(1),
(2) Date: Nov. 18, 2019

(87) PCT Pub. No.: WO2018/215818
PCT Pub. Date: Nov. 29, 2018

(65) Prior Publication Data
US 2020/0207780 A1 Jul. 2, 2020

(51) Int. Cl.
| | |
|---|---|
| C07C 311/60 | (2006.01) |
| C07D 495/04 | (2006.01) |
| C07D 207/38 | (2006.01) |
| C07D 217/24 | (2006.01) |
| C07D 241/24 | (2006.01) |
| C07D 249/04 | (2006.01) |
| C07D 261/18 | (2006.01) |
| C07D 271/12 | (2006.01) |
| C07D 307/68 | (2006.01) |
| C07D 413/12 | (2006.01) |

(52) U.S. Cl.
CPC .......... *C07D 495/04* (2013.01); *C07C 311/60* (2013.01); *C07D 207/38* (2013.01); *C07D 217/24* (2013.01); *C07D 241/24* (2013.01); *C07D 249/04* (2013.01); *C07D 261/18* (2013.01); *C07D 271/12* (2013.01); *C07D 307/68* (2013.01); *C07D 413/12* (2013.01)

(58) Field of Classification Search
None
See application file for complete search history.

(56) References Cited

U.S. PATENT DOCUMENTS

| | | | |
|---|---|---|---|
| 3,426,067 | A | 2/1969 | Weber et al. |
| 3,507,961 | A | 4/1970 | Weber et al. |
| 3,546,234 | A | 12/1970 | Fauland et al. |
| 3,917,690 | A | 11/1975 | Weber et al. |
| 4,678,498 | A | 7/1987 | Artz |

(Continued)

FOREIGN PATENT DOCUMENTS

| | | |
|---|---|---|
| CH | 484144 A | 1/1970 |
| CH | 490350 A | 5/1970 |

(Continued)

OTHER PUBLICATIONS

Database Registry Chemical Abstracts Service, Columbus, Ohio, Accession No. RN 1995069-60-7; 1995068-26-2, Entered STN: Sep. 16, 2016.*
Database Registry Chemical Abstracts Service, Columbus, Ohio, Accession No. RN 1995068-63-7, Entered STN: Sep. 16, 2016.*
Alsante et al., "Pharmaceutical Impurity Identification: a Case Study Using a Multidisciplinary Approach" Journal of Pharmaceutical Sciences, 93(9):2296-2309, (2004).
Ardecky et al., "Identification of a selective inhibitor of murine intestinal alkaline phosphatase (ML260) by concurrent ultra-high throughput screening against human and mouse isozymes," Bioorganic and Medicinal Chemistry Letters, 24(3):1000-1004, (2014).

(Continued)

*Primary Examiner* — Samantha L Shterengarts
(74) *Attorney, Agent, or Firm* — Alston & Bird LLP

(57) ABSTRACT

The present invention relates to compounds of formula (I): wherein Q is O or S; $R^1$ is a cyclic group substituted with at least one group X, wherein $R^1$ may optionally be further substituted; X is any group comprising a carbonyl group; and $R^2$ is a cyclic group substituted at the α-position, wherein $R^2$ may optionally be further substituted. The present invention further relates to salts, solvates and prodrugs of such compounds, to pharmaceutical compositions comprising such compounds, and to the use of such compounds in the treatment and prevention of medical disorders and diseases, most especially by the dual action of $NLRP_3$ inhibition and the stimulation of insulin secretion.

(I)

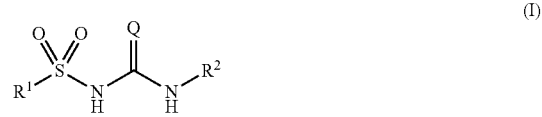

9 Claims, 1 Drawing Sheet

(56) References Cited

U.S. PATENT DOCUMENTS

| | | |
|---|---|---|
| 4,723,991 A | 2/1988 | Holyoke, Jr. et al. |
| 4,741,760 A | 5/1988 | Meyer et al. |
| 4,786,314 A | 11/1988 | Artz |
| 4,795,486 A | 1/1989 | Bohner et al. |
| 4,802,908 A | 2/1989 | Hillemann |
| 4,889,550 A | 12/1989 | Artz |
| 5,411,980 A | 5/1995 | Ashton et al. |
| 5,484,760 A | 1/1996 | Bussler et al. |
| 6,316,388 B1 | 11/2001 | Schutze et al. |
| 10,538,487 B2 | 1/2020 | O'Neill et al. |
| 11,130,731 B2 | 9/2021 | O'Neill et al. |
| 2002/0034764 A1 | 3/2002 | Gabel et al. |
| 2004/0092529 A1 | 5/2004 | Blumberg et al. |
| 2018/0044287 A1 | 2/2018 | O'Neill et al. |
| 2022/0112159 A1 | 4/2022 | O'Neill et al. |

FOREIGN PATENT DOCUMENTS

| | | |
|---|---|---|
| CN | 105906535 A | 8/2016 |
| DE | 1012598 B | 7/1957 |
| DE | 1518874 A1 | 5/1970 |
| DK | 2006 00313 L | 3/2006 |
| EP | 0125864 A1 | 11/1984 |
| EP | 0176304 A1 | 4/1986 |
| EP | 0177163 A2 | 4/1986 |
| EP | 0189069 A2 | 7/1986 |
| EP | 0204513 A2 | 12/1986 |
| EP | 0224842 A2 | 6/1987 |
| EP | 0249938 A2 | 12/1987 |
| EP | 0262096 A1 | 3/1988 |
| EP | 0318602 A1 | 6/1989 |
| EP | 0795548 A1 | 9/1997 |
| EP | 0885890 A1 | 12/1998 |
| EP | 1142586 A1 | 10/2001 |
| EP | 1174151 A1 | 1/2002 |
| EP | 1192949 A1 | 4/2002 |
| EP | 1192950 A1 | 4/2002 |
| EP | 2543670 A1 | 1/2013 |
| EP | 2781216 A1 | 9/2014 |
| EP | 2962692 A1 | 1/2016 |
| EP | 0987552 A2 | 3/2021 |
| FR | 2068472 A1 | 8/1971 |
| GB | 797474 A | 7/1958 |
| GB | 968805 A | 9/1964 |
| GB | 1147403 A | 4/1969 |
| GB | 1155936 A | 6/1969 |
| GB | 1182694 | 3/1970 |
| GB | 1203125 | 8/1970 |
| GB | 1322980 A | 7/1973 |
| GB | 2110689 A | 6/1983 |
| JP | 60-045573 A | 3/1985 |
| JP | 62-148482 A | 7/1987 |
| JP | S 62195376 A | 8/1987 |
| JP | 2000053649 A | 2/2000 |
| WO | WO 1991/010668 A1 | 7/1991 |
| WO | WO 1992/004319 A1 | 3/1992 |
| WO | WO 1998/032733 A1 | 7/1998 |
| WO | WO 2000/010982 A1 | 3/2000 |
| WO | WO 2001/019390 A1 | 3/2001 |
| WO | WO 2002/006246 A1 | 1/2002 |
| WO | WO 2003/035627 A1 | 5/2003 |
| WO | WO 2003/045400 A1 | 6/2003 |
| WO | WO 2003/086563 A2 | 10/2003 |
| WO | WO 2004/039376 A1 | 5/2004 |
| WO | WO 2006/085815 A1 | 8/2006 |
| WO | WO 2016/131098 A1 | 8/2016 |
| WO | WO 2017/129897 A1 | 8/2017 |
| WO | WO 2017/140778 A1 | 8/2017 |
| WO | WO 2017/184623 A1 | 10/2017 |
| WO | WO 2017/184624 A1 | 10/2017 |
| WO | WO 2017/201152 A1 | 11/2017 |
| WO | WO 2018/015445 A1 | 1/2018 |
| WO | WO 2018/136890 A1 | 7/2018 |
| WO | WO 2018/215818 A1 | 11/2018 |
| WO | WO 2019/008025 A1 | 1/2019 |
| WO | WO 2019/008029 A1 | 1/2019 |
| WO | WO 2019/034686 A1 | 2/2019 |
| WO | WO 2019/034688 A1 | 2/2019 |
| WO | WO 2019/034690 A1 | 2/2019 |
| WO | WO 2019/034692 A1 | 2/2019 |
| WO | WO 2019/034693 A1 | 2/2019 |
| WO | WO 2019/034696 A1 | 2/2019 |
| WO | WO 2019/034697 A1 | 2/2019 |
| WO | WO 2019/068772 A1 | 4/2019 |
| WO | WO 2019/092170 A1 | 5/2019 |
| WO | WO 2019/092171 A1 | 5/2019 |
| WO | WO 2019/092172 A1 | 5/2019 |
| WO | WO 2019/166619 A1 | 9/2019 |
| WO | WO 2019/166621 A1 | 9/2019 |
| WO | WO 2019/166623 A1 | 9/2019 |
| WO | WO 2019/166624 A1 | 9/2019 |
| WO | WO 2019/166627 A1 | 9/2019 |
| WO | WO 2019/166628 A1 | 9/2019 |
| WO | WO 2019/166629 A1 | 9/2019 |
| WO | WO 2019/166632 A1 | 9/2019 |
| WO | WO 2019/166633 A1 | 9/2019 |
| WO | WO 2019/206871 A1 | 10/2019 |
| WO | WO 2019/211463 A1 | 11/2019 |
| WO | WO 2020/035464 A1 | 2/2020 |
| WO | WO 2020/035465 A1 | 2/2020 |
| WO | WO 2020/035466 A1 | 2/2020 |
| WO | WO 2020/079207 A1 | 4/2020 |
| WO | WO 2020/104657 A1 | 5/2020 |
| WO | WO 2020/208249 A1 | 10/2020 |
| WO | WO 2021/032588 A1 | 2/2021 |
| WO | WO 2021/032591 A1 | 2/2021 |
| WO | WO 2021/043966 A1 | 3/2021 |
| WO | WO 2021/165245 A1 | 8/2021 |

OTHER PUBLICATIONS

Baldwin et al., "Inhibiting the Inflammasome: a Chemical Perspective," J. Med. Chem., 59(5), 1691-1710, (2016).
CAS : Registry No. 344752-79-0, Jul. 6, 2001.
CAS : Registry No. 345942-69-0, Jul. 15, 2001.
CAS : Registry No. 345944-26-5, Jul. 15, 2001.
CAS : Registry No. 345944-27-6, Jul. 15, 2001.
CAS : Registry No. 345944-28-7, Jul. 15, 2001.
CAS : Registry No. 907958-32-1, Sep. 20, 2006.
CAS : Registry No. 959357-50-7, Dec. 21, 2007.
CAS : Registry No. 959357-53-0, Dec. 21, 2007.
CAS : Registry No. 959371-27-8, Dec. 21, 2007.
CAS : Registry No. 959383-60-9, Dec. 21, 2007.
CAS : Registry No. 959670-14-5, Dec. 28, 2007.
Coll et al., "A small-molecule inhibitor of the NLRP3 inflammasome for the treatment of inflammatory diseases," Nature Medicine, 21(3):248-255, (2015).
Husain et al., "Synthesis of Some New N1-(2-Aryl-6,8-substituted-4 quinazolon-3-yl)-N3-arylsulphonylureas as Hypoglycemic Agents," Indian Journal of Chemistry, Section B: Organic Chemistry Including Medicinal Chemistry, 19B(10): 916-917, (1980).
Husain et al., "Synthesis of Some New Substituted Sulphonylureas as Oral Hypoglycemic Agents," Indian Journal of Chemistry, Section B: Organic Chemistry Including Medicinal Chemistry, 25B(9):934-938, (1986).
Khuntwal et al., "Credential Role of van der Waal Volumes and Atomic Masses in Modeling Hepatitis C Virus NS5B Polymerase Inhibition by Tetrahydrobenzo-Thiophenes Using SVM and MLR Aided QSAR Studies," Current Bioinformatics, 8(4):465-471, (2013).
Laporte et al., "Tetrahydrobenzothiophene inhibitors of hepatitis C virus NS5B polymerase," Bioorganic and medicinal chemistry letters, 16(1):100-103, (2006).
Li et al., "Synthesis and Fungicidal Activity of Novel 2-oxocycloalkylsulfonylureas," Journal of Agriculture and Food Chemistry, 53(6):2202-2206, (2005).
Lowe et al., "Synthesis of Heterocyclic Sulfonylureas," Journal of Heterocyclic Chemistry, 33(3):763-766, (1996).
Ouf et al., "Sulphonyl Ureas and Thioureas of 1,3,4—Thiodiazole to be Tested as Hypoglycomic Agents," Egypt. J. Pharm. Sci., 21(3-4):189-198, (1980).

(56) References Cited

OTHER PUBLICATIONS

Perregaux et al., "Identification and Characterization of a Novel Class of Interleukin-1 Post-Translational Processing Inhibitors," J. Pharmacol. Exp. Ther., 299(1):187-197, (2001).
Youssef et al., "N1, N3-Diaryl Sulfonylureas as Possible Anticancer Agents," Alex J. Pharm Sci., 8(3):223-225, (1994).
Youssef et al., "Synthesis of Sulofenur Analoges as Antitumour Agents: Part II," Med Chem Res, 11(9):481-503, (2002).
WIPO Application No. PCT/IB2017/053059, PCT International Preliminary Report on Patentability dated Dec. 5, 2019.
Ambrogi et al., "New Oral Antidiabetic Drugs Part III", Arzneimittel-Forschung, 22(3): 542-544, 1972.
Kharbanda et al., "Antidiabetic effect of novel benzenesulfonylureas as PPAR-g agonists and their anticancer effect", Bioorganic & Medicinal Chemistry Letters, 25: 4601-4605, 2015.
Murthy et al., "New Hypoglycemic Agents: Synthesis and Hypoglycemic Activity of Some New 1-[{p-(4-oxo-2-substituted-3(4H)-quinazolinyl)-phenyl}sulphonyl]-3-aryl/cyclohexyl-2-thioureas", Current Science, 56(24):1263-1265, 1987.
Plumpe et al., "Isoxazolcarboxamidoalkylbenzolsulfonyl-harnstoffe, -semicarbazide und—aminopyrimidine sowie damit verwandte Verbindungen und ihre blutzuckersenkende Wirkung", Arzneimittel-Forshung, 24(3a): 363-374, 1974, English Abstract.
Weyer et al., "Blutzuckersenkende Chinolin-8-carboxamidoalkyl-benzolsulfonamidderivative", Arzneimittel-Forschung, 24(3): 269-275, 1974, English Abstract.
Yilmaz et al., "Synthesis of pro-apoptotic indapamide derivatives as anticancer agents", Journal of Enzyme Inhibition and Medicinal Chemistry, 30(6): 967-980, 2015.
CAS Registry No. 1026892-76-1; STN Entry Date Jun. 10, 2008.
CAS Registry No. 1332606-77-5; STN Entry Date Sep. 16, 2011.
CAS Registry No. 663215-37-0; STN Entry Date Mar. 15, 2004.
Hill et al., "Dual Action Sulfonylureas: NLRP3 Inhibition and Insulin Secretion," Institute for Molecular Bioscience, Poster, 1 page, (2016).
Laliberte et al., "Glutathione S-Transferase Omega 1-1 Is a Target of Cytokine Release Inhibitory Drugs and May Be Responsible for Their Effect on Interleukin-1,8 Posttranslational Processing," Journal of Biological Chemistry, 278(19): 16567-16578, (2003).
Proks et al., "Sulfonylurea Stimulation of Insulin Secretion," Diabetes, 51 (Suppl. 3):S368-S376, (2002).
Sarges et al., "Sulfamylurea Hypoglycemic Agents. 6. High-Potency Derivatives," Journal of Medicinal Chemistry, 19(5):695-709, (1976).
WIPO Application No. PCT/IB2017/053059, PCT International Search Report and Written Opinion of the International Searching Authority dated Aug. 8, 2017.
Balant, ed in Wolff et al. Burger's Medicinal Chemistry and drug discovery, 5th Ed., vol. 1. Principles and practice, pp. 949-982, 1995.
Banker, et al., Prodrugs, Modern Pharmaceutics, 3rd edition, Revised and Expanded, pp. 451 and 596, (1995).
Belikov, "Pharmaceutical chemistry", chapter 2.6 "The interconnection between chemical structure, properties of substances and their effect on the body", MEDpress-inform, Moscow, 2007, p. 27-29, Brief Statement of Relevance.
Bundgaard, Design of Prodrugs, Chapter 1, p. 1, 1985.
CAS 104843-72-3, Jan. 1, 1986.
CAS 170648-58-5, Jan. 1, 1995.
CAS 36628-63-4, Jan. 1, 1972.
CAS 84884-72-0, Jan. 1, 1983.
CAS 84884-75-3, Jan. 1, 1983.
CAS 84884-76-4, Jan. 1, 1983.
CAS 84884-82-2, Jan. 1, 1983.
CAS 84884-90-2, Jan. 1, 1983.
Disease—Wikipedia, retrieved from the internet on Feb. 2, 2022 at: https://en.wikipedia.org/wiki/Disease.
Ettmayer, et al., "Lessons learned from marketed and investigational prodrugs" J. Med. Chem., 47(10):2394-2404 (2004).
Han, "Targeted prodrug design to optimize drug delivery" AAPS Pharmsci. 2(1) Article 6: 1-11, (2000).
Himiceskij, Chemical Encyclopedia, (1983), p. 130-131, Brief Statement of Relevance.
Parajuli, et al., Prodrug as a novel approach of drug delivery—a review, Journal of Drug Delivery & Therapeutics, 2015, 5(3), pp. 5-9.
Picard, et al. "Inhibitors of acyl-CoA cholesterol O-acyltransferase 17. Structure-Activity Relationships of Several Series of Compounds Derived from N-Chlorosulfonyl Isocyanate" J Med. Chem. 39(6): 1243-1252, (1996).
Silverman, Prodrugs and drug delivery systems, the organic chemistry of drug design and drug action, Chapter 8, pp. 352-400, 1992.
Solvation—Wikipedia, retrieved from the internet on Jan. 15, 2022 at: https://en.wikipedia.org/wiki/Solvation.
Stella, "Prodrugs as theraputics" Expert Opinion of theraputic patents, 14(3): 277-280 (2004).
Testa, "Prodrug Research: futile or fertile?" Biochemical Pharmacology, 68 (2004) 2097- 2106.
Zawilska, et al., "Prodrugs: a challenge for the drug development," Pharmacological Reports, 2013, vol. 65, No. 1, pp. 1-14.

* cited by examiner

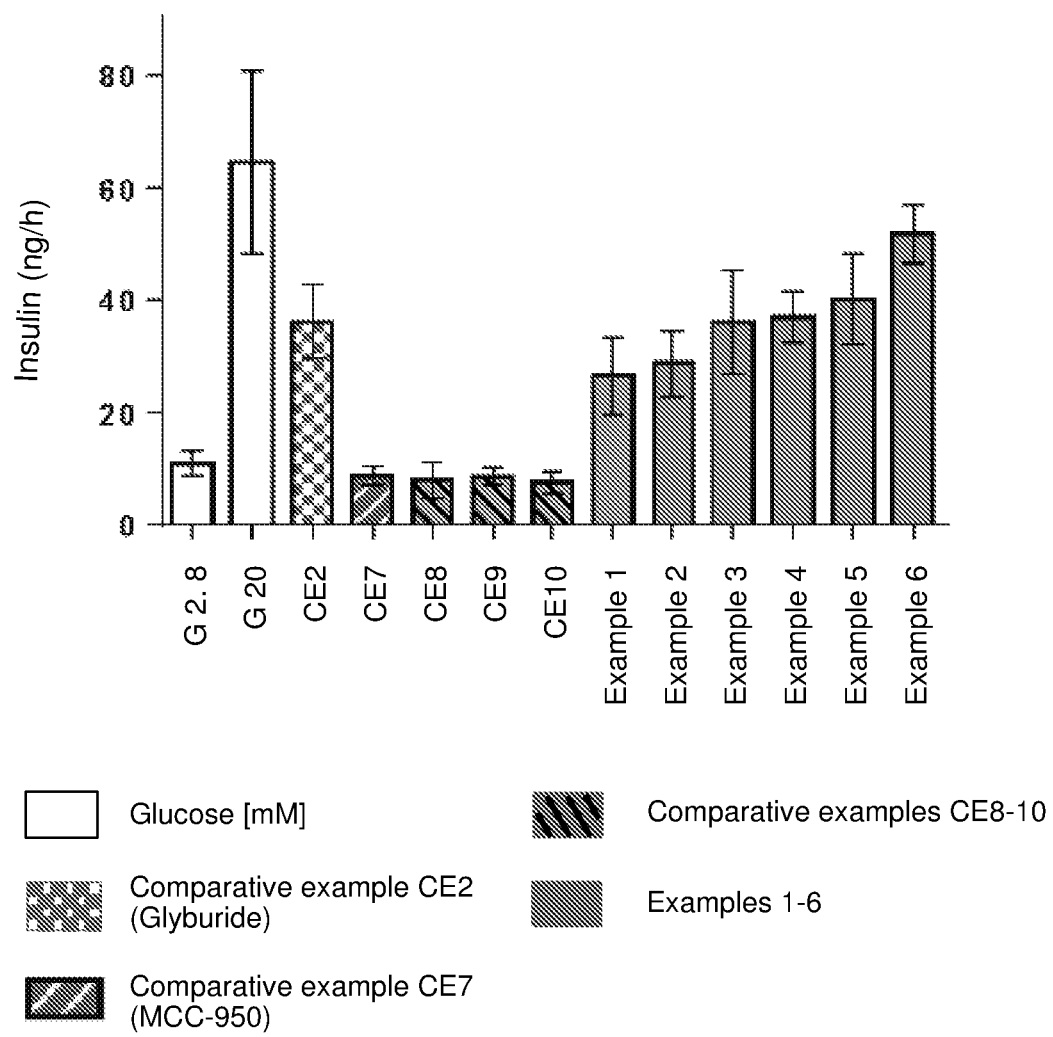

COMPOUNDS AND USES

CROSS-REFERENCE TO RELATED APPLICATION

This application is the US national stage of PCT/IB2017/053059 filed May 24, 2017.

FIELD OF THE INVENTION

The present invention relates to sulphonyl ureas comprising a first cyclic group substituted with a carbonyl-containing group and a second cyclic group substituted at the α-position, and to associated salts, solvates, prodrugs and pharmaceutical compositions. The present invention further relates to the use of such compounds in the treatment and prevention of medical disorders and diseases, most especially by the dual action of NLRP3 inhibition and the stimulation of insulin secretion.

BACKGROUND

The NOD-like receptor (NLR) family, pyrin domain-containing protein 3 (NLRP3) inflammasome is a component of the inflammatory process, and its aberrant activity is pathogenic in inherited disorders such as cryopyrin-associated periodic syndromes (CAPS) and complex diseases such as multiple sclerosis, type 2 diabetes, Alzheimer's disease and atherosclerosis.

NLRP3 is an intracellular signalling molecule that senses many pathogen-derived, environmental and host-derived factors. Upon activation, NLRP3 binds to apoptosis-associated speck-like protein containing a caspase activation and recruitment domain (ASC). ASC then polymerises to form a large aggregate known as an ASC speck. Polymerised ASC in turn interacts with the cysteine protease caspase-1 to form a complex termed the inflammasome. This results in the activation of caspase-1, which cleaves the precursor forms of the proinflammatory cytokines IL-1β and IL-18 (termed pro-IL-1β and pro-IL-18 respectively) to thereby activate these cytokines. Caspase-1 also mediates a type of inflammatory cell death known as pyroptosis. The ASC speck can also recruit and activate caspase-8, which can process pro-IL-1β and pro-IL-18 and trigger apoptotic cell death.

Caspase-1 cleaves pro-IL-1β and pro-IL-18 to their active forms, which are secreted from the cell. Active caspase-1 also cleaves gasdermin-D to trigger pyroptosis. Through its control of the pyroptotic cell death pathway, caspase-1 also mediates the release of alarmin molecules such as IL-33 and high mobility group box 1 protein (HMGB1). Caspase-1 also cleaves intracellular IL-1R2 resulting in its degradation and allowing the release of IL-1α. In human cells caspase-1 may also control the processing and secretion of IL-37. A number of other caspase-1 substrates such as components of the cytoskeleton and glycolysis pathway may contribute to caspase-1-dependent inflammation.

NLRP3-dependent ASC specks are released into the extracellular environment where they can activate caspase-1, induce processing of caspase-1 substrates and propagate inflammation.

Active cytokines derived from NLRP3 inflammasome activation are important drivers of inflammation and interact with other cytokine pathways to shape the immune response to infection and injury. For example, IL-1β signalling induces the secretion of the pro-inflammatory cytokines IL-6 and TNF. IL-1β and IL-18 synergise with IL-23 to induce IL-17 production by memory CD4 Th17 cells and by γδT cells in the absence of T cell receptor engagement. IL-18 and IL-12 also synergise to induce IFN-γ production from memory T cells and NK cells driving a Th1 response.

The inherited CAPS diseases Muckle-Wells syndrome (MWS), familial cold autoinflammatory syndrome and neonatal-onset multisystem inflammatory disease are caused by gain-of-function mutations in NLRP3, thus defining NLRP3 as a critical component of the inflammatory process. NLRP3 has also been implicated in the pathogenesis of a number of complex diseases, notably including metabolic disorders such as type 2 diabetes, atherosclerosis, obesity and gout.

A role for NLRP3 in diseases of the central nervous system is emerging, and lung diseases have also been shown to be influenced by NLRP3. Furthermore, NLRP3 has a role in the development of liver disease, kidney disease and aging. Many of these associations were defined using $Nlrp3^{-/-}$ mice, but there have also been insights into the specific activation of NLRP3 in these diseases. In type 2 diabetes mellitus (T2D), the deposition of islet amyloid polypeptide in the pancreas activates NLRP3 and IL-1β signaling, resulting in cell death and inflammation.

Several small molecules have been shown to inhibit the NLRP3 inflammasome. Glyburide inhibits IL-1β production at micromolar concentrations in response to the activation of NLRP3 but not NLRC4 or NLRP1. Other previously characterised NLRP3 inhibitors include parthenolide, 3,4-methylenedioxy-β-nitrostyrene and dimethyl sulfoxide (DMSO), although these agents have limited potency and are nonspecific. Current treatments for NLRP3-related diseases include biologic agents that target IL-1. These are the recombinant IL-1 receptor antagonist anakinra, the neutralizing IL-1β antibody canakinumab and the soluble decoy IL-1 receptor rilonacept. These approaches have proven successful in the treatment of CAPS, and these biologic agents have been used in clinical trials for other IL-1β-associated diseases.

Some diarylsulphonylurea-containing compounds have been identified as cytokine release inhibitory drugs (CRIDs) (Perregaux et al.; J. Pharmacol. Exp. Ther. 299, 187-197, 2001). CRIDs are a class of diarylsulphonylurea containing compounds that inhibit the post-translational processing of IL-1β. Post-translational processing of IL-1β is accompanied by activation of caspase-1 and cell death. CRIDs arrest activated monocytes so that caspase-1 remains inactive and plasma membrane latency is preserved.

Certain sulphonylurea-containing compounds are also disclosed as inhibitors of NLRP3 (Baldwin et al., J. Med. Chem., 59(5), 1691-1710, 2016).

Some sulphonylurea-containing compounds are employed for other purposes. Diabetes mellitus is a group of metabolic diseases characterised by elevated blood sugar levels. This occurs either because the ability to produce insulin is substantially or completely lost, or because cells develop resistance and a reduced capacity to respond to the insulin that is produced. More specifically, Type 1 diabetes mellitus (T1D) is characterized by loss of the insulin-producing beta cells of the islets of Langerhans in the pancreas leading to insulin deficiency. This type of diabetes can be further classified as immune-mediated or idiopathic. The majority of T1D is immune-mediated, wherein beta cells are lost as a result of an autoimmune attack. Type 2 diabetes mellitus (T2D) is characterized by insulin resistance, frequently in combination with reduced insulin secretion. T2D is due primarily to lifestyle factors and genetics. Available treatments for patients with T2D include secretagogues, such as certain sulphonylureas and "glinides" (repaglinide and nateglinide), metformin, thiazolidinediones (TZDs), and dipeptidyl peptidase-4 (DPP-4) inhibitors among oral medications, and insulin and glucagon-like peptide-1 (GLP-1) receptor agonists among parenterally administered agents. These secretagogues stimulate the pancreas to release insulin.

There is a need to provide compounds with improved pharmacological and/or physiological and/or physicochemical properties and/or those that provide a useful alternative to known compounds.

SUMMARY OF THE INVENTION

The present invention is based in part on the recognition that it is desirable to devise a class of compounds which have both NLRP-3 inhibiting and insulin secretagogue activity. Remarkably, it has been found that by appropriate structural design of sulphonylurea substituents, compounds may be synthesised which are both highly potent NLRP-3 inhibitors and powerful inducers of insulin secretion. In achieving this result, new categories of insulin secretagogues and new categories of NLRP-3 inhibitors have been devised.

Accordingly, a first aspect of the invention relates to a compound of formula (I):

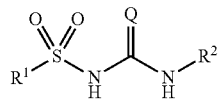

Formula (I)

wherein:
Q is O or S;
$R^1$ is a cyclic group substituted with at least one group X, wherein $R^1$ may optionally be further substituted;
X is any group comprising a carbonyl group; and
$R^2$ is a cyclic group substituted at the α-position, wherein $R^2$ may optionally be further substituted.

In a preferred embodiment, Q is O.

For the purposes of the present specification, where it is stated that a substituent, group or moiety "is a" specific group, it is to be understood that the specific group is attached directly to the remainder of the molecule, with no intervening atom(s) or groups being present. In contrast, where it is stated that a substituent, group or moiety "comprises" a specific group, it is to be understood only that the specific group must be included in the substituent, group or moiety, such that the specific group may be attached to the remainder of the molecule via other atoms, groups or moieties. Thus, in the first aspect of the invention, where it is stated that "$R^1$ is a cyclic group" it is to be understood that the cyclic group is directly attached to the sulphur atom of the sulphonyl group, with no intervening atom(s) or groups being present. Similarly, where it is stated that "$R^2$ is a cyclic group", it is to be understood that the cyclic group is directly attached to the nitrogen atom of the (thio)urea group, with no intervening atom(s) or groups being present. Conversely, in the first aspect of the invention, where it is stated that "X is any group comprising a carbonyl group", it is to be understood only that the group X includes a carbonyl group (C═O); such a group X may further comprise additional atoms, groups or moieties, which may connect the carbonyl group to $R^1$.

For the purposes of the present specification, in an optionally substituted group or moiety:
(i) each hydrogen atom may optionally be substituted with a group independently selected from a halo, —CN, —NO₂, —$R^β$, —OH, —$OR^β$, —SH, —$SR^β$, —NH₂, —$NHR^β$, —$N(R^β)_2$, —CHO, —$COR^β$, —COOH, —$COOR^β$ or —$OCOR^β$ group; and/or
(ii) any two hydrogen atoms attached to the same carbon atom may optionally be substituted with a π-bonded substituent independently selected from ═O, ═S or ═$NR^β$; and/or
(iii) any two hydrogen atoms attached to the same or different atoms, within the same optionally substituted group or moiety, may optionally be substituted with a bridging substituent independently selected from —O—, —S—, —$NR^β$— or —$R^α$—;
wherein each —$R^α$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —$R^β$ groups;
wherein each $R^β$ is independently selected from a $C_1$-$C_6$ alkyl, $C_2$-$C_6$ alkenyl, $C_2$-$C_6$ alkynyl or $C_2$-$C_6$ cyclic group, and wherein any $R^β$ may optionally be substituted with one or more halo groups.

The term "halo" includes fluoro, chloro, bromo and iodo.

Typically a substituted group comprises 1, 2 or 3 substituents, more typically 1 or 2 substituents, and even more typically 1 substituent.

Unless stated otherwise, any divalent bridging substituent (e.g. —O—, —S—, —$NR^β$— or —$R^α$—) of an optionally substituted group or moiety (e.g. $R^1$) must only be attached to the specified group or moiety and may not be attached to a second group or moiety (e.g. $R^2$), even if the second group or moiety can itself be optionally substituted.

Where reference is made to a carbon atom of a hydrocarbyl or other group being replaced by an N, O or S atom, what is intended is that:

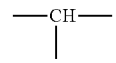

is replaced by

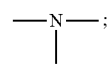

—CH₂— is replaced by —NH—, —O— or —S—;
—CH₃ is replaced by —NH₂, —OH, or —SH;
—CH═ is replaced by —N═;
CH₂═ is replaced by NH═, O═ or S═; or
CH≡ is replaced by N≡.

In the context of the present specification, unless otherwise stated, an "alkyl" substituent group or an alkyl moiety in a substituent group may be linear or branched. Examples of alkyl groups/moieties include methyl, ethyl, n-propyl, i-propyl, n-butyl, i-butyl, t-butyl and n-pentyl groups/moieties. Unless stated otherwise, the term "alkyl" does not include "cycloalkyl". Typically an alkyl group is a $C_1$-$C_{12}$ alkyl group. More typically an alkyl group is a $C_1$-$C_6$ alkyl group. An "alkylene" group is similarly defined as a divalent alkyl group.

An "alkenyl" substituent group or an alkenyl moiety in a substituent group refers to an unsaturated alkyl group or moiety having one or more carbon-carbon double bonds. Examples of alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1,4-hexadienyl groups/moieties. Unless stated otherwise, the term "alkenyl" does not include "cycloalkenyl". Typically an alkenyl group is a $C_2$-$C_{12}$ alkenyl group. More typically an alkenyl group is a $C_2$-$C_6$ alkenyl group. An "alkenylene" group is similarly defined as a divalent alkenyl group.

An "alkynyl" substituent group or an alkynyl moiety in a substituent group refers to an unsaturated alkyl group or moiety having one or more carbon-carbon triple bonds. Examples of alkynyl groups/moieties include ethynyl, propargyl, but-1-ynyl and but-2-ynyl. Typically an alkynyl group is a $C_2$-$C_{12}$ alkynyl group. More typically an alkynyl group is a $C_2$-$C_6$ alkynyl group. An "alkynylene" group is similarly defined as a divalent alkynyl group.

A "cyclic" substituent group or a cyclic moiety in a substituent group refers to any hydrocarbyl ring, wherein the hydrocarbyl ring may be saturated or unsaturated and may include one or more heteroatoms, e.g. N, O or S, in its carbon skeleton. Examples of cyclic groups include cycloalkyl, cycloalkenyl, heterocyclic, aryl and heteroaryl groups as discussed below. A cyclic group may be monocyclic, bicyclic (e.g. fused or spiro), or polycyclic. Typically, a cyclic group is a 3 to 12 membered cyclic group, i.e. the ring structure(s) excluding non-ring atoms contain from 3 to 12 atoms. More typically, a cyclic group is a monocyclic 3 to 7 membered cyclic group.

As used herein, where it is stated that a cyclic group is monocyclic, it is to be understood that the cyclic group is not substituted with a divalent bridging substituent (e.g. —O—, —S—, —NR$^\beta$— or —R$^\alpha$—) so as to form a fused or spiro substituent. However, unless stated otherwise, a substituted monocyclic group may be substituted with one or more monovalent cyclic groups. Similarly, where it is stated that a group is bicyclic, it is to be understood that the cyclic group including any fused or spiro divalent bridging substituents attached to the cyclic group, but excluding any monovalent cyclic substituents, is bicyclic.

A "heterocyclic" substituent group or a heterocyclic moiety in a substituent group refers to a cyclic group or moiety including one or more carbon atoms and one or more heteroatoms, e.g. N, O or S, in the ring structure. Examples of heterocyclic groups include heteroaryl groups as discussed below and non-aromatic heterocyclic groups such as tetrahydrofuranyl, pyrrolidinyl, tetrahydrothiophenyl, tetrahydropyranyl, piperidinyl, piperazinyl, morpholinyl and thiomorpholinyl groups.

A "cycloalkyl" substituent group or a cycloalkyl moiety in a substituent group refers to a saturated hydrocarbyl ring containing, for example, from 3 to 7 carbon atoms, examples of which include cyclopropyl, cyclobutyl, cyclopentyl and cyclohexyl. Unless stated otherwise, a cycloalkyl substituent group or moiety may include monocyclic, bicyclic or polycyclic hydrocarbyl rings.

A "cycloalkenyl" substituent group or a cycloalkenyl moiety in a substituent group refers to a non-aromatic unsaturated hydrocarbyl ring having one or more carbon-carbon double bonds and containing, for example, from 3 to 7 carbon atoms, examples of which include cyclopent-1-en-1-yl, cyclohex-1-en-1-yl and cyclohex-1,3-dien-1-yl. Unless stated otherwise, a cycloalkenyl substituent group or moiety may include monocyclic, bicyclic or polycyclic hydrocarbyl rings.

An "aryl" substituent group or an aryl moiety in a substituent group refers to an aromatic hydrocarbyl ring. The term "aryl" includes monocyclic aromatic hydrocarbons and polycyclic fused ring aromatic hydrocarbons wherein all of the fused ring systems (excluding optional substituents) are aromatic. Examples of aryl groups/moieties include phenyl, naphthyl, anthracenyl and phenanthrenyl.

A "heteroaryl" substituent group or a heteroaryl moiety in a substituent group refers to an aromatic heterocyclic group or moiety. The term "heteroaryl" includes monocyclic aromatic heterocycles and polycyclic fused ring aromatic heterocycles wherein all of the fused ring systems (excluding optional substituents) are aromatic. Examples of heteroaryl groups/moieties include the following:

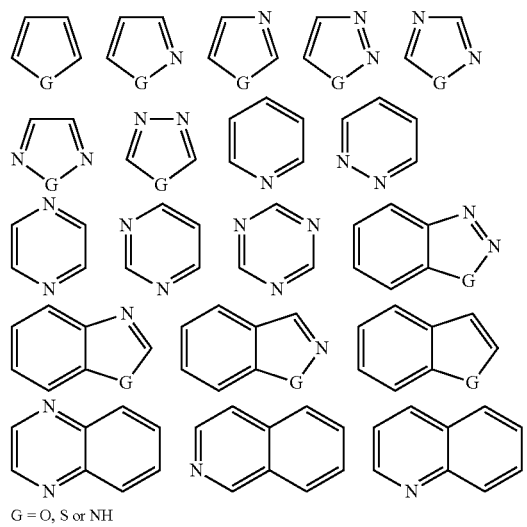

G = O, S or NH

For the purposes of the present specification, where a combination of moieties is referred to as one group, for example, arylalkyl, arylalkenyl, arylalkynyl, alkylaryl, alkenylaryl or alkynylaryl, the last mentioned moiety contains the atom by which the group is attached to the rest of the molecule. An example of an arylalkyl group is benzyl.

In the context of the present specification, unless otherwise stated, a $C_x$-$C_y$ group is defined as a group containing from x to y carbon atoms. For example, a $C_1$-$C_4$ alkyl group is defined as an alkyl group containing from 1 to 4 carbon atoms. Optional substituents and moieties are not taken into account when calculating the total number of carbon atoms in the parent group substituted with the optional substituents and/or containing the optional moieties.

For the avoidance of doubt, replacement heteroatoms, such as nitrogen, oxygen and sulphur are not to be counted as carbon atoms when calculating the number of carbon atoms in a $C_x$-$C_y$ group. For example, a morpholinyl group is to be considered a $C_4$ heterocyclic group, not a $C_6$ heterocyclic group.

In one embodiment of the first aspect of the invention, $R^2$ is an aryl or a heteroaryl group, wherein the aryl or the heteroaryl group is substituted at the α-position, and wherein $R^2$ may optionally be further substituted. Typically, $R^2$ is an aryl or a heteroaryl group, wherein the aryl or the heteroaryl group is substituted at the α and α' positions, wherein $R^2$ may optionally be further substituted. For example, $R^2$ may be a phenyl group substituted at the 2- and 6-positions.

In another embodiment, $R^2$ is a cyclic group substituted at the α and α' positions, wherein $R^2$ may optionally be further substituted. For example, $R^2$ may be a cycloalkyl, cycloalkenyl or non-aromatic heterocyclic group substituted at the α and α' positions.

As used herein, the nomenclature α, β, α', β' refers to the position of the atoms of the cyclic group relative to the point of attachment of a moiety such as $R^2$ to the remainder of the molecule. For example, where $R^2$ is a 1,2,3,5,6,7-hexahydro-s-indacen-4-yl moiety, the α, β, α' and β' positions are as follows:

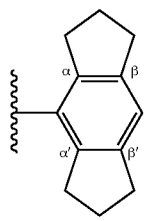 [SMILES: *c1c2c(cc3c1CCC3)CCC2]

Similarly, reference to substitution at the n-position in relation to a group, where n is an integer, refers to the position of substitution relative to the point of attachment of the group to the remainder of the molecule. For example, where $R^1$ is a 6-membered heteroaryl group the positions of the group may be numbered as follows:

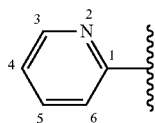

In any of the above embodiments, typical substituents at the α and/or α' positions may be independently selected from —$R^3$, —$OR^3$ and —$COR^3$ groups, wherein each $R^3$ is independently selected from a $C_1$-$C_6$ alkyl, $C_2$-$C_6$ alkenyl, $C_2$-$C_6$ alkynyl or $C_2$-$C_6$ cyclic group and wherein each $R^3$ is optionally further substituted with one or more halo groups. More typically, the substituents at the α and α' positions are independently selected from alkyl and cycloalkyl groups, such as $C_3$-$C_6$ branched alkyl and $C_3$-$C_6$ cycloalkyl groups, e.g. isopropyl, cyclopropyl, cyclohexyl or t-butyl groups, wherein the alkyl and cycloalkyl groups are optionally further substituted with one or more fluoro and/or chloro groups.

Other typical substituents at the α and/or α' positions include cycloalkyl, cycloalkenyl, non-aromatic heterocyclic, aryl or heteroaryl rings which are fused to the parent cyclic group across the α,β and/or α',β' positions respectively. Such fused cyclic groups are described in greater detail below.

In one embodiment $R^2$ is a fused aryl or a fused heteroaryl group, wherein the aryl or heteroaryl group is fused to one or more cycloalkyl, cycloalkenyl, non-aromatic heterocyclic, aryl or heteroaryl rings, wherein $R^2$ may optionally be further substituted.

In another embodiment, $R^2$ is a fused aryl or a fused heteroaryl group, wherein the aryl or heteroaryl group is fused to two or more independently selected cycloalkyl, cycloalkenyl, non-aromatic heterocyclic, aryl or heteroaryl rings, wherein $R^2$ may optionally be further substituted. Typically, the two or more cycloalkyl, cycloalkenyl, non-aromatic heterocyclic, aryl or heteroaryl rings are each ortho-fused to the aryl or heteroaryl group, i.e. each fused cycloalkyl, cycloalkenyl, non-aromatic heterocyclic, aryl or heteroaryl ring has only two atoms and one bond in common with the aryl or heteroaryl group. Typically, $R^2$ is tricyclic.

In yet another embodiment, $R^2$ is a fused aryl or a fused heteroaryl group, wherein a first cycloalkyl, cycloalkenyl, non-aromatic heterocyclic, aryl or heteroaryl ring is fused to the aryl or heteroaryl group across the α,β positions and a second cycloalkyl, cycloalkenyl, non-aromatic heterocyclic, aryl or heteroaryl ring is fused to the aryl or heteroaryl group across the α',β' positions, wherein $R^2$ may optionally be further substituted.

Typically in any embodiment where $R^2$ is a fused aryl or a fused heteroaryl group, Q is O.

In one embodiment, —$R^2$ has a formula selected from:

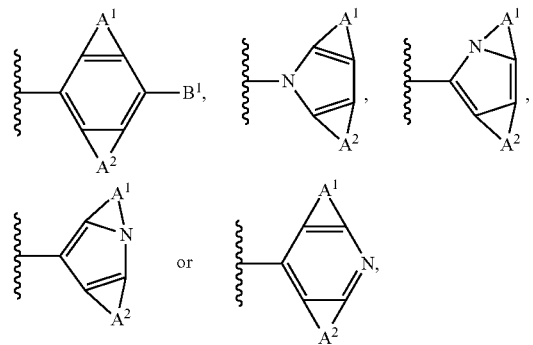

wherein $A^1$ and $A^2$ are each independently selected from an optionally substituted alkylene or alkenylene group, wherein one or more carbon atoms in the backbone of the alkylene or alkenylene group may optionally be replaced by one or more heteroatoms N, O or S, and wherein B1 is hydrogen or any optional substituent. B1 and any optional substituent attached to $A^1$ or $A^2$ may together with the atoms to which they are attached form a further fused cycloalkyl, cycloalkenyl, non-aromatic heterocyclic, aryl or heteroaryl ring which may itself be optionally substituted. Similarly, any optional substituent attached to $A^1$ and any optional substituent attached to $A^2$ may also together with the atoms to which they are attached form a further fused cycloalkyl, cycloalkenyl, non-aromatic heterocyclic, aryl or heteroaryl ring which may itself be optionally substituted.

Typically, B1 is hydrogen or a halo, hydroxyl, —CN, —$NO_2$, —B2 or —OB2 group, wherein B2 is a $C_1$-$C_4$ alkyl group which may optionally be halo-substituted.

Typically, any ring containing $A^1$ or $A^2$ is a five or a six membered ring. Typically, $A^1$ and $A^2$ are unsubstituted or substituted with one or more halo, hydroxyl, —CN, —$NO_2$, —B3 or —OB3 groups, wherein B3 is a $C_1$-$C_4$ alkyl group which may optionally be halo-substituted.

In a further embodiment, —$R^2$ has a formula selected from:

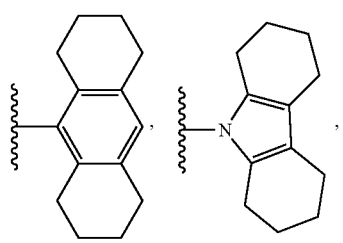

-continued

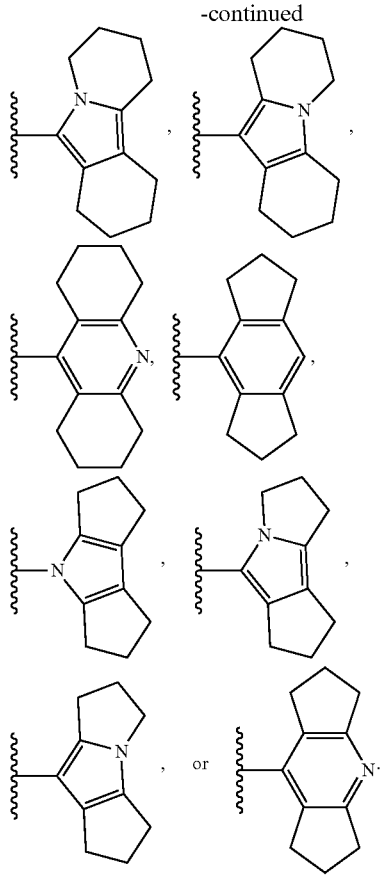

Most typically, —R² has the formula:

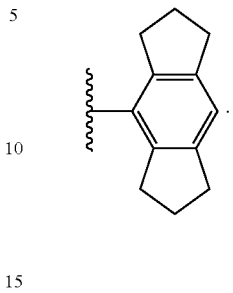

In one embodiment, R¹ is an aryl or a heteroaryl group substituted with at least one group X, wherein R¹ may optionally be further substituted. Typically R¹ is monocyclic.

In one embodiment, R¹ is a 6-membered cyclic group, such as an aryl or a heteroaryl group, substituted with at least one group X, wherein R¹ may optionally be further substituted. Examples of such 6-membered cyclic groups include phenyl, pyridinyl, cyclohexyl and cyclohexenyl groups and the like. In one aspect of such an embodiment, R² is a fused aryl or a fused heteroaryl group, wherein a first cycloalkyl, cycloalkenyl, non-aromatic heterocyclic, aryl or heteroaryl ring is fused to the aryl or heteroaryl group across the α,β positions and a second cycloalkyl, cycloalkenyl, non-aromatic heterocyclic, aryl or heteroaryl ring is fused to the aryl or heteroaryl group across the α',β' positions, and wherein R² may optionally be further substituted. Examples of such compounds include:

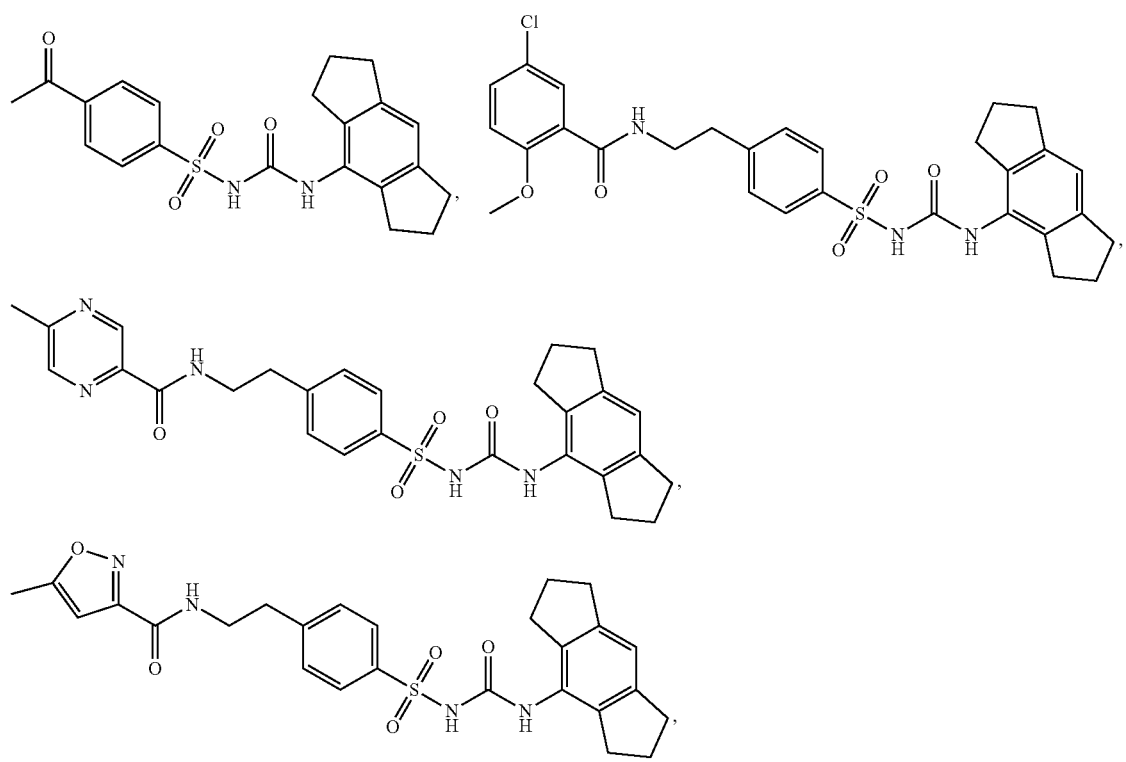

-continued
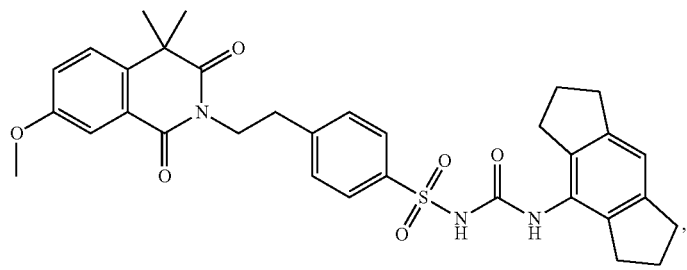
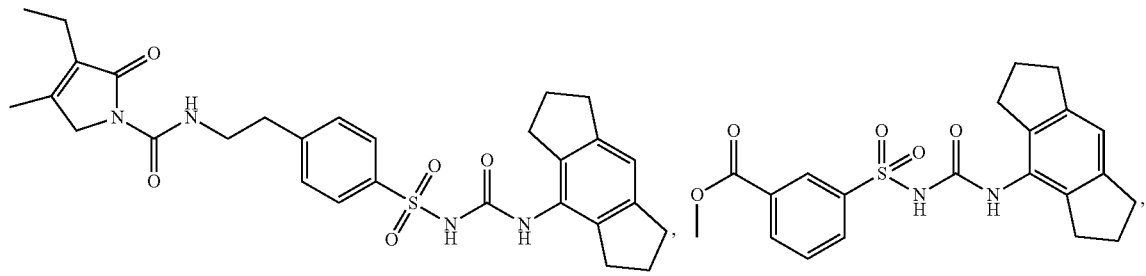
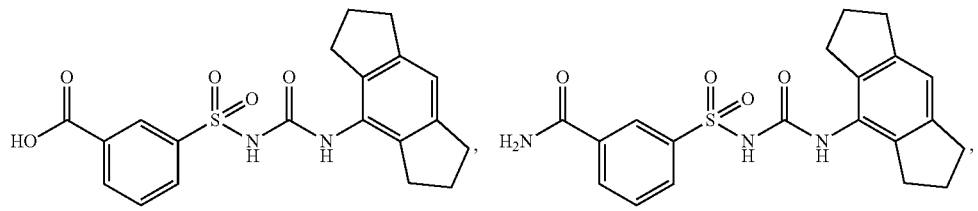
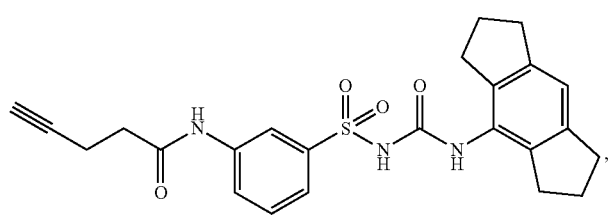
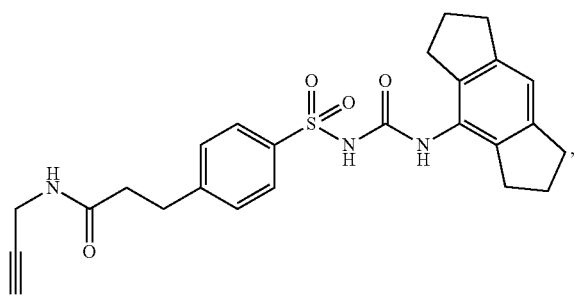
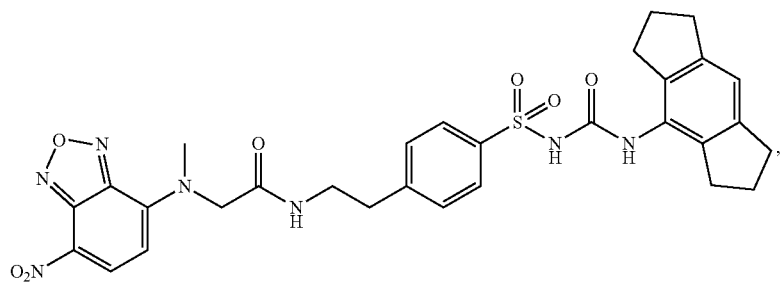

-continued
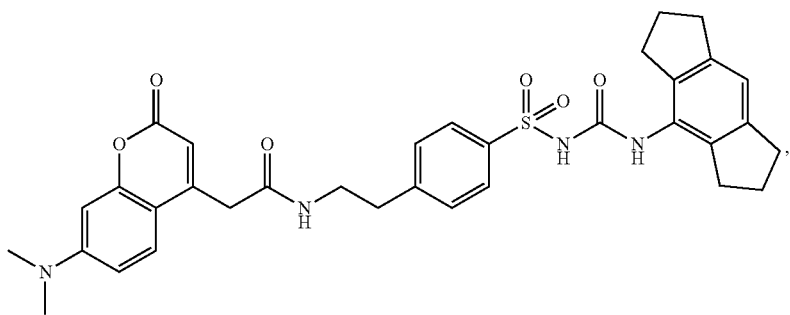
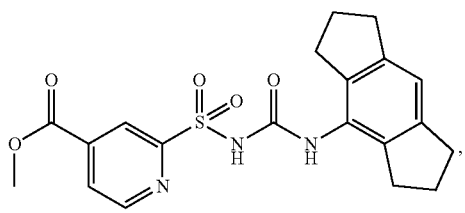
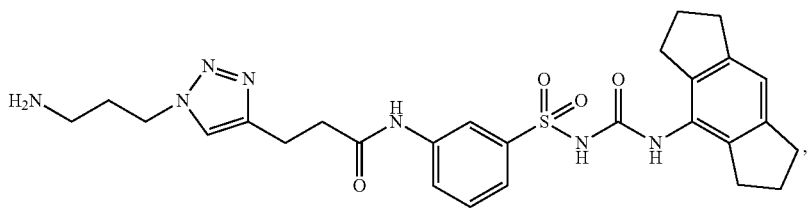
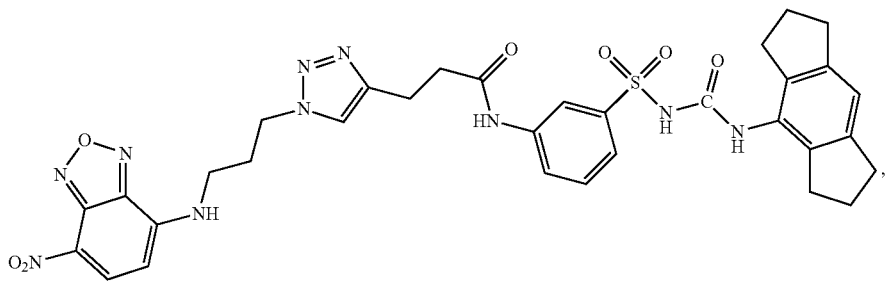
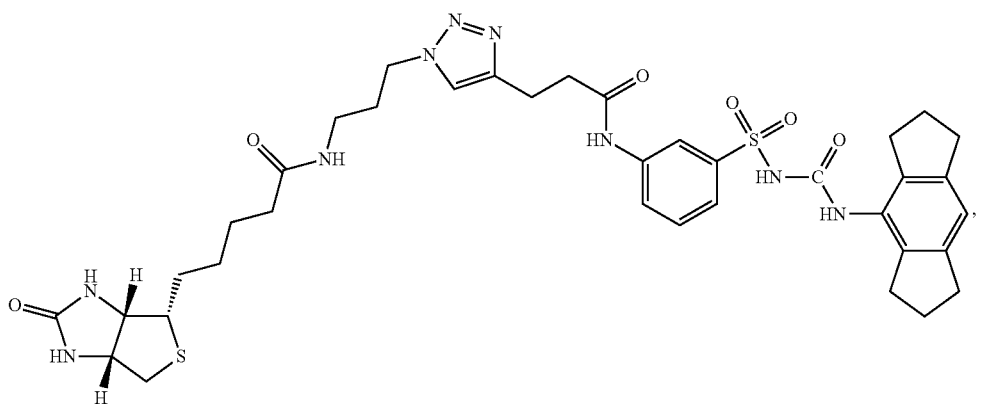

-continued
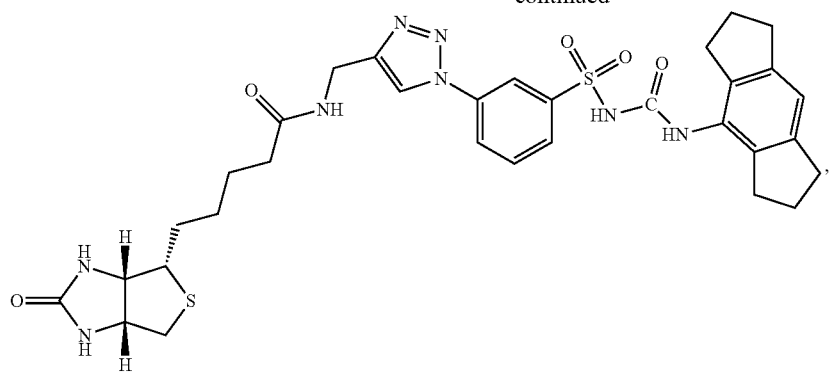
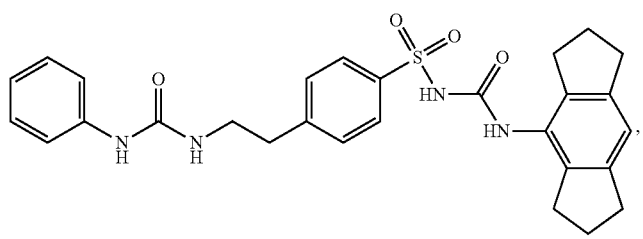
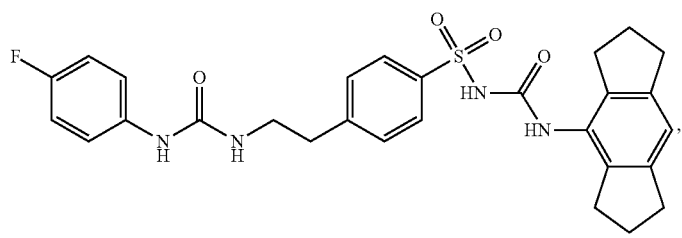
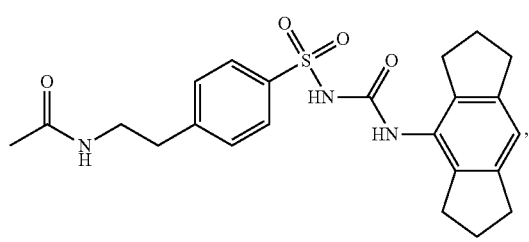
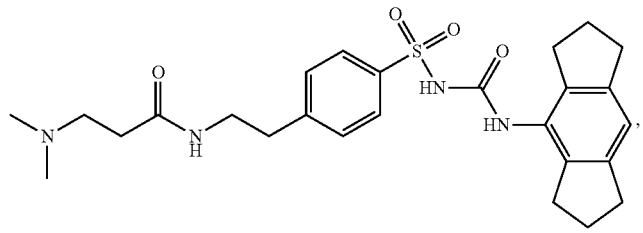
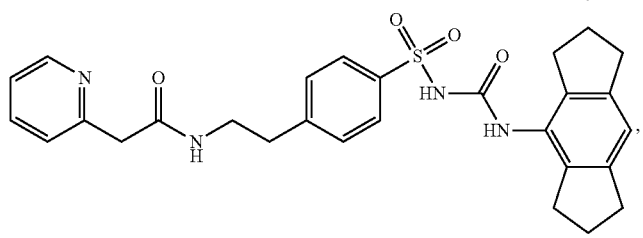

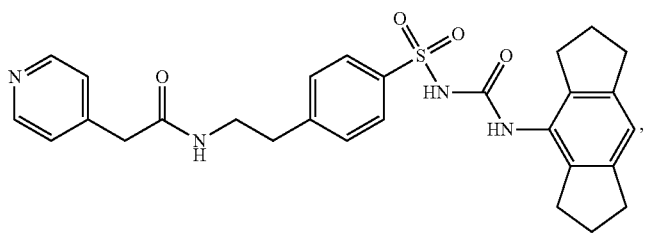
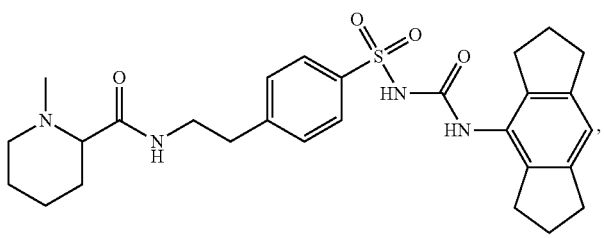
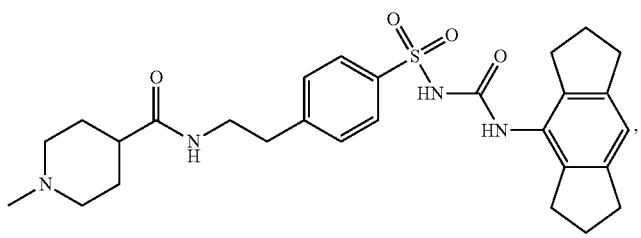
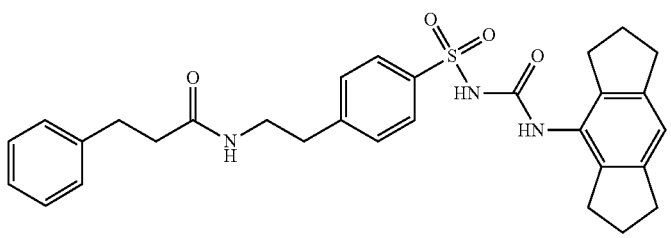
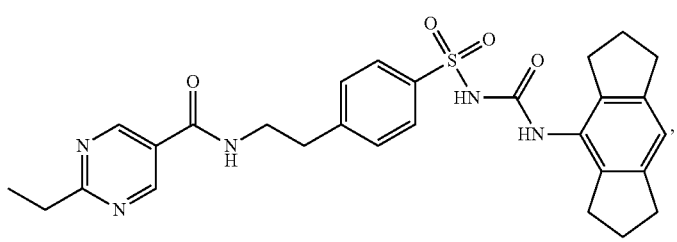
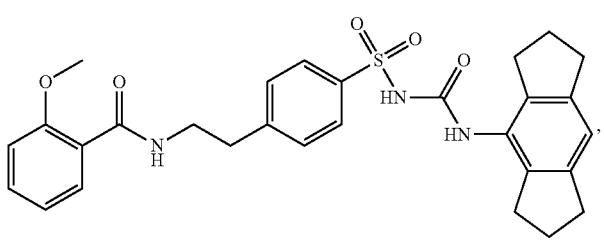
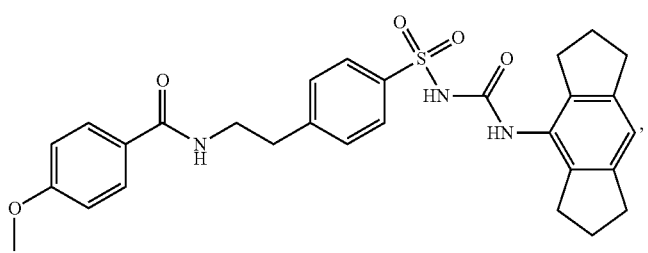

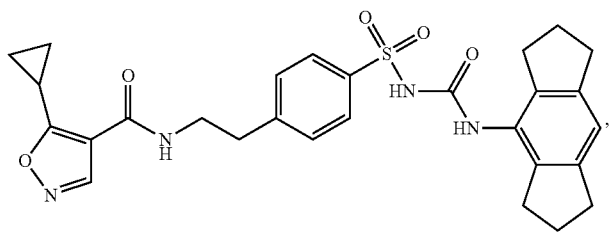
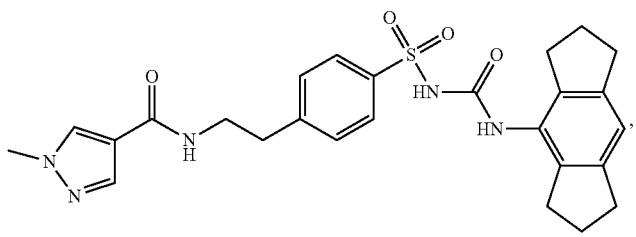
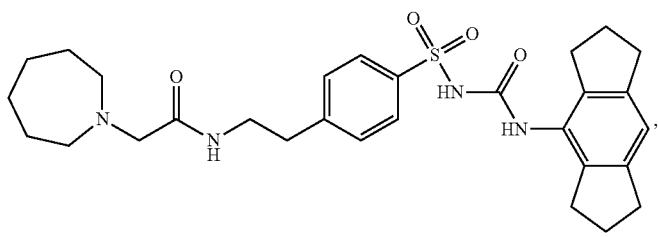
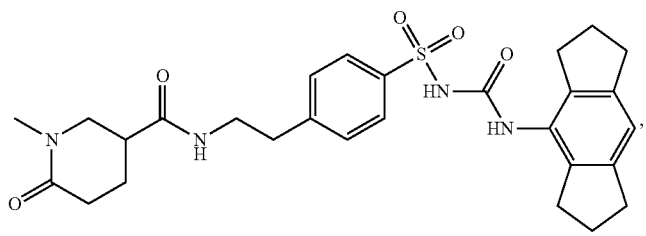
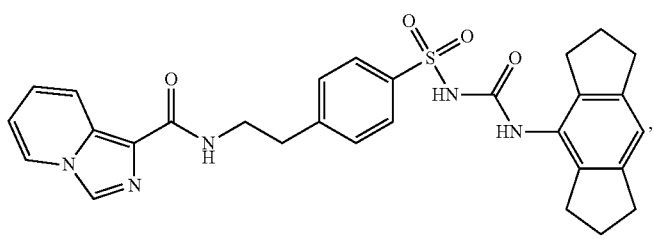
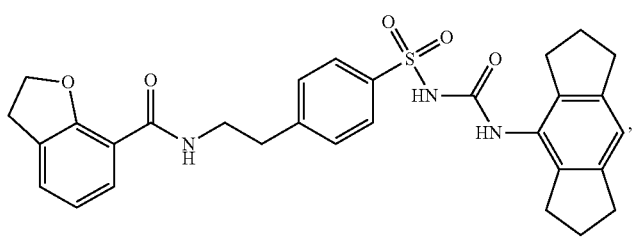
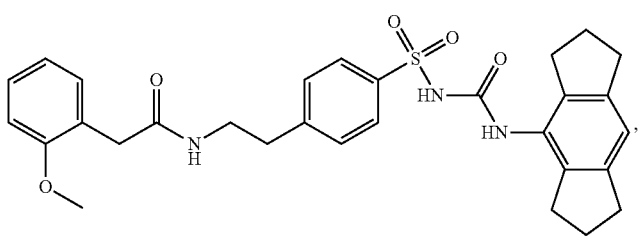

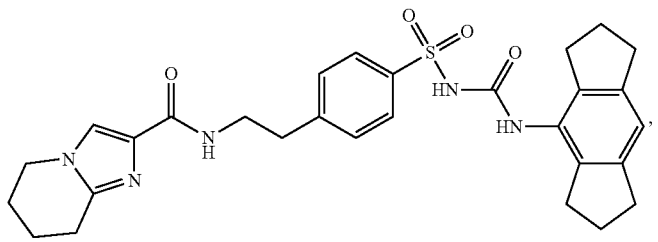
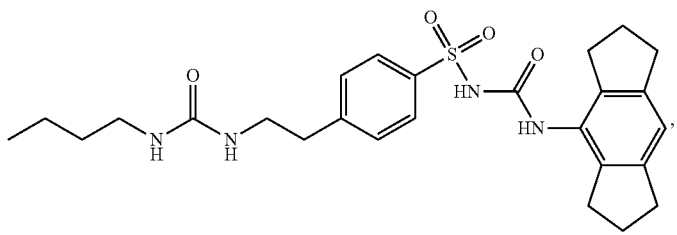
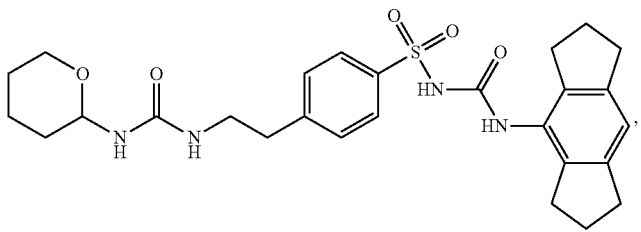
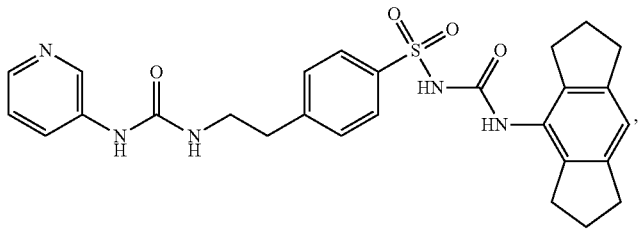
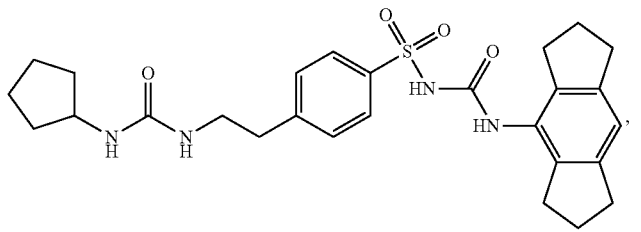
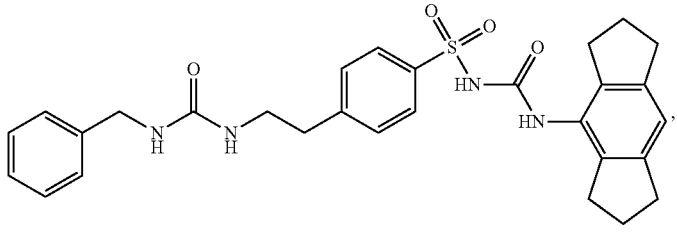
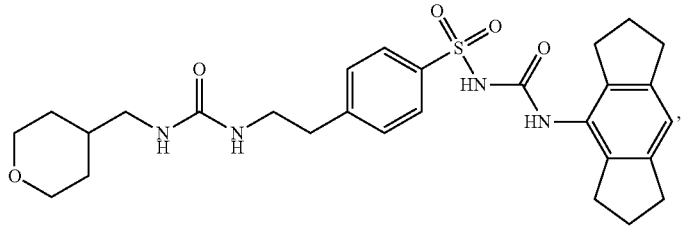

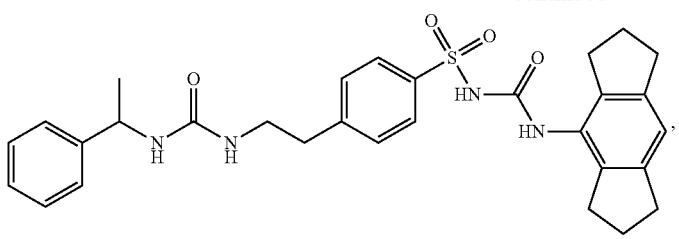
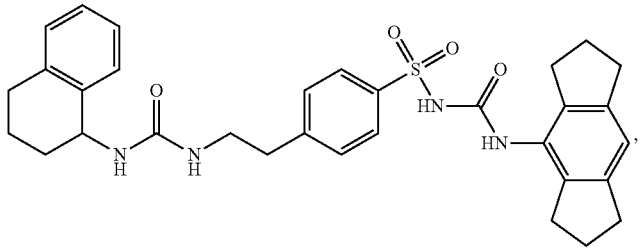
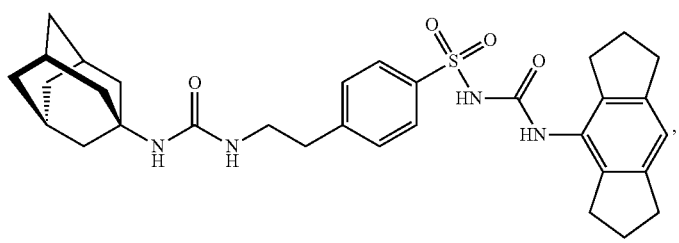
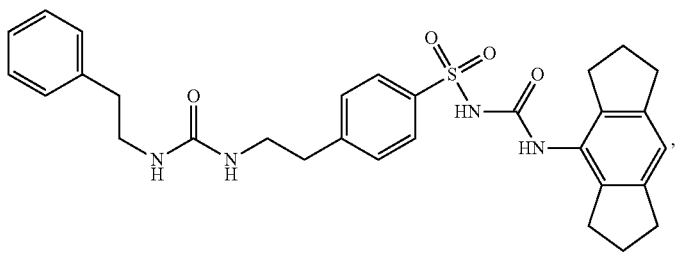
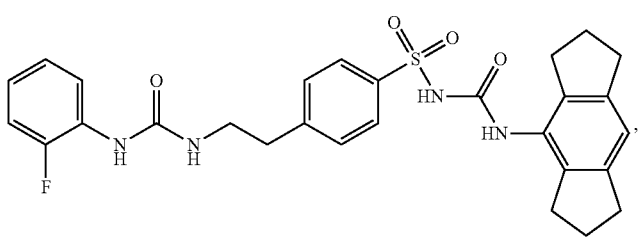
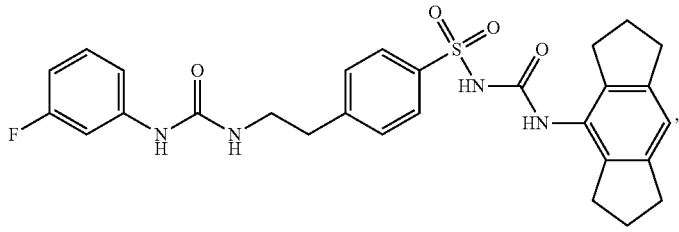
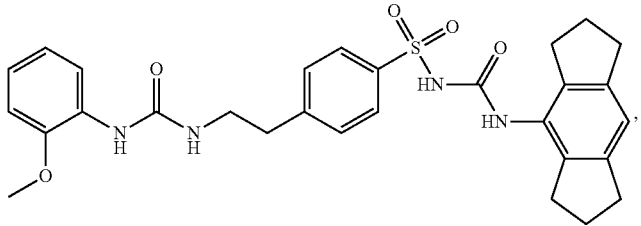

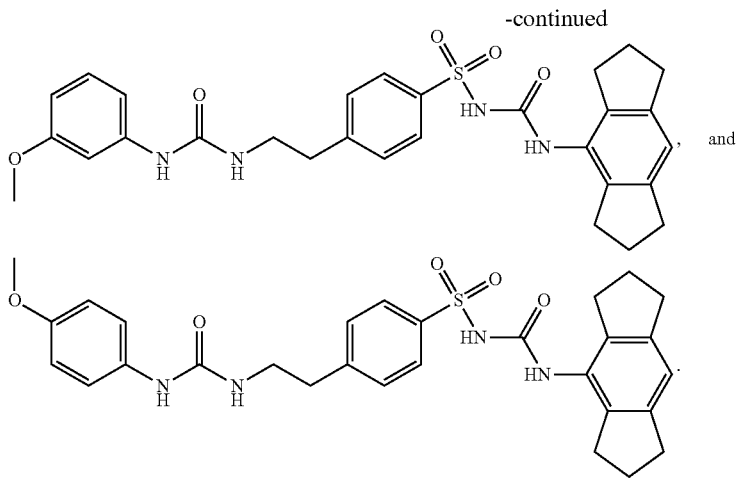
and

In another embodiment, $R^1$ is a 6-membered cyclic group, such as an aryl or a heteroaryl group, substituted at the 4-position with at least one group X, wherein X is attached to the 6-membered cyclic group only via the 4-position, and wherein the 6-membered cyclic group may optionally be further substituted. For example, X may be monovalent. Alternatively, X may be divalent but attached to the 6-membered cyclic group only via the 4-position, for example via a double bond or as a spiro group. Typically the 6-membered cyclic group is monocyclic. In one aspect of such an embodiment, $R^2$ is an aryl or a heteroaryl group, wherein the aryl or the heteroaryl group is substituted at the α and α' positions, wherein $R^2$ may optionally be further substituted.

In yet another embodiment, $R^1$ is a phenyl group or a 6-membered heteroaryl group, wherein the phenyl group or the 6-membered heteroaryl group is substituted at the 4-position with a group X, wherein X is monovalent, and wherein the phenyl group or the 6-membered heteroaryl group (e.g. a pyridinyl group) may optionally be further substituted. In one aspect of such an embodiment, $R^2$ is an aryl or a heteroaryl group, wherein the aryl or the heteroaryl group is substituted at the α-position, and wherein $R^2$ may optionally be further substituted. Examples of such compounds include:

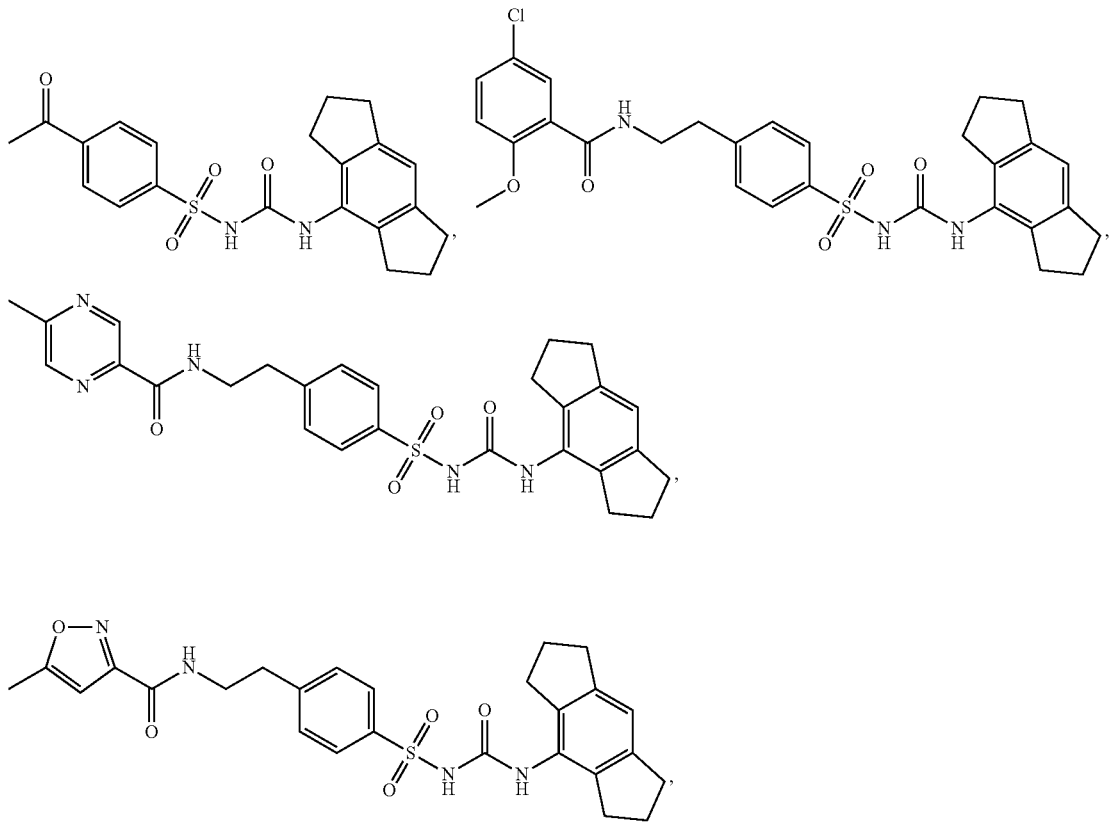

-continued
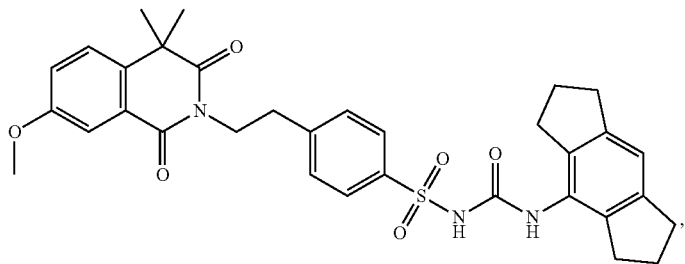
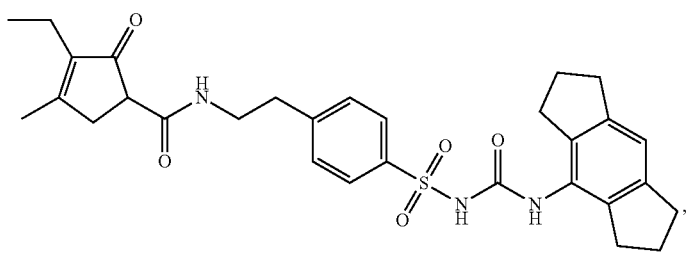
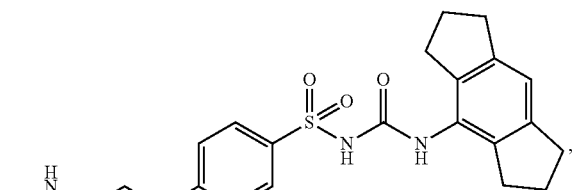
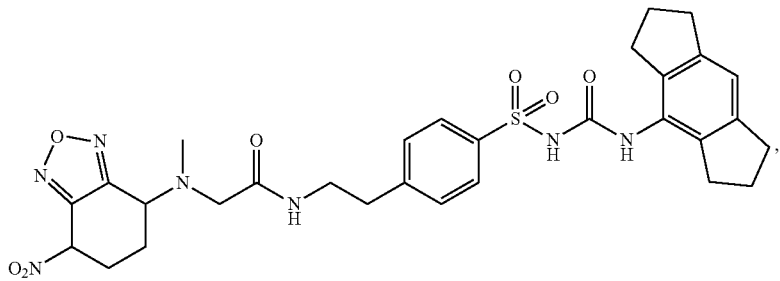
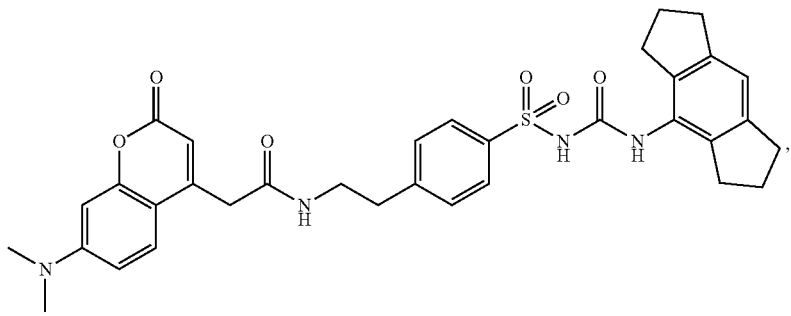
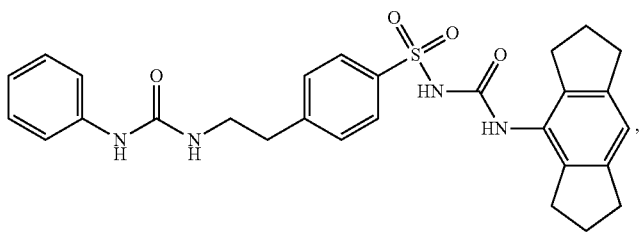

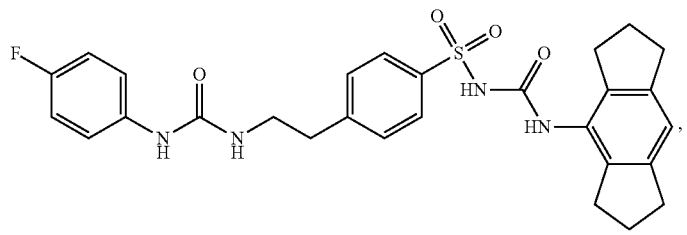
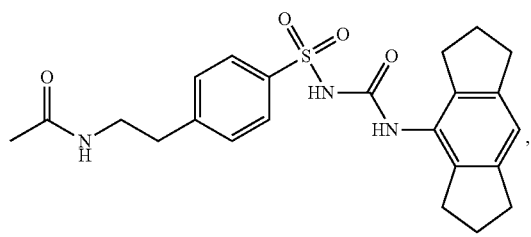
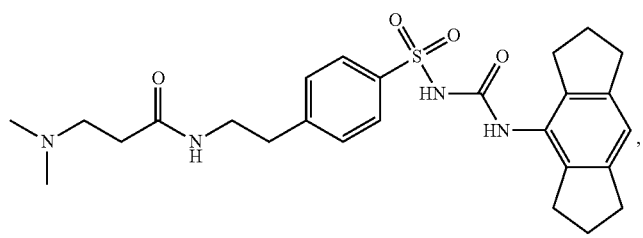
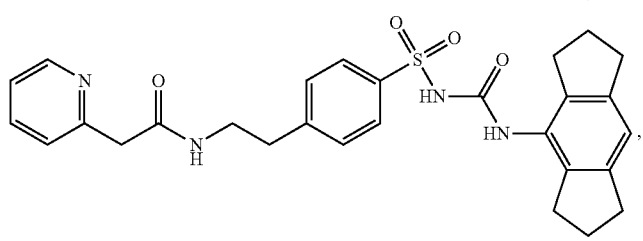
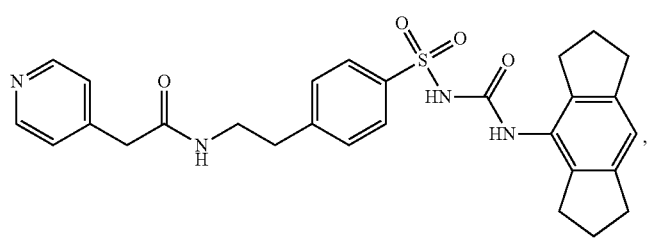
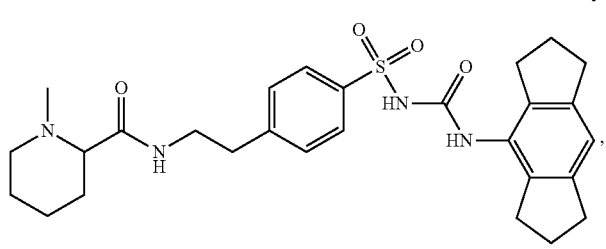
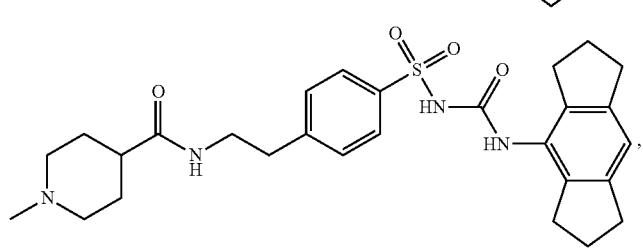

-continued
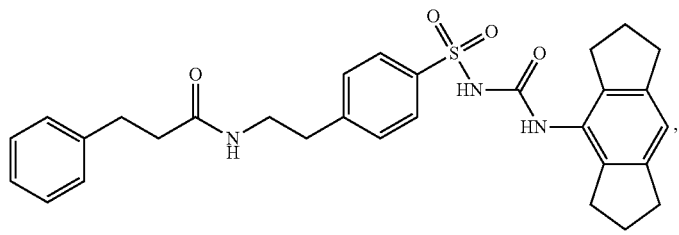
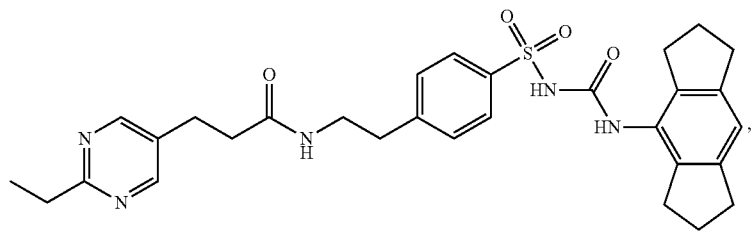
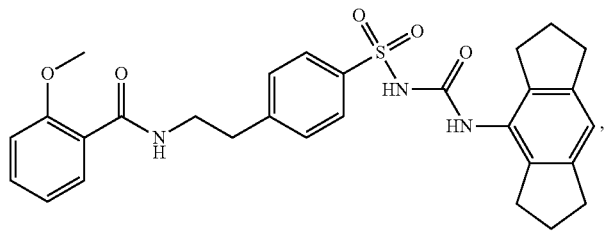
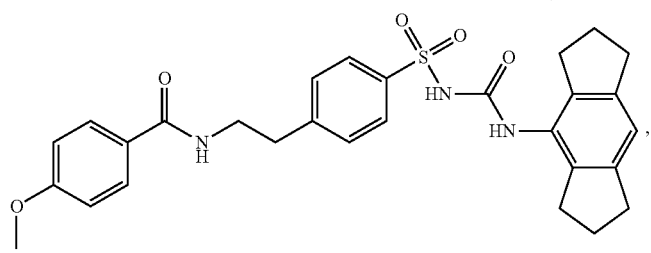
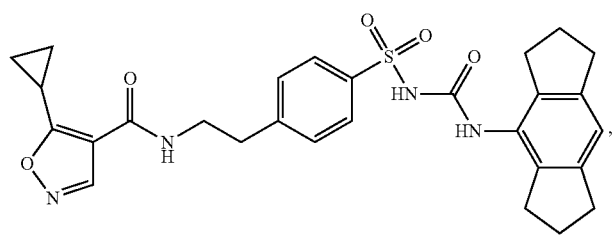
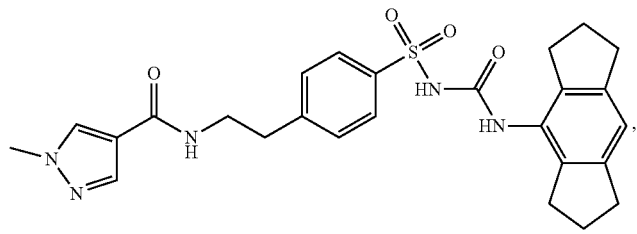
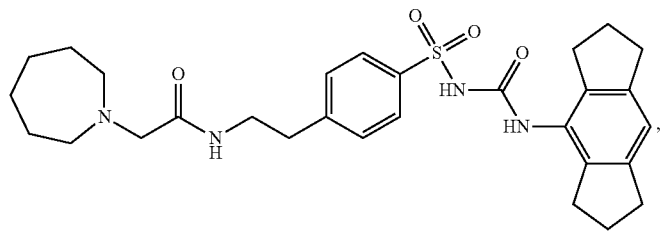

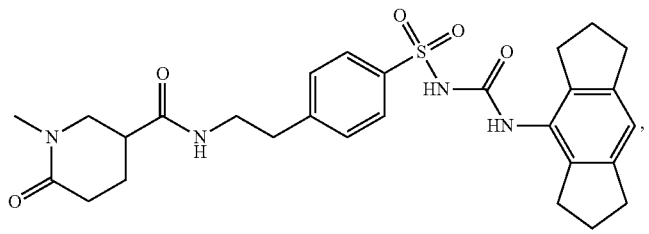
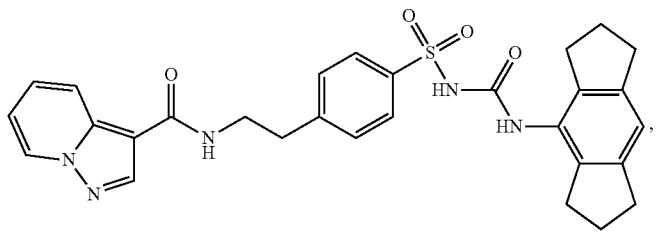
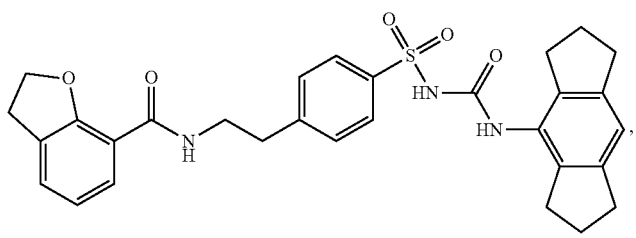
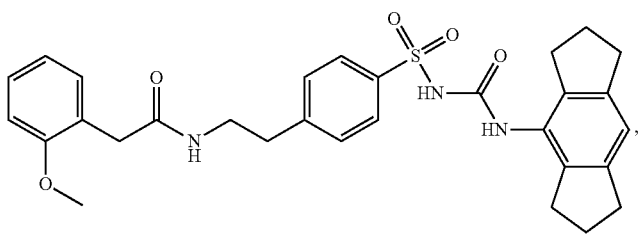
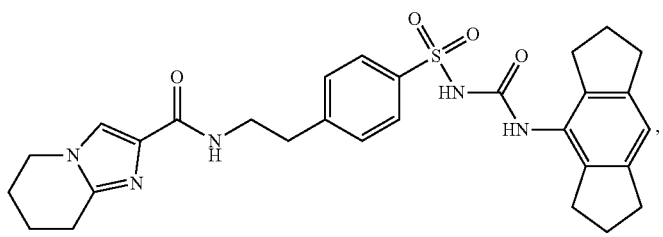
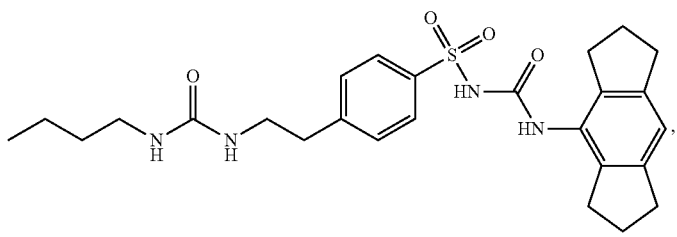
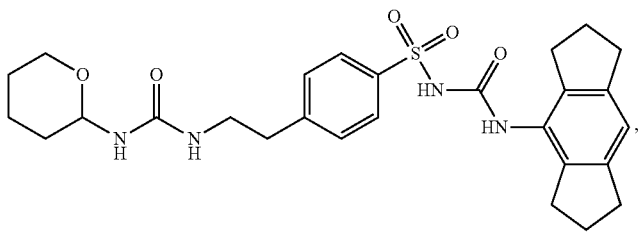

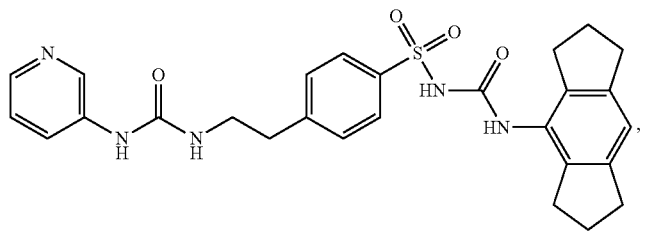
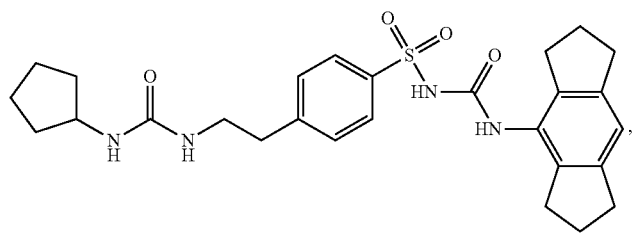
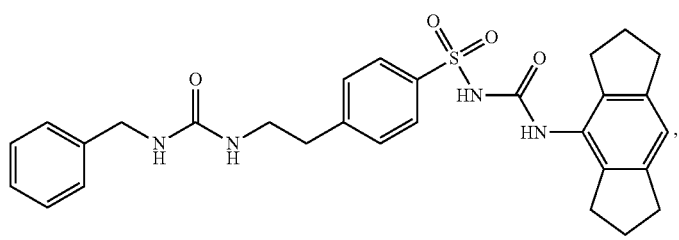
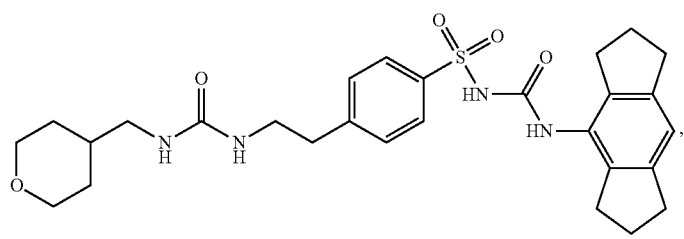
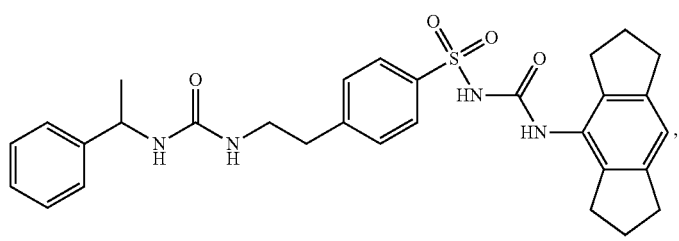
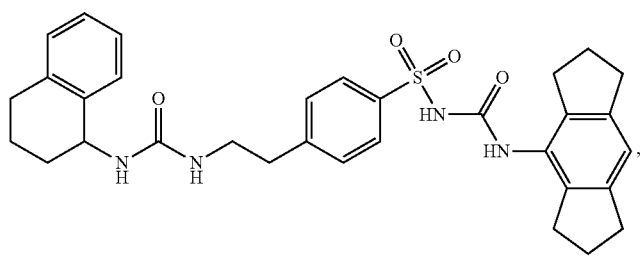
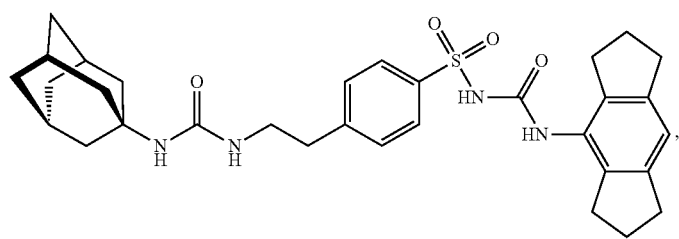

-continued

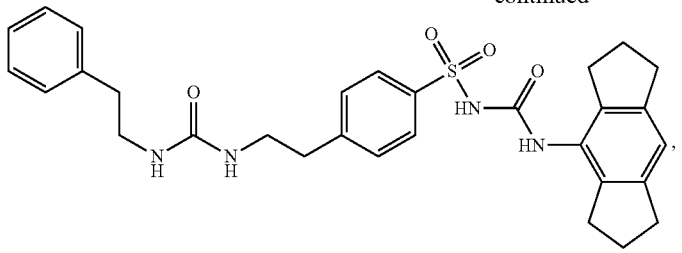

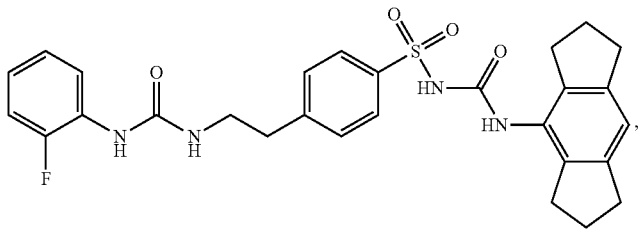

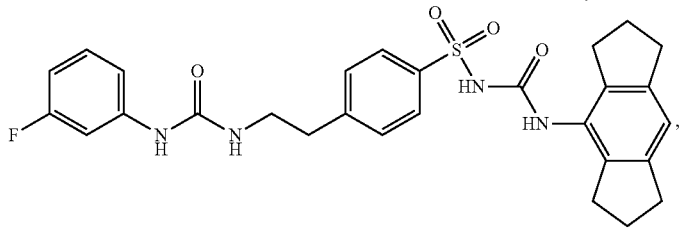

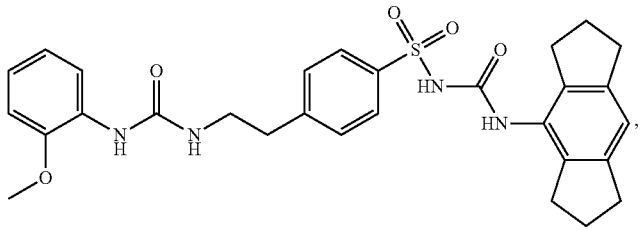

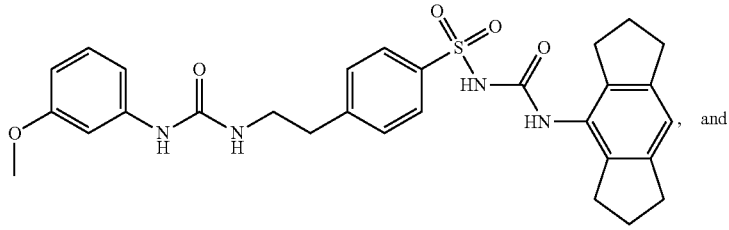, and

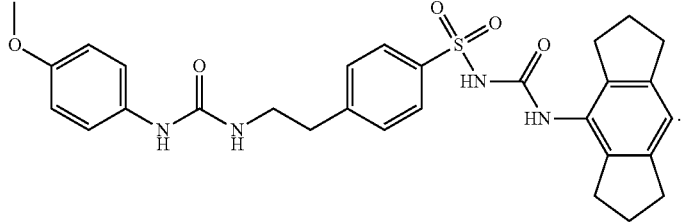.

In a different embodiment, R¹ is a heterocyclic group substituted with at least one group X, wherein R¹ may optionally be further substituted. The heterocyclic group may be a heteroaryl group. Typically, the heterocyclic group contains at least one nitrogen atom in the heterocyclic ring. In one aspect of such an embodiment, where the heterocyclic group contains at least one nitrogen atom in the heterocyclic ring, R² is a cyclic group substituted at the α and α' positions, wherein R² may optionally be further substituted. For example, R² may be an aryl or a heteroaryl group, wherein the aryl or the heteroaryl group is substituted at the α and α' positions, wherein R² may optionally be further substituted.

Typically, where the heterocyclic group contains at least one nitrogen atom in the heterocyclic ring, the heterocyclic group is a 5- or a 6-membered heteroaryl group such as an oxazolyl, thiazolyl, imidazolyl, pyrazolyl, isoxazolyl, isothiazolyl, oxadiazolyl, triazolyl, thiadiazolyl or pyridinyl group. More typically, the 5- or 6-membered heteroaryl group is an optionally further substituted 5-membered heteroaryl group, such as a 5-membered heteroaryl group containing at least two nitrogen atoms in the heterocyclic ring. Examples of such compounds include:
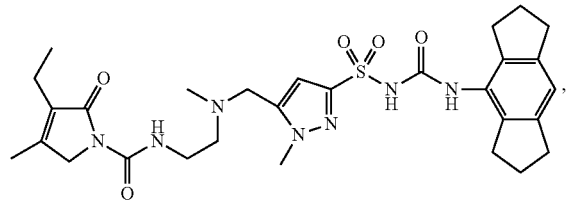
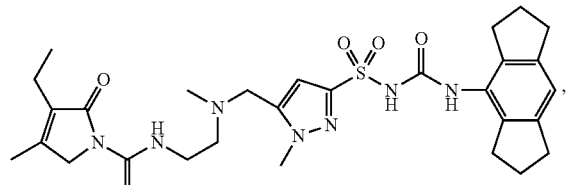
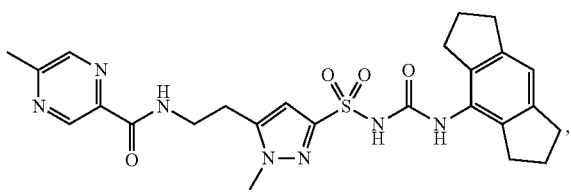
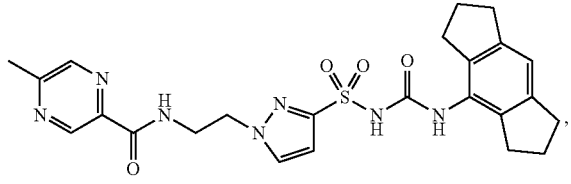
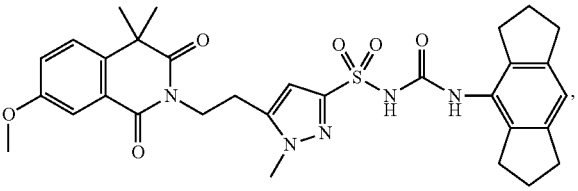
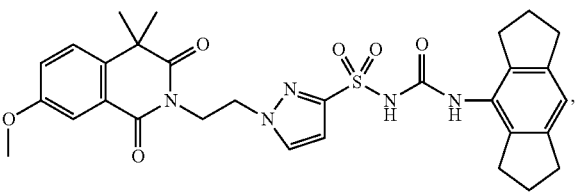
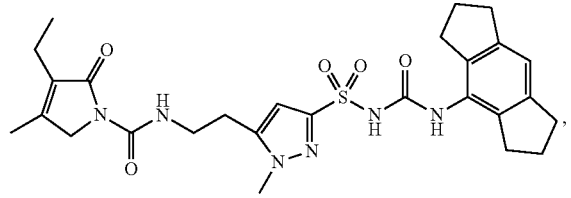
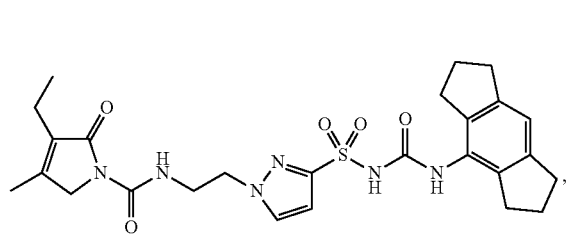
-continued
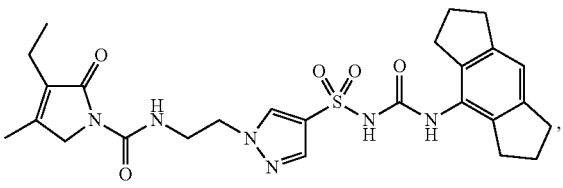
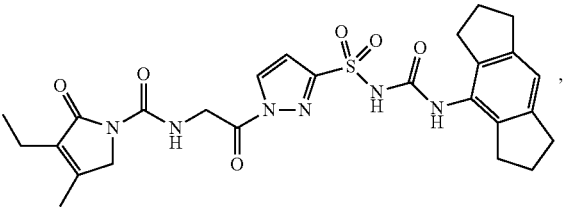
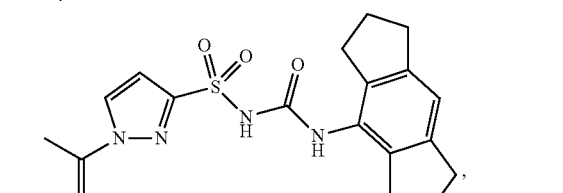
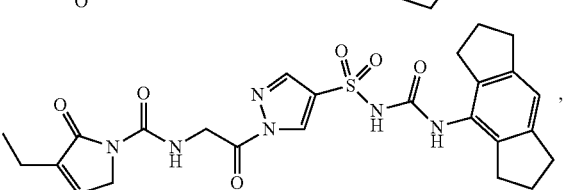
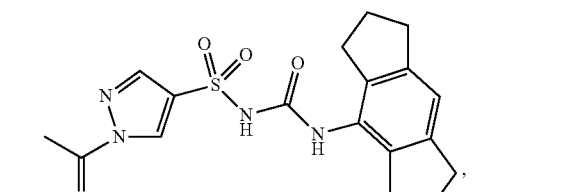
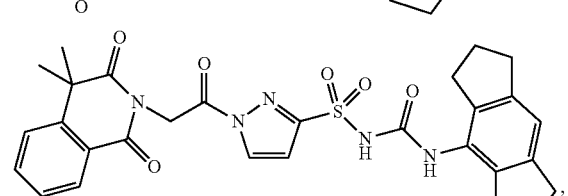
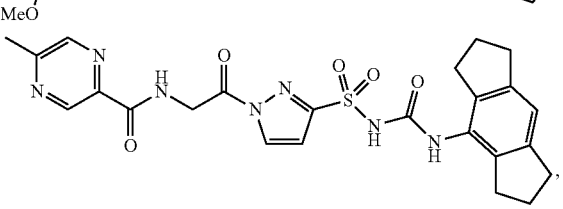
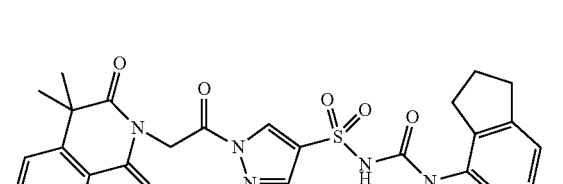

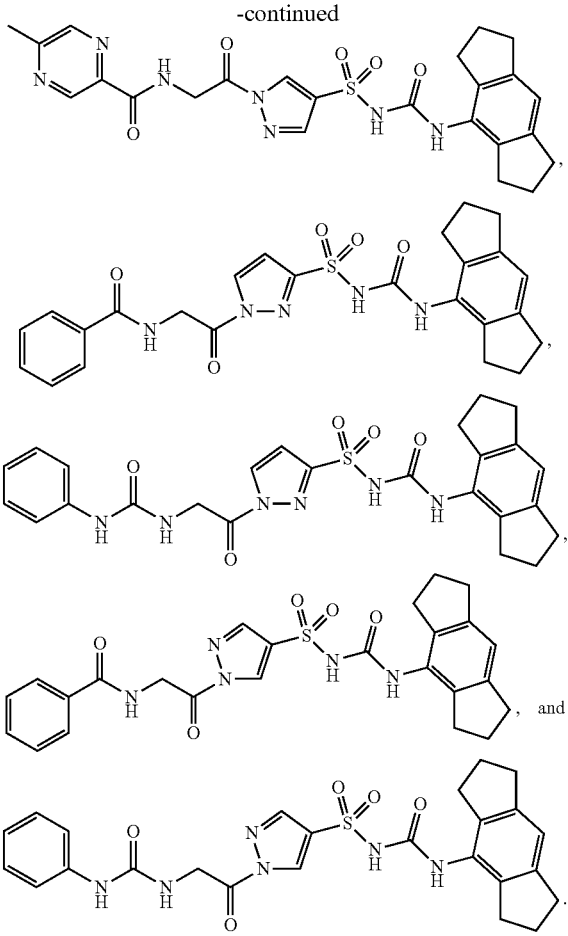

As stated above, X may be any group comprising a carbonyl group, i.e. any group comprising a C=O moiety. Accordingly, the group X may be or comprise an aldehyde, a ketone, an ester, a carboxylic acid, an amide, a urea, etc. For the avoidance of doubt, X must comprise both the carbon atom and the oxygen atom of the C=O moiety; an oxo (=O) substituent directly attached to the cyclic group of $R^1$ is not considered to be a substituent X. The group X may comprise a single carbonyl group or more than one carbonyl group. Typically, X contains from 1 to 20 carbon atoms. More typically, X contains from 2 to 15 carbon atoms. X may be saturated or unsaturated.

Unless stated otherwise, X may be a monovalent substituent or a divalent or multivalent substituent. Where X is a divalent or multivalent substituent, X may be attached to the cyclic group of $R^1$ via a double bond and/or as a spiro or a fused ring structure. Typically, X is a monovalent substituent.

In one embodiment, X— is:

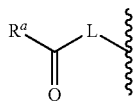

wherein:
L is a bond or an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S;

$R^a$ is selected from hydrogen or an alkyl, alkenyl, alkynyl, Z—, Z-alkylene-, Z-alkenylene- or Z-alkynylene- group, wherein one or more carbon atoms in the backbone of the alkyl, alkenyl, alkynyl, alkylene, alkenylene or alkynylene group may optionally be replaced by one or more heteroatoms N, O or S, wherein each Z— is a cyclic group such as a cycloalkyl, cycloalkenyl, non-aromatic heterocyclic, aryl or heteroaryl group; and wherein X may optionally be substituted.

In another embodiment, X— is:

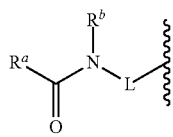

wherein:
L is a bond or an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted;

$R^a$ and $R^b$ together with the atoms to which they are attached may form a cyclic group, or $R^a$ and $R^b$ are each independently selected from hydrogen or an alkyl, alkenyl, alkynyl, Z—, Z-alkylene-, Z-alkenylene- or Z-alkynylene-group, wherein one or more carbon atoms in the backbone of the alkyl, alkenyl, alkynyl, alkylene, alkenylene or alkynylene group may optionally be replaced by one or more heteroatoms N, O or S, wherein each Z— is a cyclic group; and wherein any $R^a$ and $R^b$ may optionally be substituted.

Examples of such groups X include:

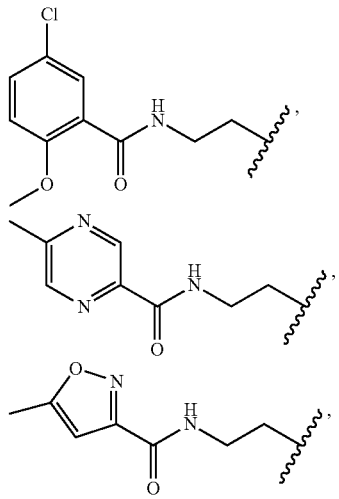

43
-continued
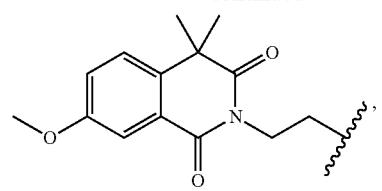
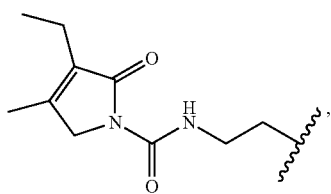
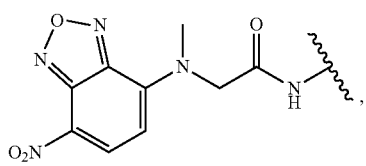
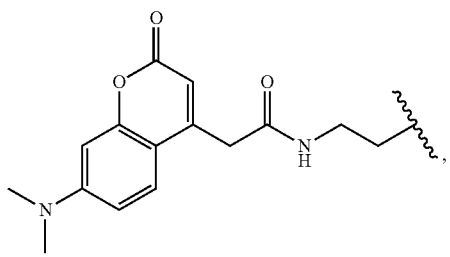
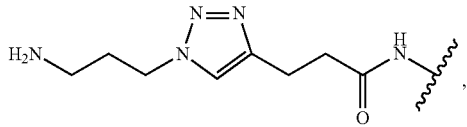
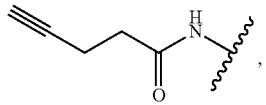
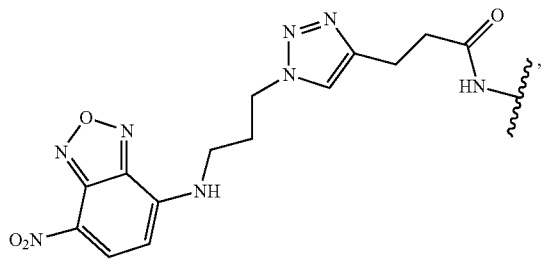
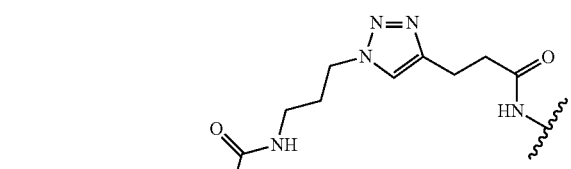
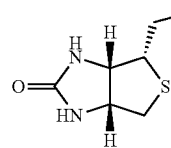
44
-continued
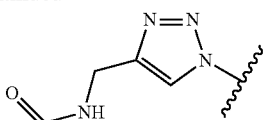
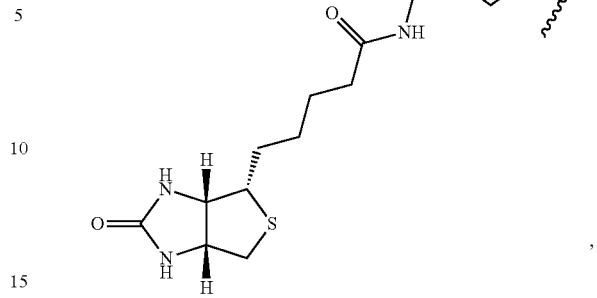
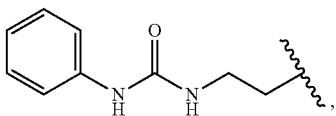
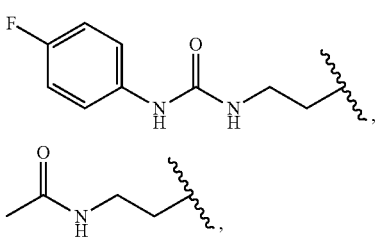
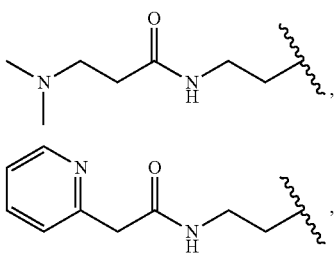
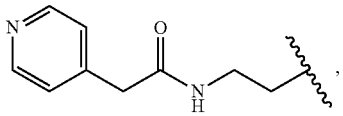
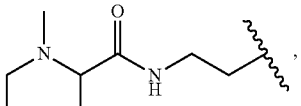
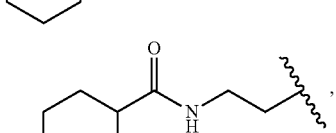
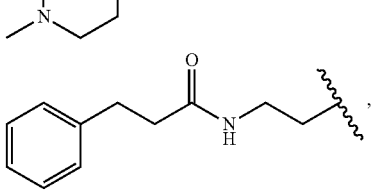
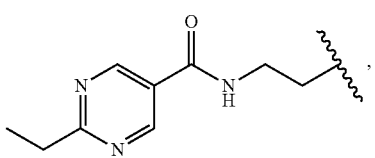

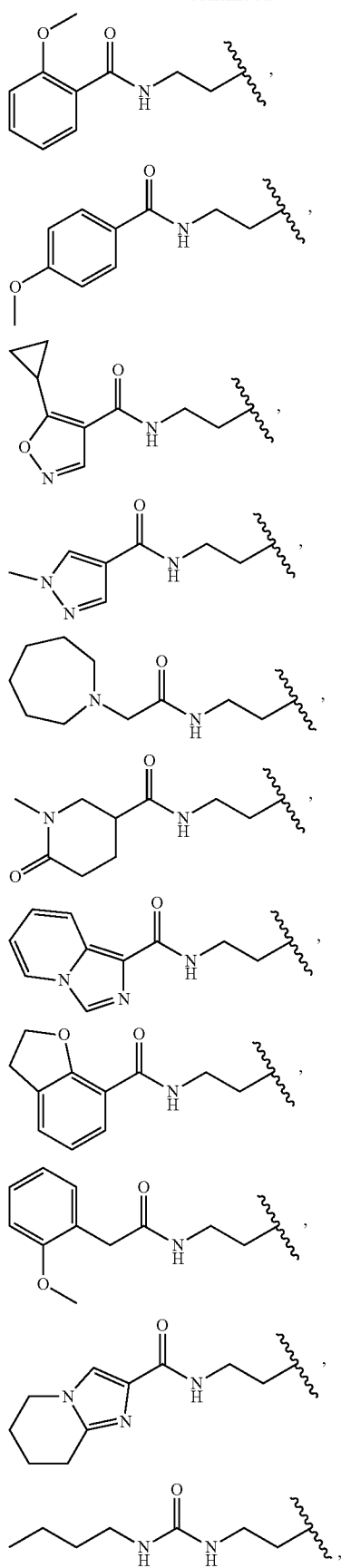
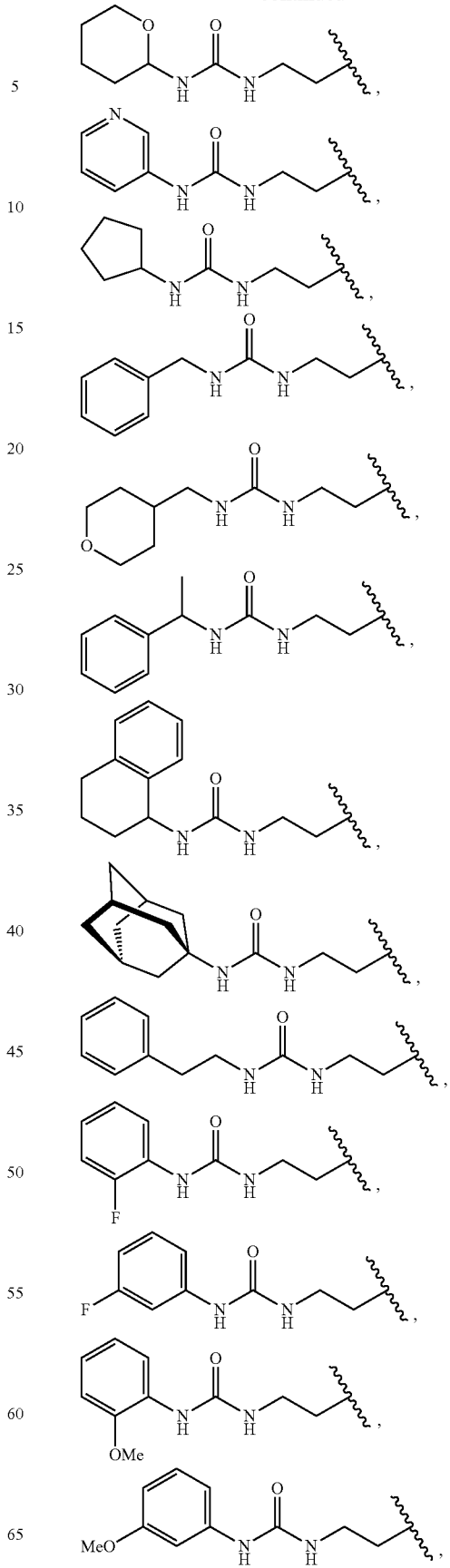

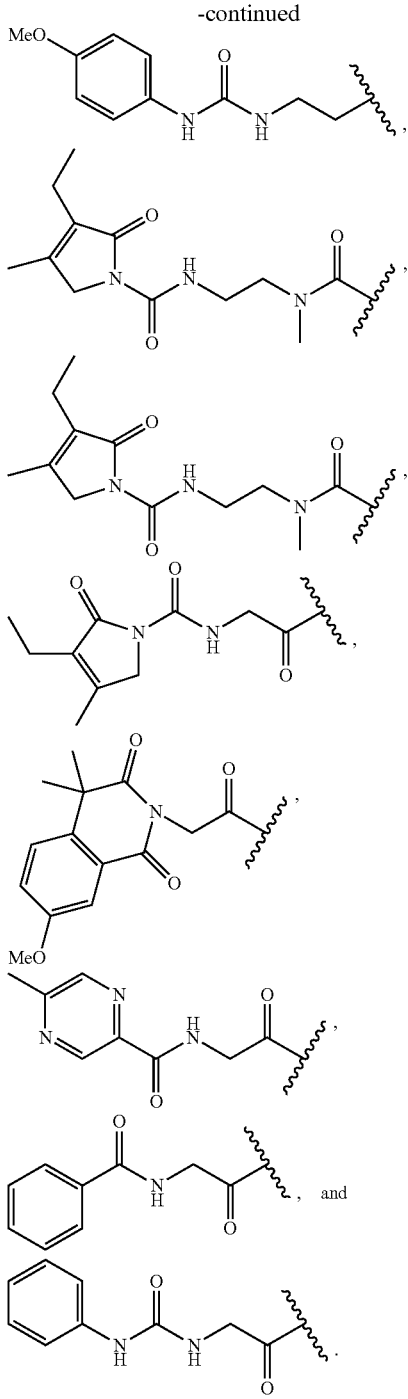

Typically when X— is

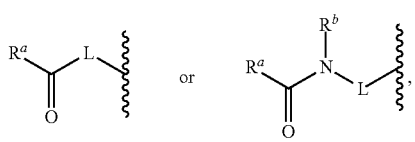

$R^2$ is an aryl or a heteroaryl group, wherein the aryl or the heteroaryl group is substituted at the α-position and wherein $R^2$ may optionally be further substituted.

Typically, L is an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted. Typically, where the alkylene, alkenylene or alkynylene group is optionally substituted, it is substituted with one or more monovalent substituents and/or oxo (═O) groups.

As will be appreciated, if the alkylene, alkenylene or alkynylene group of L contains a single carbon atom which is replaced by a heteroatom N, O or S, the resultant group L may be —NH—, —O— or —S—. Typically however, where X— is:

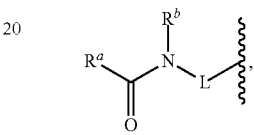

the N-L bond is not an N—N, N—O or N—S bond.

In one embodiment, L is an alkylene or alkenylene group, wherein the alkylene or alkenylene group is linear and contains from 2 to 4 atoms in its backbone, wherein one or more carbon atoms in the backbone of the alkylene or alkenylene group may optionally be replaced by one or more heteroatoms N, O or S, with the proviso that the N-L bond is not an N—N, N—O or N—S bond, and wherein the alkylene or alkenylene group may optionally be substituted. Typically, such an alkylene or alkenylene group is unsubstituted or optionally substituted with one or more groups independently selected from halo, methyl, methoxy, halomethyl, halomethoxy and oxo groups.

In one embodiment, L is —$(CH_2)_x$— wherein x is 1, 2, 3, 4, 5 or 6. More typically, x is 2, 3 or 4. Most typically, x is 2.

Typically, $R^a$ (including any optional substitution) contains from 1 to 12 carbon atoms. More typically, $R^a$ (including any optional substitution) contains from 3 to 10 carbon atoms.

In one embodiment, $R^a$ is selected from an alkyl, Z- or Z-alkylene-group, wherein one or more carbon atoms in the backbone of the alkyl or alkylene group may optionally be replaced by one or more heteroatoms N, O or S, wherein each Z— is a 5 to 14 membered monocyclic, bicyclic or tricyclic group, and wherein $R^a$ may optionally be substituted with one or more halo, oxo, $C_1$-$C_4$ alkyl, $C_3$-$C_4$ cycloalkyl or $C_2$-$C_4$ alkenyl groups, wherein one or more carbon atoms in the backbone of any of the $C_1$-$C_4$ alkyl, $C_3$-$C_4$ cycloalkyl or $C_2$-$C_4$ alkenyl groups may optionally be replaced by one or more heteroatoms N, O or S, and wherein any of the $C_1$-$C_4$ alkyl, $C_3$-$C_4$ cycloalkyl and $C_2$-$C_4$ alkenyl groups may be optionally substituted with one or more halo and/or oxo groups.

Typically in the above embodiment, $R^a$ is selected from a Z- or Z-alkylene-group, wherein one or more carbon atoms in the backbone of the alkylene group may optionally be replaced by one or more heteroatoms N, O or S, wherein each Z— is a 5 to 7 membered monocyclic or a 7 to 10 membered fused bicyclic group, wherein each Z— may optionally be substituted with one or more halo, oxo, $C_1$-$C_4$ alkyl, $C_3$-$C_4$ cycloalkyl, $C_2$-$C_4$ alkenyl, —O—($C_1$-$C_4$ alkyl), —O—(C$_3$-C$_4$ cycloalkyl) or —O—(C$_2$-C$_4$ alkenyl) groups, wherein any of the C$_1$-C$_4$ alkyl, C$_3$-C$_4$ cycloalkyl, C$_2$-C$_4$ alkenyl, —O—(C$_1$-C$_4$ alkyl), —O—(C$_3$-C$_4$ cycloalkyl) or —O—(C$_2$-C$_4$ alkenyl) groups may be optionally substituted with one or more halo groups.

Typically, the alkylene group of Z-alkylene contains from 1 to 3 atoms in its backbone. Optionally, where the alkylene group of Z-alkylene contains from 1 to 3 atoms in its backbone, one carbon atom in the backbone may be replaced by a heteroatom N. Examples of such alkylene groups include —CH$_2$—, —NH—, —CH(Me)-, —N(Me)-, —CH$_2$CH$_2$—, —NHCH$_2$—, —CH$_2$NH—, —CH$_2$CH$_2$CH$_2$—, —CH$_2$CH$_2$NH—, —NHCH$_2$CH$_2$—, —CH$_2$NHCH$_2$—, —CH(Me)CH$_2$—, —CH$_2$CH(Me)-, —N(Me)CH$_2$—, —NHCH(Me)-, —CH(Me)NH—, —CH$_2$N(Me)- and —C(Me)$_2$-.

In one embodiment, R$^b$ is selected from hydrogen or a —R$^c$, —COOR$^c$ or —COR$^c$ group, wherein R$^c$ is selected from a C$_1$-C$_{10}$ alkyl, C$_2$-C$_{10}$ alkenyl, C$_2$-C$_{10}$ alkynyl, C$_2$-C$_{10}$ cyclic or —(CH$_2$)$_y$—(C$_2$-C$_{10}$ cyclic) group wherein y is 1, 2, 3 or 4, and wherein each R$^c$ is optionally further substituted with one or more halo, hydroxyl, methyl, methoxy, halomethyl or halomethoxy groups. Optionally, R$^c$ is selected from a C$_1$-C$_6$ alkyl, C$_2$-C$_6$ alkenyl, C$_3$-C$_6$ cyclic or —CH$_2$—(C$_3$-C$_6$ cyclic) group wherein each R$^c$ is optionally further substituted with one or more chloro or fluoro groups.

Typically, R$^b$ is hydrogen.

Alternatively, where R$^a$ and R$^b$ together with the atoms to which they are attached form a cyclic group, the resultant cyclic group may be a 5 to 14 membered monocyclic, bicyclic or tricyclic group, wherein the resultant cyclic group may optionally be substituted with one or more halo, oxo, C$_1$-C$_4$ alkyl, C$_3$-C$_4$ cycloalkyl or C$_2$-C$_4$ alkenyl groups, wherein one or more carbon atoms in the backbone of any of the C$_1$-C$_4$ alkyl, C$_3$-C$_4$ cycloalkyl or C$_2$-C$_4$ alkenyl groups may optionally be replaced by one or more heteroatoms N, O or S, and wherein any of the C$_1$-C$_4$ alkyl, C$_3$-C$_4$ cycloalkyl and C$_2$-C$_4$ alkenyl groups may be optionally substituted with one or more halo and/or oxo groups.

Typically, where R$^a$ and R$^b$ together with the atoms to which they are attached form a cyclic group, the resultant cyclic group is a 5 to 7 membered monocyclic or a 7 to 10 membered fused bicyclic group, wherein the resultant cyclic group may optionally be substituted with one or more halo, oxo, C$_1$-C$_4$ alkyl, C$_3$-C$_4$ cycloalkyl, C$_2$-C$_4$ alkenyl, —O—(C$_1$-C$_4$ alkyl), —O—(C$_3$-C$_4$ cycloalkyl) or —O—(C$_2$-C$_4$ alkenyl) groups, wherein any of the C$_1$-C$_4$ alkyl, C$_3$-C$_4$ cycloalkyl, C$_2$-C$_4$ alkenyl, —O—(C$_1$-C$_4$ alkyl), —O—(C$_3$-C$_4$ cycloalkyl) or —O—(C$_2$-C$_4$ alkenyl) groups may be optionally substituted with one or more halo groups.

In one aspect of any of the above embodiments, R$^1$ is a cyclic group substituted with a single group X, wherein the cyclic group may optionally be further substituted. Where the cyclic group of R$^1$ is further substituted, typically the further substituents do not comprise a carbonyl group.

In one embodiment, R$^1$ is a cyclic group substituted with at least one group X, wherein the cyclic group of R$^1$ may optionally be further substituted with one or more groups Y, wherein each Y is independently selected from a halo, oxo, C$_1$-C$_4$ alkyl, C$_3$-C$_4$ cycloalkyl or C$_2$-C$_4$ alkenyl group, wherein one or more carbon atoms in the backbone of any of the C$_1$-C$_4$ alkyl, C$_3$-C$_4$ cycloalkyl or C$_2$-C$_4$ alkenyl groups may optionally be replaced by one or more heteroatoms N, O or S, and wherein any of the C$_1$-C$_4$ alkyl, C$_3$-C$_4$ cycloalkyl and C$_2$-C$_4$ alkenyl groups may be optionally substituted with one or more halo and/or oxo groups. Typically, R$^1$ is a cyclic group substituted with a single group X, wherein the cyclic group of R$^1$ may optionally be further substituted with one or two groups Y, wherein each Y is independently selected from a fluoro, chloro, oxo, methyl, ethyl, methoxy or ethoxy group, wherein each methyl, ethyl, methoxy or ethoxy group may optionally be substituted with one or more chloro or fluoro groups. More typically, R$^1$ is a cyclic group substituted with a single group X, wherein the cyclic group of R$^1$ is not further substituted.

In one aspect of any of the above embodiments, the compound of formula (I) has a molecular weight of from 200 to 2000 Da. Typically, the compound of formula (I) has a molecular weight of from 350 to 800 Da. More typically, the compound of formula (I) has a molecular weight of from 450 to 650 Da.

A second aspect of the invention relates to a compound selected from the group consisting of:

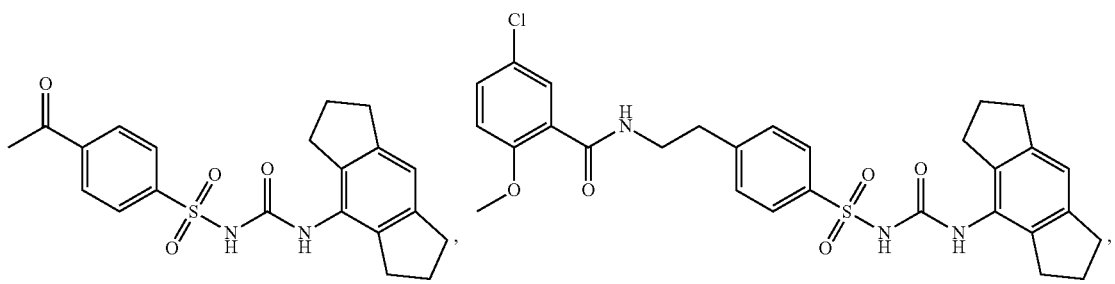

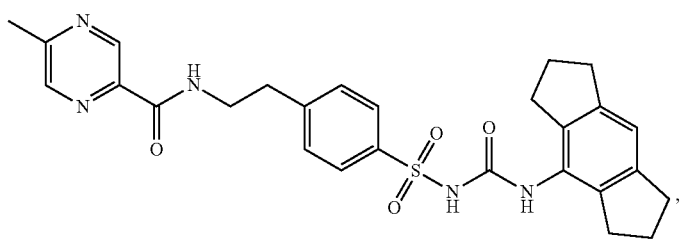

-continued
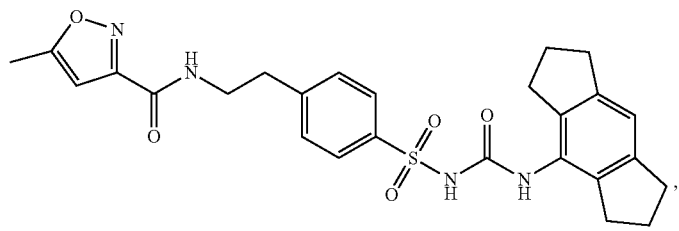
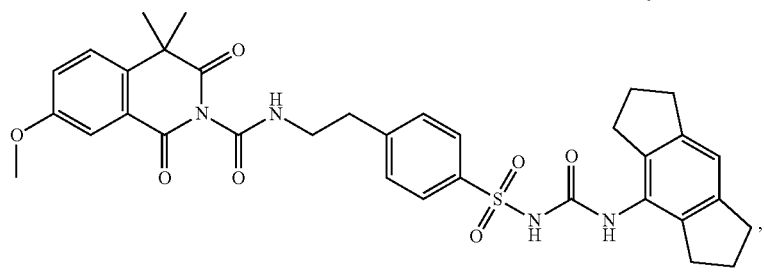
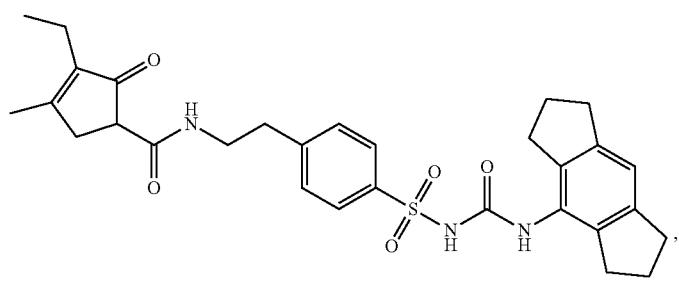
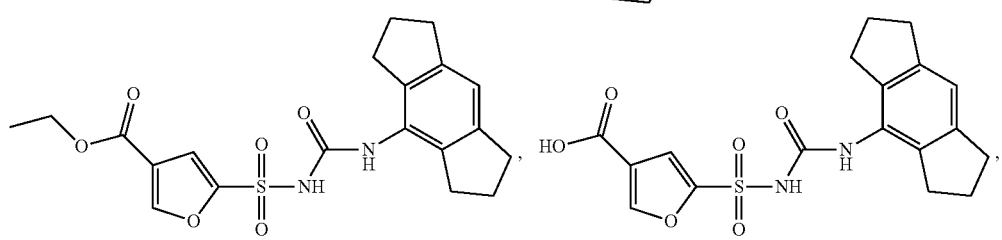
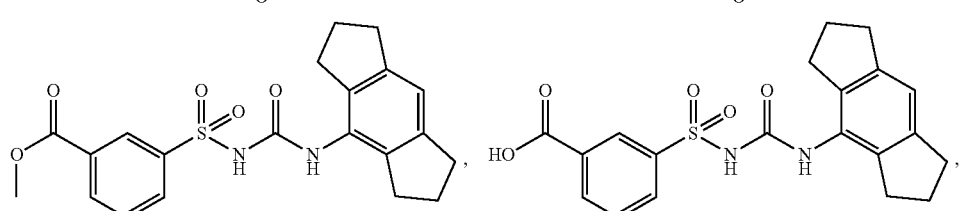
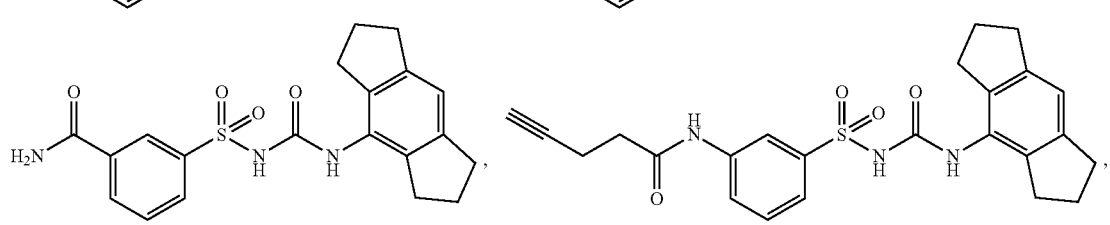
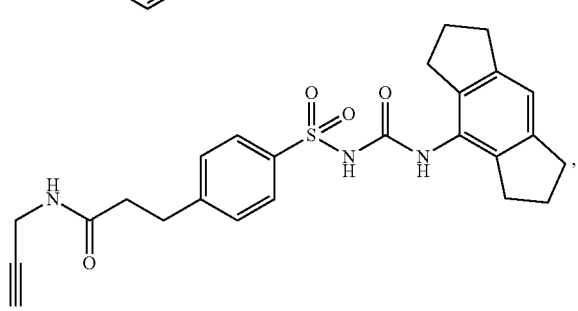

-continued
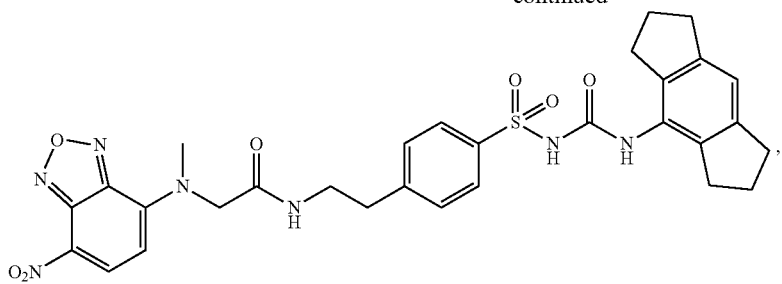
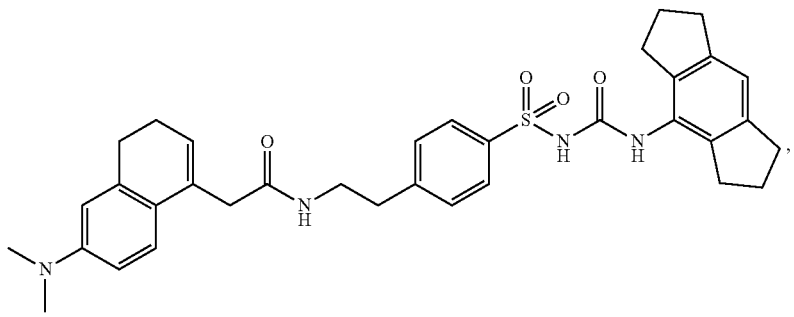
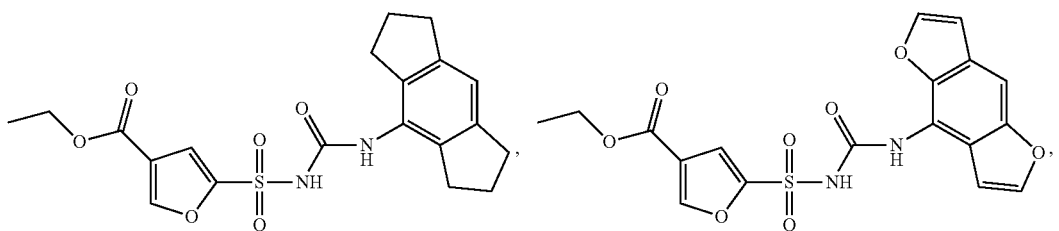
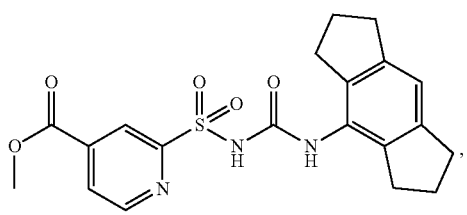
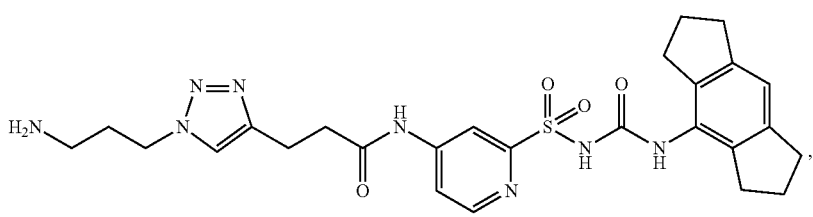
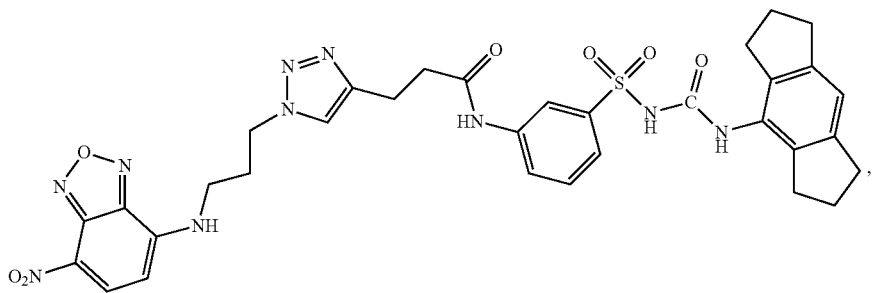

-continued
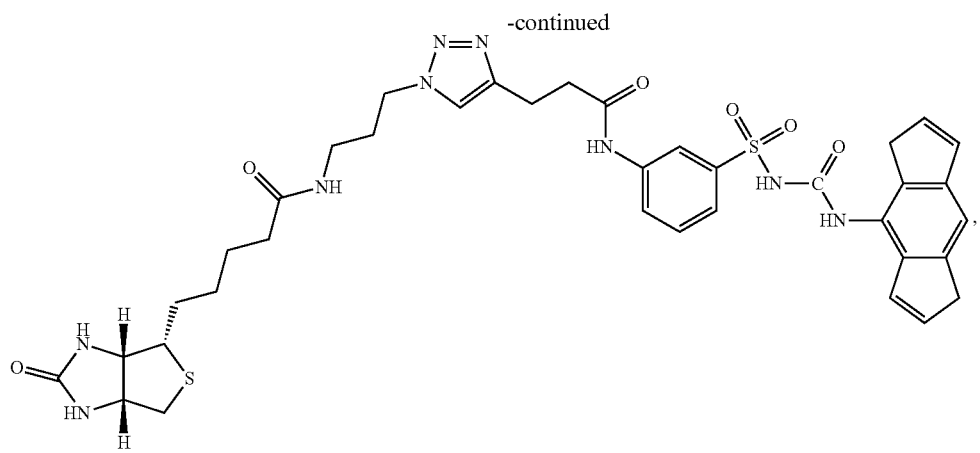
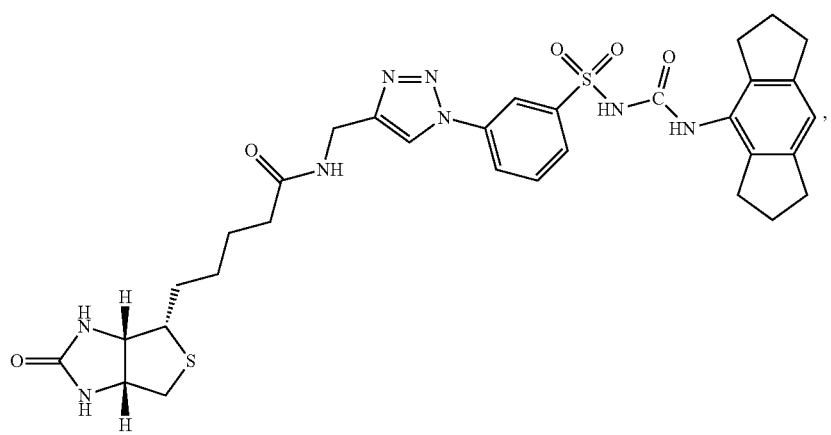
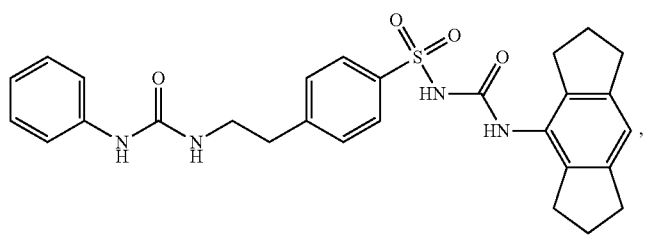
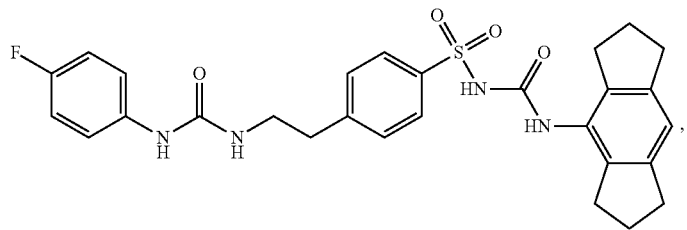
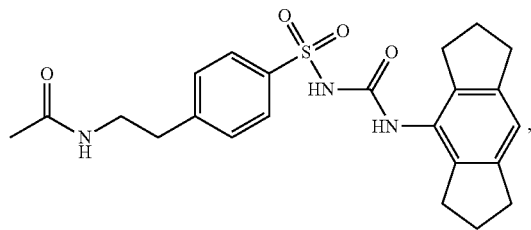

-continued
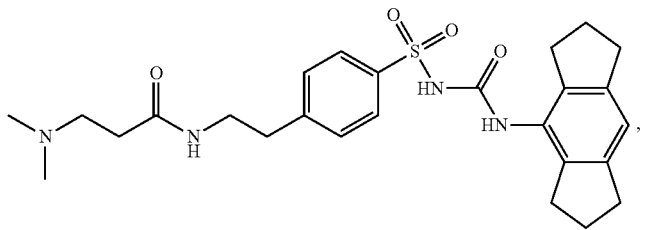,
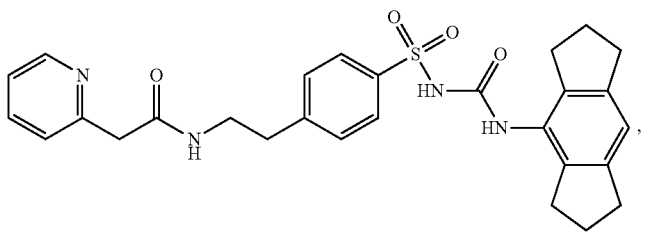,
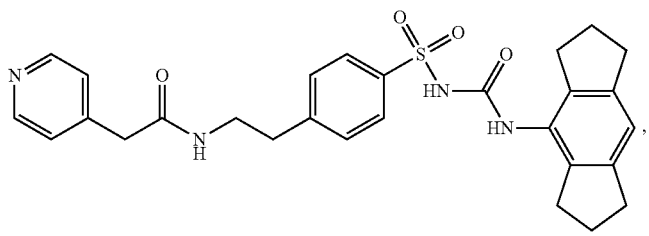,
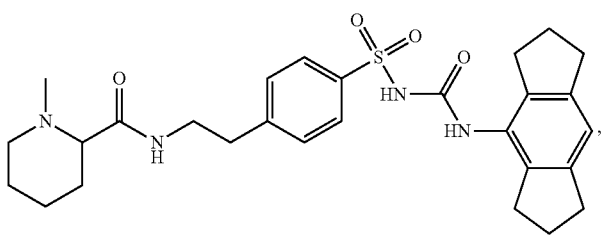,
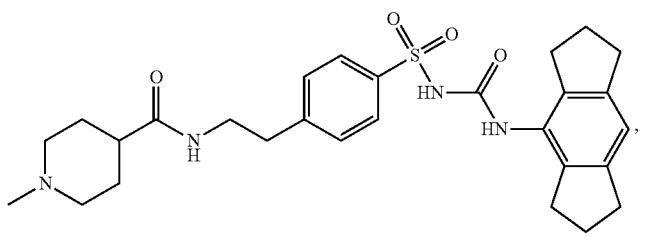,
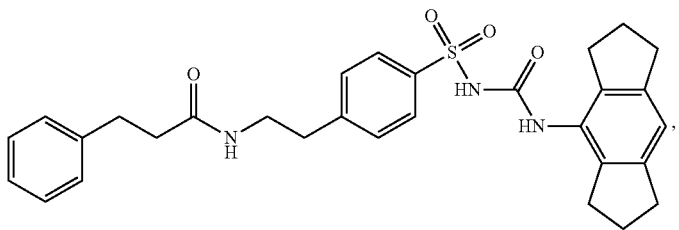,
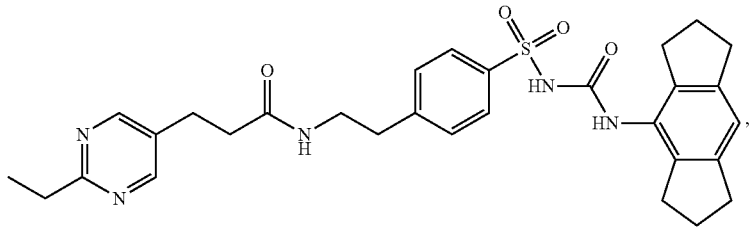, -continued
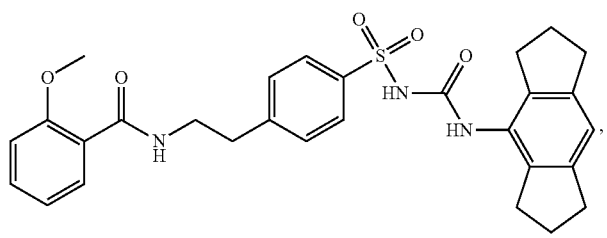
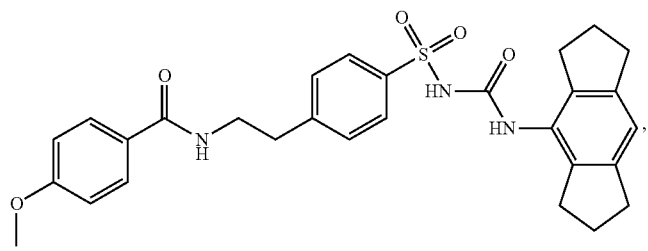
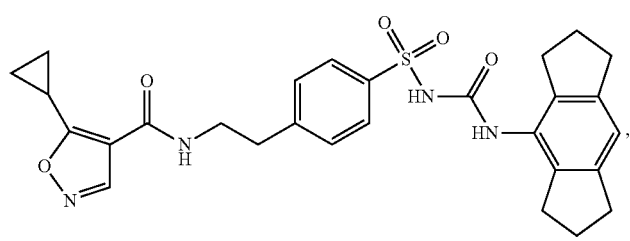
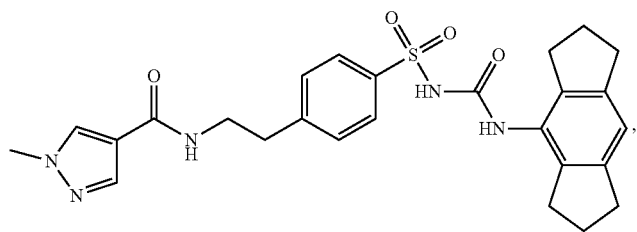
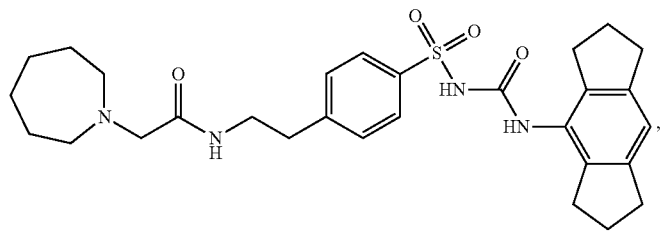
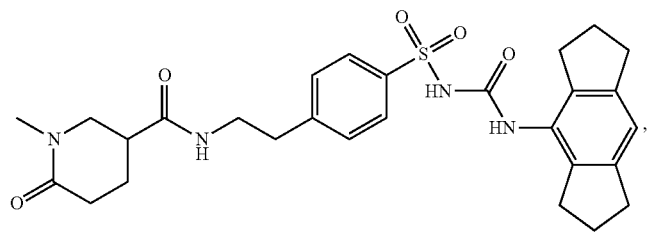
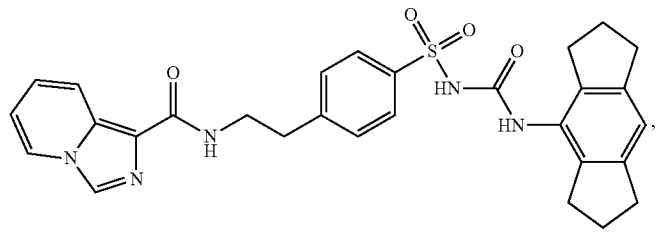

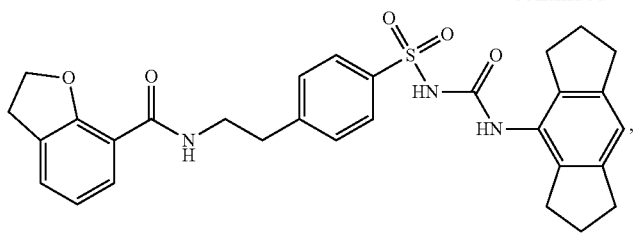
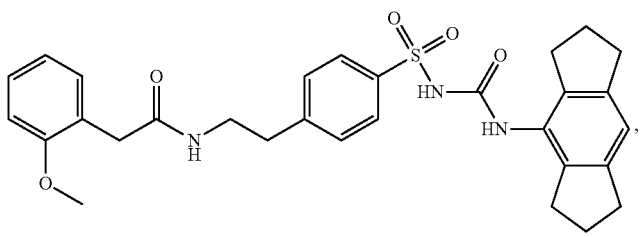
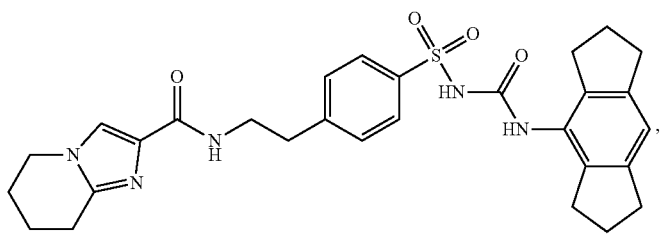
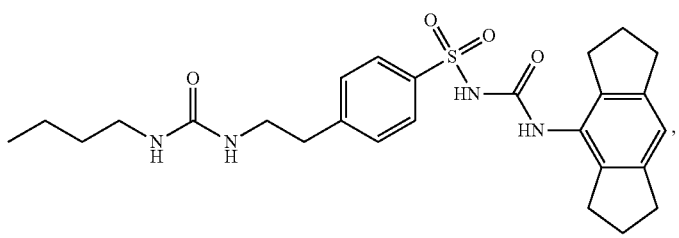
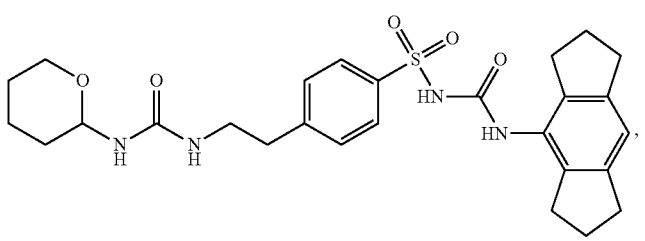
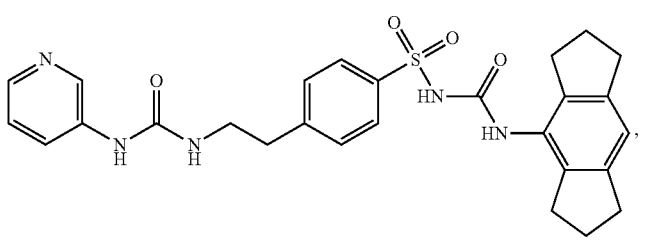
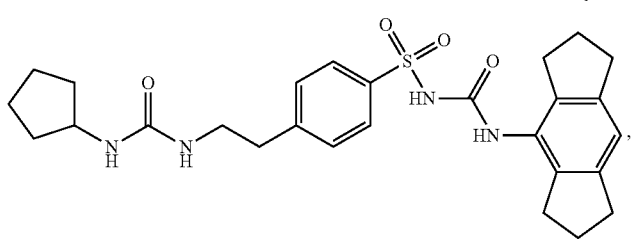

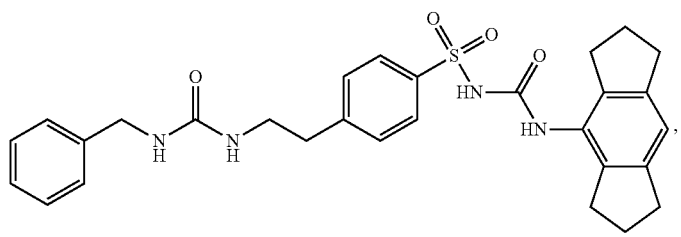
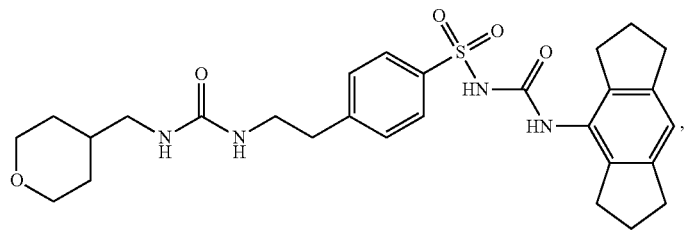
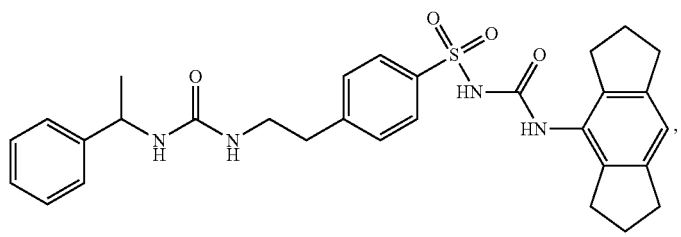
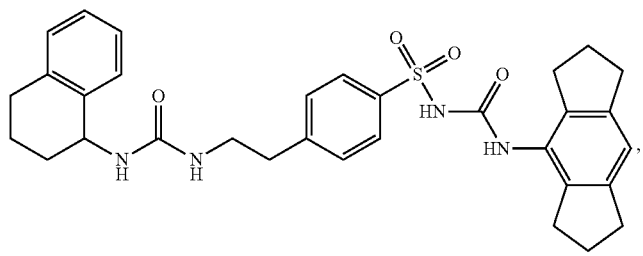
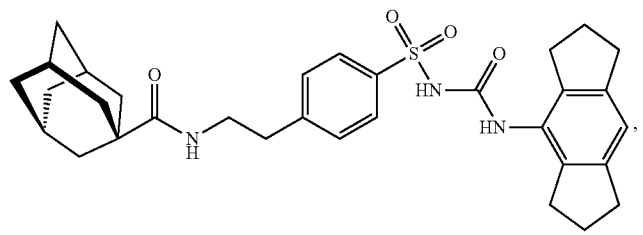
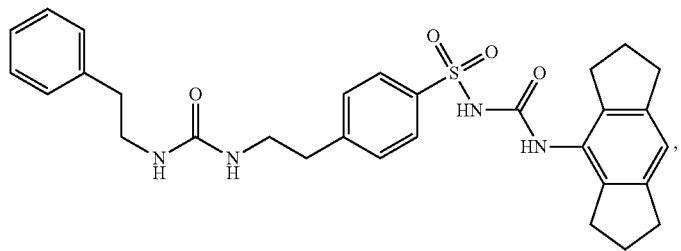
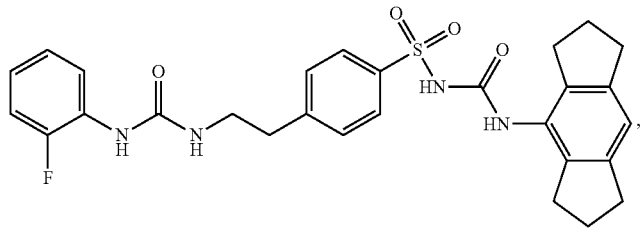

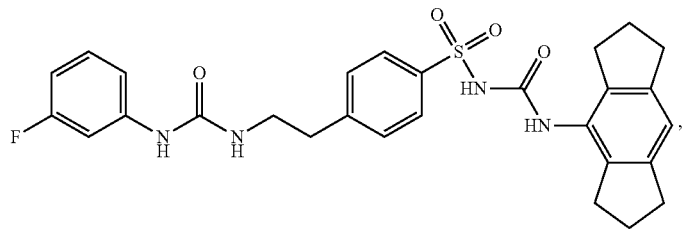
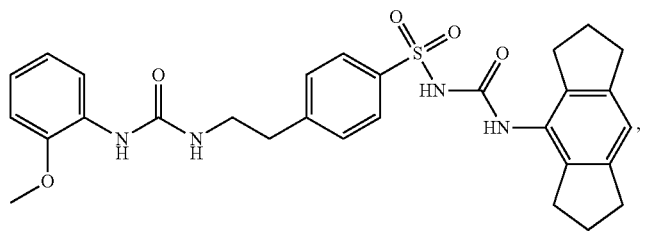
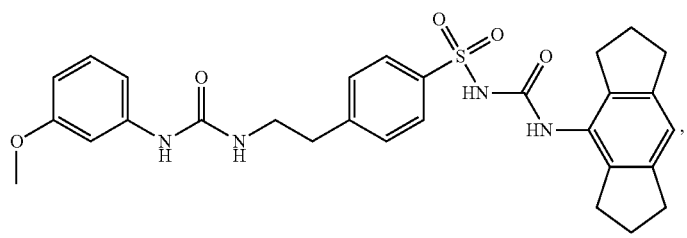
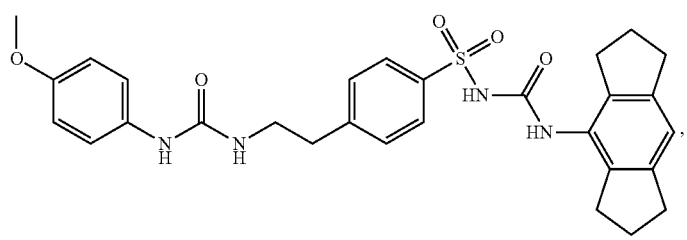
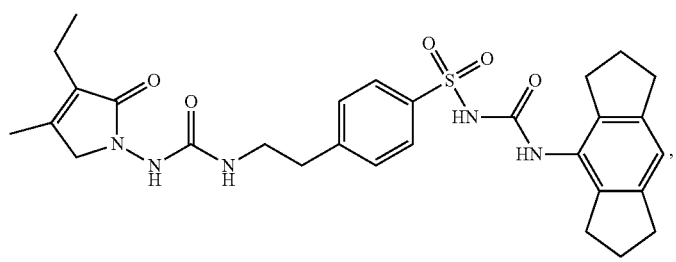
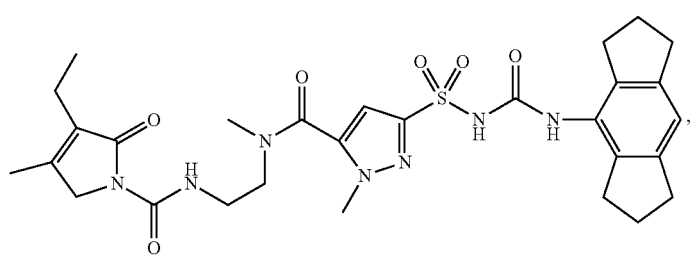
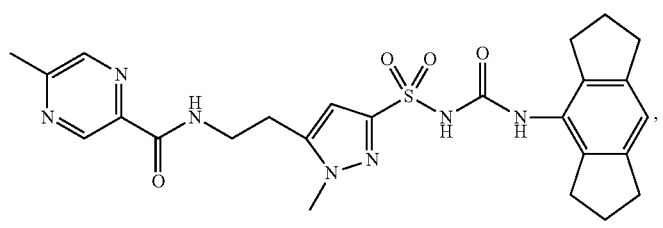

-continued
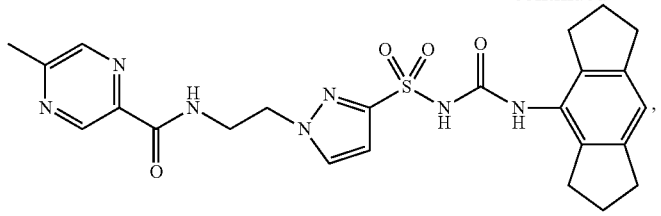
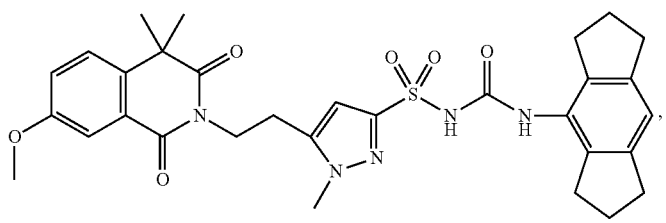
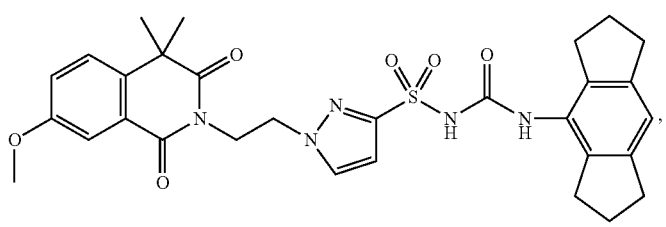
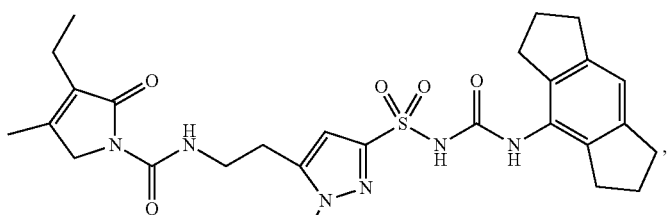
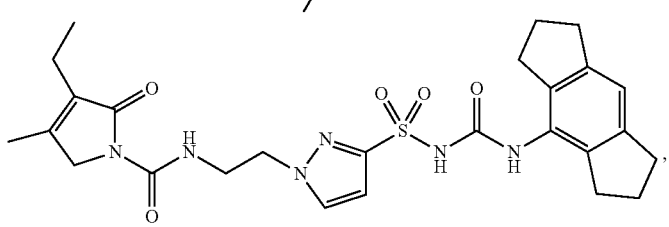
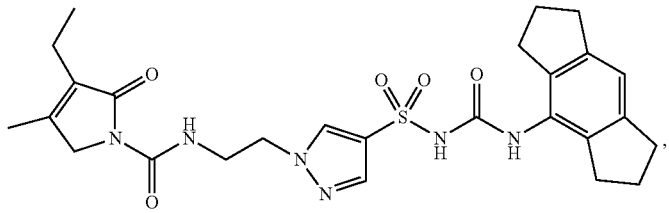
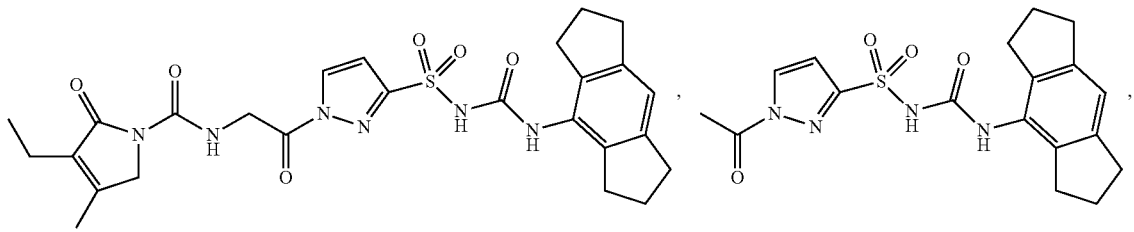

69 70
-continued
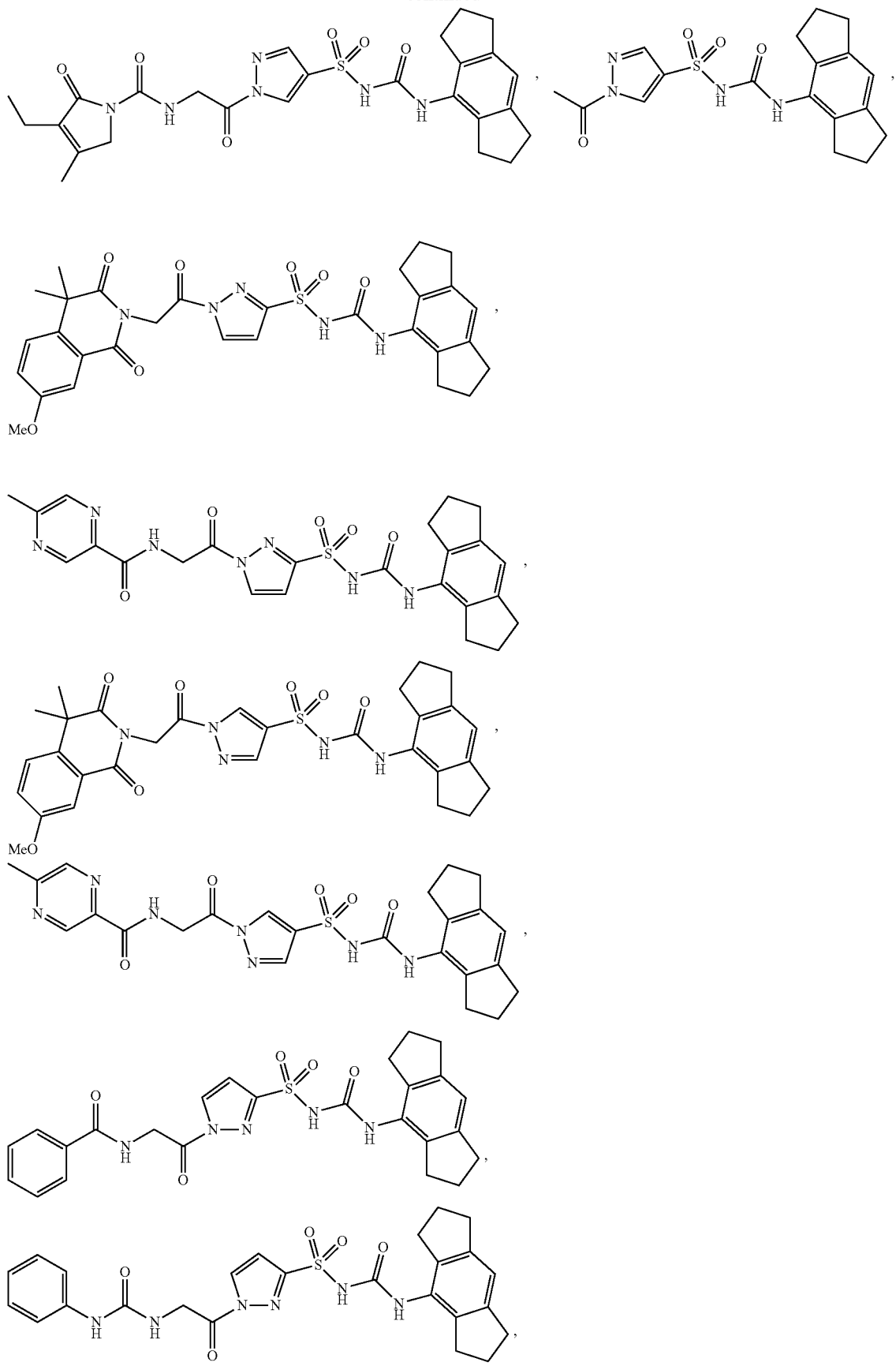

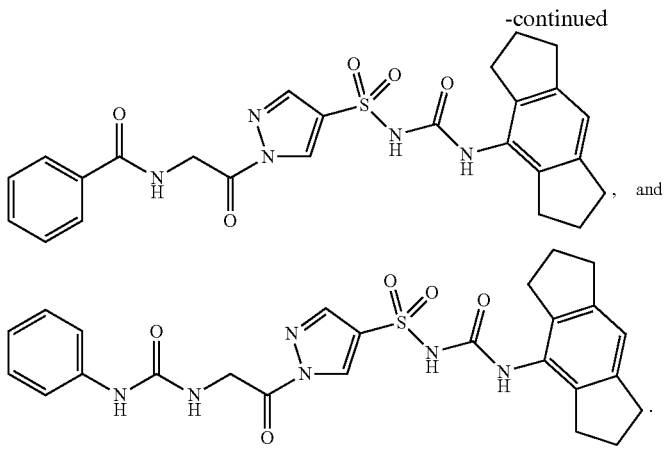
, and

A third aspect of the invention relates to a pharmaceutically acceptable salt, solvate or prodrug of any compound of the first or second aspect of the invention.

The compounds of the present invention can be used both in their free base form and their acid addition salt form. For the purposes of this invention, a "salt" of a compound of the present invention includes an acid addition salt. Acid addition salts are preferably pharmaceutically acceptable, non-toxic addition salts with suitable acids, including but not limited to inorganic acids such as hydrohalogenic acids (for example, hydrofluoric, hydrochloric, hydrobromic or hydroiodic acid) or other inorganic acids (for example, nitric, perchloric, sulphuric or phosphoric acid); or organic acids such as organic carboxylic acids (for example, propionic, butyric, glycolic, lactic, mandelic, citric, acetic, benzoic, salicylic, succinic, malic or hydroxysuccinic, tartaric, fumaric, maleic, hydroxymaleic, mucic or galactaric, gluconic, pantothenic or pamoic acid), organic sulphonic acids (for example, methanesulphonic, trifluoromethanesulphonic, ethanesulphonic, 2-hydroxyethanesulphonic, benzenesulphonic, toluene-p-sulphonic, naphthalene-2-sulphonic or camphorsulphonic acid) or amino acids (for example, ornithinic, glutamic or aspartic acid). The acid addition salt may be a mono-, di-, tri- or multi-acid addition salt. A preferred salt is a hydrohalogenic, sulphuric, phosphoric or organic acid addition salt. A more preferred salt is a hydrochloric acid addition salt.

The compounds of the present invention can also be used both, in their free acid form and their salt form. For the purposes of this invention, a "salt" of a compound of the present invention includes one formed between a protic acid functionality (such as a carboxylic acid group) of a compound of the present invention and a suitable cation. Suitable cations include, but are not limited to lithium, sodium, potassium, magnesium, calcium and ammonium. The salt may be a mono-, di-, tri- or multi-salt. Preferably the salt is a mono- or di-lithium, sodium, potassium, magnesium, calcium or ammonium salt. More preferably the salt is a mono- or di-sodium salt. Preferably the salt is a pharmaceutically acceptable non-toxic salt.

In addition to pharmaceutically acceptable salts, other salts are included in the present invention, since they have potential to serve as intermediates in the purification or preparation of other, for example, pharmaceutically acceptable salts, or are useful for identification, characterisation or purification of the free acid or base.

The compounds and/or salts of the present invention may be anhydrous or in the form of a hydrate (e.g. a hemihydrate, monohydrate, dihydrate or trihydrate) or other solvate. Such solvates may be formed with common organic solvents, including but not limited to, alcoholic solvents e.g. methanol, ethanol or isopropanol.

In some embodiments of the present invention, therapeutically inactive prodrugs are provided. Prodrugs are compounds which, when administered to a subject such as a human, are converted in whole or in part to a compound of the invention. In most embodiments, the prodrugs are pharmacologically inert chemical derivatives that can be converted in vivo to the active drug molecules to exert a therapeutic effect. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound.

Prodrugs include, but are not limited to, compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound. The present invention also encompasses salts and solvates of such prodrugs as described above.

The compounds, salts, solvates and prodrugs of the present invention may contain at least one chiral centre. The compounds, salts, solvates and prodrugs may therefore exist in at least two isomeric forms. The present invention encompasses racemic mixtures of the compounds, salts, solvates and prodrugs of the present invention as well as enantiomerically enriched and substantially enantiomerically pure isomers. For the purposes of this invention, a "substantially enantiomerically pure" isomer of a compound comprises less than 5% of other isomers of the same compound, more typically less than 2%, and most typically less than 0.5%.

The compounds, salts, solvates and prodrugs of the present invention may be in any polymorphic or amorphous form.

A fourth aspect of the invention relates to a pharmaceutical composition comprising a compound of the first or second aspect of the invention, or a pharmaceutically acceptable salt, solvate or prodrug of the third aspect of the invention, and a pharmaceutically acceptable excipient.

Conventional procedures for the selection and preparation of suitable pharmaceutical formulations are described in, for example, "Aulton's Pharmaceutics—The Design and Manufacture of Medicines", M. E. Aulton and K. M. G. Taylor, Churchill Livingstone Elsevier, 4$^{th}$ Ed., 2013.

Pharmaceutically acceptable excipients including adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins such as human serum albumin, buffer substances such as phosphates, glycerine, sorbic acid, potassium sorbate, partial glyceride mixtures of saturated vegetable fatty acids, water, salts or electrolytes such as protamine sulphate, disodium hydrogen phosphate, potassium hydrogen phosphate, sodium chloride, zinc salts, colloidal silica, magnesium trisilicate, polyvinylpyrrolidone, cellulose-based substances, polyethylene glycol, sodium carboxymethylcellulose, polyacrylates, waxes, polyethylene-polyoxypropylene-block polymers, polyethylene glycol and wool fat.

A fifth aspect of the invention provides a method of treatment or prevention of a disease, disorder or condition, the method comprising the step of administering an effective amount of a compound of the first or second aspect, or a pharmaceutically acceptable salt, solvate or prodrug of the third aspect, or a pharmaceutical composition of the fourth aspect, to thereby treat or prevent the disease, disorder or condition. Typically the administration is to a subject in need thereof.

The term "treatment" as used herein refers equally to curative therapy, and ameliorating or palliative therapy. The term includes obtaining beneficial or desired physiological results, which may or may not be established clinically. Beneficial or desired clinical results include, but are not limited to, the alleviation of symptoms, the prevention of symptoms, the diminishment of extent of disease, the stabilisation (i.e., not worsening) of a condition, the delay or slowing of progression/worsening of a condition/symptoms, the amelioration or palliation of the condition/symptoms, and remission (whether partial or total), whether detectable or undetectable. The term "palliation", and variations thereof, as used herein, means that the extent and/or undesirable manifestations of a physiological condition or symptom are lessened and/or time course of the progression is slowed or lengthened, as compared to not administering a compound, salt, solvate, prodrug or pharmaceutical composition of the present invention. The term "prevention" as used herein in relation to a disease, disorder or condition, relates to prophylactic or preventative therapy, as well as therapy to reduce the risk of developing the disease, disorder or condition. The term "prevention" includes both the avoidance of occurrence of the disease, disorder or condition, and the delay in onset of the disease, disorder or condition. Any statistically significant ($p \leq 0.05$) avoidance of occurrence, delay in onset or reduction in risk as measured by a controlled clinical trial may be deemed a prevention of the disease, disorder or condition. Subjects amenable to prevention include those at heightened risk of a disease, disorder or condition as identified by genetic or biochemical markers. Typically, the genetic or biochemical markers are appropriate to the disease, disorder or condition under consideration and include for example, inflammatory biomarkers such as C-reactive protein (CRP) and monocyte chemoattractant protein 1 (MCP-1) in the case of inflammation; blood glucose levels and glycated haemoglobin (HbA1c) in the case of diabetes; and total cholesterol, triglycerides, insulin resistance and C-peptide in the case of NAFLD and NASH.

A sixth aspect of the invention provides for a compound of the first aspect or second aspect, or a pharmaceutically acceptable salt, solvate or prodrug of the third aspect, or a pharmaceutical composition of the fourth aspect, for use as a medicament and/or for use in the treatment or prevention of a disease, disorder or condition. Typically the use comprises the administration of the compound, salt, solvate, prodrug or pharmaceutical composition to a subject.

A seventh aspect of the invention provides for the use of a compound of the first or second aspect, or a pharmaceutically effective salt, solvate or prodrug of the third aspect, in the manufacture of a medicament for the treatment or prevention of a disease, disorder or condition. Typically the treatment or prevention comprises the administration of the compound, salt, solvate, prodrug or pharmaceutical composition to a subject.

In general embodiments, the disease, disorder or condition may be a disease, disorder or condition of the immune system, the cardiovascular system, the endocrine system, the gastrointestinal tract, the renal system, the hepatic system, the metabolic system, the respiratory system, the central nervous system, may be a cancer or other malignancy and/or may be caused by or associated with a pathogen.

It will be appreciated that these general embodiments defined according to broad categories of diseases, disorders and conditions are not mutually exclusive. In this regard any particular disease, disorder or condition may be categorized according to more than one of the above general embodiments. A non-limiting example is type I diabetes which is an autoimmune disease and a disease of the endocrine system.

In one embodiment of the fifth, sixth or seventh aspect of the present invention, the disease, disorder or condition is responsive to NLRP3 inhibition. As used herein, the term "NLRP3 inhibition" refers to the complete or partial reduction in the level of activity of NLRP3 and includes, for example, the inhibition of active NLRP3 and/or the inhibition of activation of NLPR3.

There is evidence for a role of NLRP3-induced IL-1 and IL-18 in the inflammatory responses occurring in connection with, or as a result of, a multitude of different disorders (Menu et al., Clinical and Experimental Immunology, 166: 1-15, 2011; Strowig et al., Nature, 481:278-286, 2012).

NLRP3 has been implicated in a number of autoinflammatory diseases, including Familial Mediterranean fever (FMF), TNF receptor associated periodic syndrome (TRAPS), hyperimmunoglobulinemia D and periodic fever syndrome (HIDS), pyogenic arthritis, pyoderma gangrenosum and acne (PAPA), Sweet's syndrome, chronic nonbacterial osteomyelitis (CNO), and acne vulgaris (Cook et al., Eur. J. Immunol., 40: 595-653, 2010). In particular, NLRP3 mutations have been found to be responsible for a set of rare autoinflammatory diseases known as CAPS (Ozaki et al., J. Inflammation Research, 8:15-27, 2015; Schroder et al., Cell, 140: 821-832, 2010; and Menu et al., Clinical and Experimental Immunology, 166: 1-15, 2011). CAPS are heritable diseases characterized by recurrent fever and inflammation and are comprised of three autoinflammatory disorders that form a clinical continuum. These diseases, in order of increasing severity, are familial cold autoinflammatory syndrome (FCAS), Muckle-Wells syndrome (MWS), and chronic infantile cutaneous neurological articular syndrome (CINCA; also called neonatal-onset multisystem inflammatory disease, NOMID), and all have been shown to result from gain-of-function mutations in the NLRP3 gene, which leads to increased secretion of IL-1β.

A number of autoimmune diseases have been shown to involve NLRP3 including, in particular, multiple sclerosis, type-1 diabetes (TID), psoriasis, rheumatoid arthritis (RA), Behcet's disease, Schnitzler syndrome, and macrophage activation syndrome (Masters Clin. Immunol. 2013; Braddock et al., Nat. Rev. Drug Disc., 3: 1-10, 2004; and Inoue et al., Immunology, 139, 11-18). NLRP3 has also been shown to play a role in a number of lung diseases including chronic obstructive pulmonary disorder (COPD), asthma, asbestosis, and silicosis (De Nardo et al., Am. J. Pathol., 184: 42-54, 2014). NLRP3 has also been suggested have a role in a number of diseases of the central nervous system, including Parkinson's disease (PD), Alzheimer's disease (AD), dementia, Huntington's disease, cerebral malaria, and brain injury from pneumococcal meningitis (Walsh et al., Nature Reviews, 15: 84-97, 2014). NRLP3 activity has also been shown to be involved in various metabolic diseases including type 2 diabetes (T2D), atherosclerosis, obesity, gout, pseudo-gout, and metabolic syndrome (Wen et al., Nature Immunology, 13: 352-357, 2012; Duewell et al., Nature, 464: 1357-1361, 2010; Strowig et al., Nature, 481: 278-286, 2012). Other diseases in which NLRP3 has been shown to be involved include ocular diseases such as age-related macular degeneration (Doyle et al., Nature Medicine, 18: 791-798, 2012), liver diseases including non-alcoholic steatohepatitis (NASH) (Henao-Meija et al., Nature, 482: 179-185, 2012), inflammatory reactions in the skin including contact hypersensitivity and UVB irradiation (Schroder et al., Science, 327: 296-300, 2010), inflammatory reactions in the joints (Braddock et al., Nat. Rev. Drug Disc., 3: 1-10, 2004), stroke (Walsh et al., Nature Reviews, 15: 84-97, 2014), and inflammatory bowel diseases including ulcerative colitis and Crohn's disease (Braddock et al., Nat. Rev. Drug Disc., 3: 1-10, 2004).

NLRP3 has also been implicated in the pathogenesis of many cancers (Menu et al., Clinical and Experimental Immunology 166: 1-15, 2011; and Masters Clin. Immunol. 2013), and has been shown to be required for the efficient control of viral, bacterial, fungal, and helminth pathogen infections (Strowig et al., Nature, 481:278-286, 2012).

Accordingly, examples of diseases, disorders or conditions which may be responsive to NLRP3 inhibition and which may be treated or prevented in accordance with the fifth, sixth or seventh aspect of the present invention include:
(i) inflammation, including inflammation occurring as a result of an inflammatory disorder, e.g. an autoinflammatory disease, inflammation occurring as a symptom of a non-inflammatory disorder, inflammation occurring as a result of infection, or inflammation secondary to trauma, injury or autoimmunity;
(ii) auto-immune diseases such as acute disseminated encephalitis, Addison's disease, ankylosing spondylitis, antiphospholipid antibody syndrome (APS), anti-synthetase syndrome, aplastic anemia, autoimmune adrenalitis, autoimmune hepatitis, autoimmune oophoritis, autoimmune polyglandular failure, autoimmune thyroiditis, Coeliac disease, Crohn's disease, type 1 diabetes (T1D), Goodpasture's syndrome, Graves' disease, Guillain-Barré syndrome (GBS), Hashimoto's disease, idiopathic thrombocytopenic purpura, Kawasaki's disease, lupus erythematosus including systemic lupus erythematosus (SLE), multiple sclerosis (MS), myasthenia gravis, opsoclonus myoclonus syndrome (OMS), optic neuritis, Ord's thyroiditis, pemphigus, pernicious anaemia, polyarthritis, primary biliary cirrhosis, rheumatoid arthritis (RA), psoriatic arthritis, juvenile idiopathic arthritis, Reiter's syndrome, Sjögren's syndrome, a systemic connective tissue disorder, Takayasu's arteritis, temporal arteritis, warm autoimmune hemolytic anemia, Wegener's granulomatosis, alopecia universalis, Behçet's disease, Chagas' disease, dysautonomia, endometriosis, hidradenitis suppurativa (HS), interstitial cystitis, neuromyotonia, psoriasis, sarcoidosis, scleroderma, ulcerative colitis, Schnitzler syndrome, macrophage activation syndrome, Blau syndrome, vitiligo or vulvodynia;
(iii) cancer including lung cancer metastasis, pancreatic cancers, gastric cancers, myelodisplastic syndrome, and leukemia;
(iv) infections including viral infections (e.g. from influenza virus, cytomegalovirus, Epstein Barr Virus, human immunodeficiency virus (HIV), alphavirus such as Chikungunya and Ross River virus, flaviviruses such as Dengue virus and Zika virus, or papillomavirus), bacterial infections (e.g. from *Staphylococcus aureus, Helicobacter pylori, Bacillus anthracis, Bordatella pertussis, Burkholderia pseudomallei, Corynebacterium diptheriae, Clostridium tetani, Clostridium botulinum, Streptococcus pneumoniae, Streptococcus pyogenes, Listeria monocytogenes, Hemophilus influenzae, Pasteurella multicida, Shigella dysenteriae, Mycobacterium tuberculosis, Mycobacterium leprae, Mycoplasma pneumoniae, Mycoplasma hominis, Neisseria meningitidis, Neisseria gonorrhoeae, Rickettsia rickettsii, Legionella pneumophila, Klebsiella pneumoniae, Pseudomonas aeruginosa, Propionibacterium acnes, Treponema pallidum, Chlamydia trachomatis, Vibrio cholerae, Salmonella typhimurium, Salmonella typhi, Borrelia burgdorferi* or *Yersinia pestis*), fungal infections (e.g. from *Candida* or *Aspergillus* species), protozoan infections (e.g. from *Plasmodium, Babesia, Giardia, Entamoeba, Leishmania* or Trypanosomes), helminth infections (e.g. from *schistosoma*, roundworms, tapeworms or flukes) and prion infections;
(v) central nervous system diseases such as Parkinson's disease, Alzheimer's disease, dementia, motor neuron disease, Huntington's disease, cerebral malaria, and brain injury from pneumococcal meningitis;
(vi) metabolic diseases such as type 2 diabetes (T2D), atherosclerosis, obesity, gout, and pseudo-gout;
(vii) cardiovascular diseases such as hypertension, ischaemia, reperfusion injury, stroke including ischemic stroke, myocardial infarction including recurrent myocardial infarction, congestive heart failure, embolism, abdominal aortic aneurism, and pericarditis including Dressler's syndrome;
(viii) respiratory diseases including chronic obstructive pulmonary disorder (COPD), asthma such as allergic asthma and steroid-resistant asthma, asbestosis, silicosis, nanoparticle induced inflammation, cystic fibrosis and idiopathic pulmonary fibrosis;
(ix) liver diseases including non-alcoholic steatohepatitis (NASH) and alcoholic liver disease;
(x) renal diseases including chronic kidney disease, oxalate nephropathy, nephrocalcinosis, glomerulonephritis, and diabetic nephropathy;
(xi) ocular diseases including those of the ocular epithelium, age-related macular degeneration (AMD), uveitis, corneal infection, and dry eye;
(xii) skin diseases including dermatitis such as contact dermatitis, contact hypersensitivity, sunburn, skin lesions, hidradenitis suppurativa (HS), and other cyst-causing skin diseases;

(xiii) psychological disorders such as depression and psychological stress;
(xiv) graft versus host disease; and
(xv) any disease where an individual has been determined to carry a germline or somatic non-silent mutation in NLRP3.

Examples of inflammation that may be treated or prevented in accordance with the fifth, sixth or seventh aspect of the present invention include inflammatory responses occurring in connection with, or as a result of:
(i) a skin condition such as contact hypersensitivity, sunburn, psoriasis, atopical dermatitis, contact dermatitis, allergic contact dermatitis, seborrhoetic dermatitis, lichen planus, scleroderma, pemphigus, epidermolysis bullosa, urticaria, erythemas, or alopecia;
(ii) a joint condition such as osteoarthritis, systemic juvenile idiopathic arthritis, adult-onset Still's disease, relapsing polychondritis, rheumatoid arthritis, osteoarthritis, juvenile chronic arthritis, gout, or a seronegative spondyloarthropathy (e.g. ankylosing spondylitis, psoriatic arthritis or Reiter's disease);
(iii) a muscular condition such as polymyositis or myasthenia gravis;
(iv) a gastrointestinal tract condition such as inflammatory bowel disease (including Crohn's disease and ulcerative colitis), gastric ulcer, coeliac disease, proctitis, pancreatitis, eosinopilic gastro-enteritis, mastocytosis, antiphospholipid syndrome, or a food-related allergy which may have effects remote from the gut (e.g., migraine, rhinitis or eczema);
(v) a respiratory system condition such as chronic obstructive pulmonary disease (COPD), asthma (including bronchial, allergic, intrinsic, extrinsic or dust asthma, and particularly chronic or inveterate asthma, such as late asthma and airways hyper-responsiveness), bronchitis, rhinitis (including acute rhinitis, allergic rhinitis, atrophic rhinitis, chronic rhinitis, rhinitis caseosa, hypertrophic rhinitis, rhinitis pumlenta, rhinitis sicca, rhinitis medicamentosa, membranous rhinitis, seasonal rhinitis e.g. hay fever, and vasomotor rhinitis), sinusitis, idiopathic pulmonary fibrosis (IPF), sarcoidosis, farmer's lung, silicosis, asbestosis, adult respiratory distress syndrome, hypersensitivity pneumonitis, or idiopathic interstitial pneumonia;
(vi) a vascular condition such as atherosclerosis, Behcet's disease, vasculitides, or wegener's granulomatosis;
(vii) an autoimmune condition such as systemic lupus erythematosus, Sjogren's syndrome, systemic sclerosis, Hashimoto's thyroiditis, type I diabetes, idiopathic thrombocytopenia purpura, or Graves disease;
(viii) an ocular condition such as uveitis, allergic conjunctivitis, or vernal conjunctivitis;
(ix) a nervous condition such as multiple sclerosis or encephalomyelitis;
(x) an infection or infection-related condition, such as Acquired Immunodeficiency Syndrome (AIDS), acute or chronic bacterial infection, acute or chronic parasitic infection, acute or chronic viral infection, acute or chronic fungal infection, meningitis, hepatitis (A, B or C, or other viral hepatitis), peritonitis, pneumonia, epiglottitis, malaria, dengue hemorrhagic fever, leishmaniasis, streptococcal myositis, *Mycobacterium tuberculosis*, *Mycobacterium avium intracellulare*, *Pneumocystis carinii* pneumonia, orchitis/epidydimitis, *legionella*, Lyme disease, influenza A, epstein-barr virus, viral encephalitis/aseptic meningitis, or pelvic inflammatory disease;
(xi) a renal condition such as mesangial proliferative glomerulonephritis, nephrotic syndrome, nephritis, glomerular nephritis, acute renal failure, uremia, or nephritic syndrome;
(xii) a lymphatic condition such as Castleman's disease;
(xiii) a condition of, or involving, the immune system, such as hyper IgE syndrome, lepromatous leprosy, familial hemophagocytic lymphohistiocytosis, or graft versus host disease;
(xiv) a hepatic condition such as chronic active hepatitis, non-alcoholic steatohepatitis (NASH), alcohol-induced hepatitis, or primary biliary cirrhosis;
(xv) a cancer, including those cancers listed below;
(xvi) a burn, wound, trauma, haemorrhage or stroke;
(xvii) radiation exposure; and/or
(xviii) obesity.

In one embodiment of the fifth, sixth or seventh aspect of the present invention, the disease, disorder or condition is selected from:
(i) an autoinflammatory disease such as cryopyrin-associated periodic syndromes (CAPS), Muckle-Wells syndrome (MWS), familial cold autoinflammatory syndrome (FCAS), familial Mediterranean fever (FMF), Neonatal onset multisystem inflammatory disease (NOMID), Tumour Necrosis Factor (TNF) Receptor-Associated Periodic Syndrome (TRAPS), hyperimmunoglobulinemia D and periodic fever syndrome (HIDS), deficiency of interleukin 1 receptor antagonist (DIRA), Majeed syndrome, pyogenic arthritis, pyoderma gangrenosum and acne syndrome (PAPA), adult-onset Still's disease (AOSD), haploinsufficiency of A20 (HA20), pediatric granulomatous arthritis (PGA), PLCG2-associated antibody deficiency and immune dysregulation (PLAID), PLCG2-associated autoinflammatory, antibody deficiency and immune dysregulation (APLAID), or sideroblastic anaemia with B-cell immunodeficiency, periodic fevers and developmental delay (SIFD);
(ii) non-alcoholic steatohepatitis (NASH); or
(iii) cancer such as lung cancer, pancreatic cancer, gastric cancer, myelodisplastic syndrome, leukaemia including acute lymphocytic leukaemia (ALL) and acute myeloid leukaemia (AML), adrenal cancer, anal cancer, basal and squamous cell skin cancer, bile duct cancer, bladder cancer, bone cancer, brain and spinal cord tumours, breast cancer, Castleman disease, cervical cancer, chronic lymphocytic leukaemia (CLL), chronic myeloid leukaemia (CML), chronic myelomonocytic leukaemia (CMML), colorectal cancer, endometrial cancer, oesophagus cancer, Ewing family of tumours, eye cancer, gallbladder cancer, gastrointestinal carcinoid tumours, gastrointestinal stromal tumour (GIST), gestational trophoblastic disease, Hodgkin lymphoma, Kaposi sarcoma, kidney cancer, laryngeal and hypopharyngeal cancer, liver cancer, lung carcinoid tumour, lymphoma, malignant mesothelioma, melanoma skin cancer, Merkel cell skin cancer, multiple myeloma, nasal cavity and paranasal sinuses cancer, nasopharyngeal cancer, neuroblastoma, non-Hodgkin lymphoma, non-small cell lung cancer, oral cavity and oropharyngeal cancer, osteosarcoma, ovarian cancer, penile cancer, pituitary tumours, prostate cancer, retinoblastoma, rhabdomyosarcoma, salivary gland cancer, skin cancer, small cell lung cancer, small intestine cancer, soft tissue sarcoma, stomach cancer, testicular cancer, thymus cancer, thyroid cancer, uterine sarcoma, vaginal cancer, vulvar cancer, Waldenstrom macroglobulinemia, or Wilms tumour.

In another embodiment of the fifth, sixth or seventh aspect of the present invention, the disease, disorder or condition is responsive to the stimulation of insulin secretion. Examples of diseases, disorders or conditions which may be responsive to the stimulation of insulin secretion and which may be treated or prevented in accordance with the fifth, sixth or seventh aspect of the present invention include all forms of diabetes and prediabetes, in particular type 1 diabetes (TID) (especially type 1 diabetes (TID) in which insulin secretion is detectable), type 2 diabetes (T2D), prediabetes, and gestational diabetes.

In a further embodiment of the fifth, sixth or seventh aspect of the present invention, the disease, disorder or condition is responsive to both NLRP3 inhibition and the stimulation of insulin secretion. Such diseases, disorders or conditions include in particular disorders of the liver and/or pancreas which may have an inflammatory component. In such cases, it is useful to treat patients with a first drug that acts as anti-inflammatory, for example to inhibit pyroptosis and to prevent or reverse fibrosis, and a second drug that can modulate metabolism, for example to regulate glucose levels and/or to prevent or reverse steatosis.

For instance, as the hepatic manifestation of metabolic syndrome, non-alcoholic fatty liver disease (NAFLD) is the leading cause of chronic liver disease in the Western world, and is frequently observed in combination with T2D. NAFLD is characterised by the build-up of excess fat in the liver of people who do not abuse alcohol and is associated with a broad spectrum of hepatic pathology. The first stage of NAFLD comprises steatosis, and twenty percent of NAFLD cases progress to non-alcoholic steatohepatitis (NASH) which is characterised by a combination of steatosis and inflammation, and can lead to liver fibrosis (as a result of persistent high levels of inflammation), cirrhosis, hepatocellular carcinoma, and increased mortality. There is evidence for a role of the NLRP3 inflammasome in the progression from NAFLD to NASH and NASH-associated inflammation (Henao-Meija et al., Nature, 482: 179-185, 2012), and in particular, in the inflammation that is the cause of liver fibrosis. NAFLD and NASH thus have both an NLRP3-dependent inflammatory component, and a metabolic component that drives steatosis (which in turn may be a further driver of inflammation and in this context hepatitis).

The compounds, salts, solvates, prodrugs and pharmaceutical compositions of the present invention are particularly advantageous since they have the potential to both target NLRP3-dependent inflammation and modulate metabolism via the stimulation of insulin secretion. Both the NLRP3-dependent inflammatory component and the metabolic component of disorders such as NASH may therefore be targeted by a single active pharmaceutical ingredient.

Particular examples of diseases, disorders or conditions which may be responsive to both NLRP3 inhibition and the stimulation of insulin secretion and which may be treated or prevented in accordance with the fifth, sixth or seventh aspect of the present invention include conditions associated with insulin resistance such as type 2 diabetes (T2D); non-alcoholic fatty liver disease (NAFLD), and non-alcoholic steatohepatitis (NASH); alcoholic fatty liver disease (AFLD), and alcoholic steatohepatitis (ASH); disorders involving reduced insulin production and/or secretion including disorders of the pancreas such as pancreatic cancer and chronic and acute pancreatitis; and hyperglucagonemia.

In yet another embodiment of the fifth, sixth or seventh aspect of the present invention, the treatment or prevention includes the treatment or prevention of two or more comorbid diseases, disorders or conditions. Typically, the first disease, disorder or condition is responsive to the stimulation of insulin secretion and the second disease, disorder or condition is responsive to NLRP3 inhibition. For example, the fifth, sixth or seventh aspect of the present invention may relate to the treatment or prevention of a first disease, disorder or condition selected from diabetes or prediabetes, and a second disease, disorder or condition selected from:

(i) inflammation;
(ii) a cardiovascular disease;
(iii) a central nervous system disease;
(iv) a renal disease;
(v) an ocular disease;
(vi) a skin disease;
(vii) a liver disease;
(viii) a lung disease;
(ix) a cancer; or
(x) a metabolic disease that is not responsive to the stimulation of insulin secretion.

An eighth aspect of the invention provides a method of inhibiting NLRP3 and/or stimulating insulin secretion, the method comprising the use of a compound of the first or second aspect, or a pharmaceutically acceptable salt, solvate or prodrug of the third aspect, or a pharmaceutical composition of the fourth aspect, to inhibit NLRP3 and/or stimulate insulin secretion. Typically, the method is a method of inhibiting NLRP3 and stimulating insulin secretion.

In one embodiment of the eighth aspect of the present invention, the method is performed ex vivo or in vitro, for example in order to analyse the effect on cells of NLRP3 inhibition and/or the stimulation of insulin secretion.

In another embodiment of the eighth aspect of the present invention, the method is performed in vivo. For example, the method may comprise the step of administering an effective amount of a compound of the first or second aspect, or a pharmaceutically acceptable salt, solvate or prodrug of the third aspect, or a pharmaceutical composition of the fourth aspect, to thereby inhibit NLRP3 and/or stimulate insulin secretion. Typically the administration is to a subject in need thereof.

Alternately, the method of the eighth aspect of the invention may be a method of inhibiting NLRP3 and/or stimulating insulin secretion in a non-human animal subject, the method comprising the steps of administering the compound, salt, solvate, prodrug or pharmaceutical composition to the non-human animal subject and optionally subsequently mutilating or sacrificing the non-human animal subject. Typically such a method further comprises the step of analysing one or more tissue or fluid samples from the optionally mutilated or sacrificed non-human animal subject.

A ninth aspect of the invention provides for a compound of the first aspect or second aspect, or a pharmaceutically acceptable salt, solvate or prodrug of the third aspect, or a pharmaceutical composition of the fourth aspect, for use in the inhibition of NLRP3 and/or for use in the stimulation of insulin secretion. Typically, the compound, salt, solvate, prodrug or pharmaceutical composition is for use in the inhibition of NLRP3 and the stimulation of insulin secretion. Typically the use comprises the administration of the compound, salt, solvate, prodrug or pharmaceutical composition to a subject.

A tenth aspect of the invention provides for the use of a compound of the first or second aspect, or a pharmaceutically effective salt, solvate or prodrug of the third aspect, in the manufacture of a medicament for the inhibition of NLRP3 and/or the stimulation of insulin secretion. Typically, the medicament is for the inhibition of NLRP3 and the stimulation of insulin secretion. Typically the inhibition and/or stimulation comprises the administration of the compound, salt, solvate, prodrug or pharmaceutical composition to a subject.

Unless stated otherwise, in any of the fifth to tenth aspects of the invention, the subject may be any human or other animal. Typically, the subject is a mammal, more typically a human or a domesticated mammal such as a cow, pig, lamb, goat, horse, cat, dog, etc. Most typically, the subject is a human.

Any of the medicaments employed in the present invention can be administered by oral, parental (including intravenous, subcutaneous, intramuscular, intradermal, intratracheal, intraperitoneal, intraarticular, intracranial and epidural), airway (aerosol), rectal, vaginal or topical (including transdermal, buccal, mucosal and sublingual) administration.

Typically, the mode of administration selected is that most appropriate to the disorder or disease to be treated or prevented.

For oral administration, the compounds, salts, solvates or prodrugs of the present invention will generally be provided in the form of tablets, capsules, hard or soft gelatine capsules, caplets, troches or lozenges, as a powder or granules, or as an aqueous solution, suspension or dispersion.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose. Corn starch and alginic acid are suitable disintegrating agents. Binding agents may include starch and gelatine. The lubricating agent, if present, may be magnesium stearate, stearic acid or talc. If desired, the tablets may be coated with a material, such as glyceryl monostearate or glyceryl distearate, to delay absorption in the gastrointestinal tract. Tablets may also be effervescent and/or dissolving tablets.

Capsules for oral use include hard gelatine capsules in which the active ingredient is mixed with a solid diluent, and soft gelatine capsules wherein the active ingredient is mixed with water or an oil such as peanut oil, liquid paraffin or olive oil.

Powders or granules for oral use may be provided in sachets or tubs. Aqueous solutions, suspensions or dispersions may be prepared by the addition of water to powders, granules or tablets.

Any form suitable for oral administration may optionally include sweetening agents such as sugar, flavouring agents, colouring agents and/or preservatives.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For parenteral use, the compounds, salts, solvates or prodrugs of the present invention will generally be provided in a sterile aqueous solution or suspension, buffered to an appropriate pH and isotonicity. Suitable aqueous vehicles include Ringer's solution and isotonic sodium chloride or glucose. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate. The compounds of the invention may also be presented as liposome formulations.

For transdermal and other topical administration, the compounds, salts, solvates or prodrugs of the invention will generally be provided in the form of ointments, cataplasms (poultices), pastes, powders, dressings, creams, plasters or patches.

Suitable suspensions and solutions can be used in inhalers for airway (aerosol) administration.

The dose of the compounds, salts, solvates or prodrugs of the present invention will, of course, vary with the disorder or disease to be treated or prevented. In general, a suitable dose will be in the range of 0.01 to 500 mg per kilogram body weight of the recipient per day. The desired dose may be presented at an appropriate interval such as once every other day, once a day, twice a day, three times a day or four times a day. The desired dose may be administered in unit dosage form, for example, containing 1 mg to 50 g of active ingredient per unit dosage form.

For the avoidance of doubt, insofar as is practicable any embodiment of a given aspect of the present invention may occur in combination with any other embodiment of the same aspect of the present invention. In addition, insofar as is practicable it is to be understood that any preferred, typical or optional embodiment of any aspect of the present invention should also be considered as a preferred, typical or optional embodiment of any other aspect of the present invention.

FIGURES

FIG. 1 shows the insulin-secretory activity of compounds of the invention and other comparative compounds.

EXAMPLES—COMPOUND SYNTHESIS

All solvents, reagents and compounds were purchased and used without further purification unless stated otherwise.

For Intermediates I-3 to I-17 and Examples 1-22:

$^1$H NMR and $^{13}$C NMR spectra were recorded using a BrukerAvance 600 MHz spectrometer (operating at 600 MHz for $^1$H NMR and 151 MHz for $^{13}$C NMR) $^{13}$C and $^1$H chemical shifts (δ), reported in ppm, were internally referenced to tetramethylsilane (TMS). LC-MS analysis was performed using a 0.05% (v/v) formic acid$_{(aq)}$/0.05% formic acid in $CH_3CN$ solvent system on a Shimadzu Prominence instrument equipped with an Agilent Eclipse XDB-Phenyl column (3.5×100 mm, 3 μm) maintained at 40° C., SPD-M20A diode array UV-Vis detector, ELSD-LT II evaporative light scattering detector (ELSD) and LC-MS-2020 mass spectrometer. High resolution mass spectrometry (HRMS) was performed on a Bruker MicroTOF mass spectrometer with electrospray ionisation (ESI). Medium pressure liquid chromatography (MPLC) purification was conducted on a Grace Reveleris® X1 using two serial 12 g Grace C18 columns with a 10 mM $NH_4HCO_{3(aq)}$/$CH_3CN$ solvent system flowing at 30 mL/min. HPLC purification was performed on a Gilson PLC 2020 instrument using an Agilent Eclipse XDB-Phenyl column (21.2 mm×100 mm, 5 μm) with 10 mM $NH_4HCO_{3(aq)}/CH_3CN$ solvent system flowing at 20 mL/min.

For Intermediate I-23 and Examples 23-31:

Analytical methods: NMR spectra were run on Bruker 400 MHz spectrometers using ICON-NMR, under TopSpin program control. Spectra were measured at 298 K, unless indicated otherwise, and were referenced relative to the solvent resonance.

LC-MS Methods: Using SHIMADZU LCMS-2020, Agilent 1200 LC/G1956A MSD and Agilent 1200\G6110A, Agilent 1200 LC & Agilent 6110 MSD.

Purification Method: Automated reversed phase column chromatography was carried out using a Gilson 281 system driven by Gilson 322 pump, Gilson 156 UV/Vis detection unit and Gilson GX-281 fraction collector. The Phenomenex Gemini column (150 mm×25 mm×10 um) was conditioned prior to use with $CH_3CN$ (2 min) then brought to 5% water (0.05% ammonia hydroxide vol/vol) in 0.3 min and kept 2 min at 5% water (0.05% ammonia hydroxide v/v). Flow rate=25 mL/min. Separation runs:

| Time (min) | A: water (0.05% ammonia hydroxide V/V %) | B: $CH_3CN$ (%) |
| --- | --- | --- |
| 0 | 95 | 5 |
| 12 | 65 | 35 |
| 12.2 | 0 | 100 |
| 14.2 | 0 | 100 |
| 14.5 | 95 | 5 |

Detection wavelengths=220 and 254 nm. Before each new run the cartridge was cleaned using the conditioning method.

General Synthetic Methods

GENERAL METHOD A

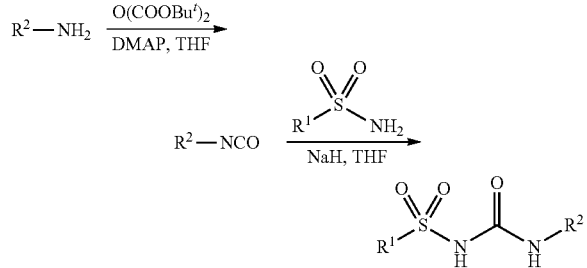

An isocyanate was prepared in situ from the corresponding amine by dissolving di-tert-butyl dicarbonate (1.1 eq.) in tetrahydrofuran (THF) (3 mL/mmol amine), treating with N,N-dimethylpyridin-4-amine (DMAP) (1.1 eq.) and stirring for 5 min at room temperature before adding the amine (1 eq.) and stirring for a further 20 min. Meanwhile a sulfonamide sodium salt was prepared in situ by dissolving the a sulfonamide (1 eq.) in THF (3 mL/mmol), treating with NaH (1.0 eq., 60% oil dispersion) and stirring under reduced pressure until effervescence ceased (ca. 5-10 min). The sulfonamide salt and isocyanate solutions were combined and stirred at room temperature for 15 h under $N_2$ atmosphere, monitored by LC-MS. Reaction mixtures were concentrated in vacuo, dissolved in the minimum volume 1:1 $CH_3CN$/dimethylformamide (DMF) and purified via reverse phase MPLC. Typically a four minute aqueous wash was followed by a 15 min 10 mM $NH_4HCO_{3(aq)}/CH_3CN$ gradient.

GENERAL METHOD A1:

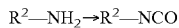

To a solution of $R^2$ amine intermediate (1 eq.) with or without a base such as triethylamine (1.2 eq.), in an anhydrous aprotic solvent such as tetrahydrofuran or dichloromethane, was added triphosgene (0.4 to 1.1 eq.). The reaction was stirred at ambient temperature or, where necessary, heated at reflux until completion, typically from 2 to 18 h.

GENERAL METHOD A2:

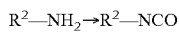

To di-t-butyldicarbonate (1.2-1.4 eq.) in anhydrous acetonitrile or THF was added DMAP (15-100 mol %), after 5 minutes, a solution of $R^2$ amine intermediate (1.0 eq.) in acetonitrile was added. The reaction mixture was stirred for 30-60 min at room temperature.

GENERAL METHOD $B_1$

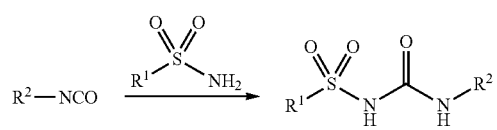

To $R^1$ sulfonamide intermediate (1 eq) in anhydrous THF (5 mL/mmol) was added NaH (1 eq) at 0° C. and stirred for 30 min to 2 h, or until completion, at ambient temperature under nitrogen atmosphere. Again cooled to 0° C., $R^2$ isocyanate (1.0 eq) in THF was added and stirred at ambient temperature until completion, typically 2 to 16 h.

GENERAL METHOD $B_2$

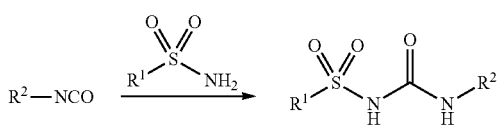

To crude $R^2$ isocyanate (1.0 eq) in anhydrous THF or DCM (5-11 mL/mmol) was added $R^1$ sulfonamide (1.0 eq) followed by base such as triethylamine, DIPEA, or DBU (1-2 eq) and the reaction mixture stirred at ambient temperature overnight.

GENERAL METHOD $B_3$

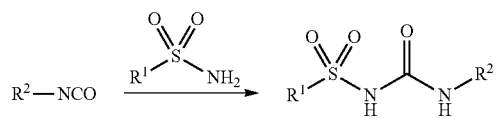

$R^1$ sulfonamide (1.0 eq) was dissolved in anhydrous THF under a nitrogen atmosphere. Solid sodium methoxide (1.0 eq) was added in one portion. This mixture was stirred at ambient temperature for 3 h. A solution of the $R^2$ isocyanate (1.17 eq) in THF was added drop wise. The reaction mixture was stirred at room temperature overnight.

GENERAL METHOD C

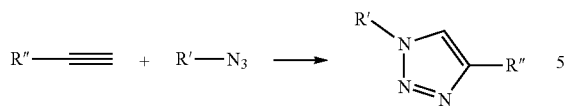

Alkyne (1 eq) and azide (1.2 eq), 5 mol % CuSO₄, 10 mol % NaAsc solution in DMSO (500 μL) were stirred at room temperature until completion, typically 12 h.

GENERAL METHOD D₁: Precursor sulphonamides wherein R¹ is a substituted pyrazole moiety may be prepared according to the following synthetic scheme

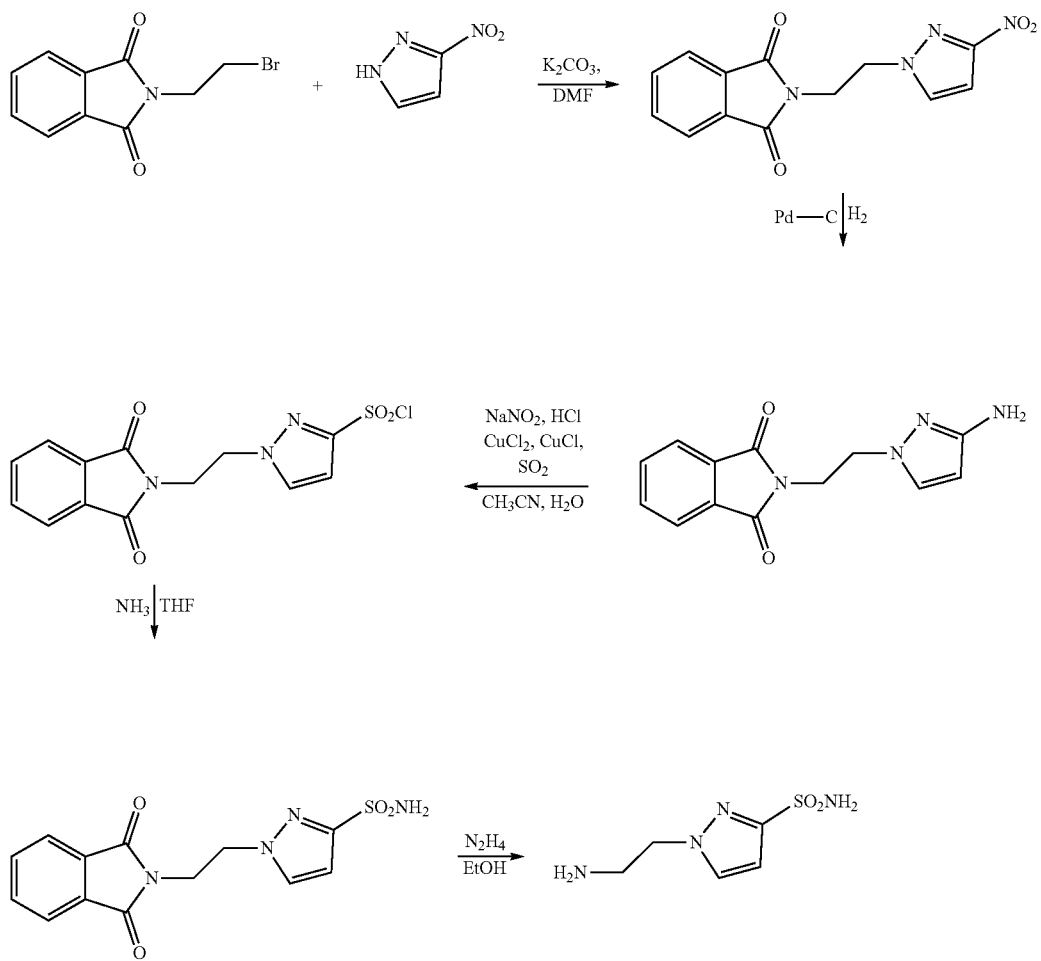

GENERAL METHOD D₂
Compounds of Formula I wherein R¹ is a pyrazole moiety and X comprises an amide moiety may be prepared according to the following synthetic scheme

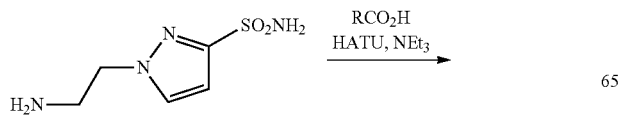

87
-continued

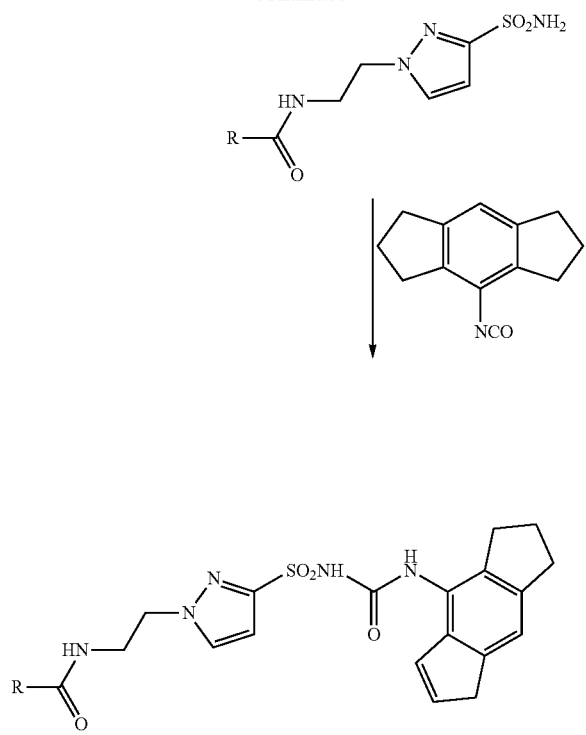

GENERAL METHOD D3:
Compounds of Formula I wherein R¹ is a pyrazole moiety and X comprises a urea moiety may be prepared according to the following synthetic scheme

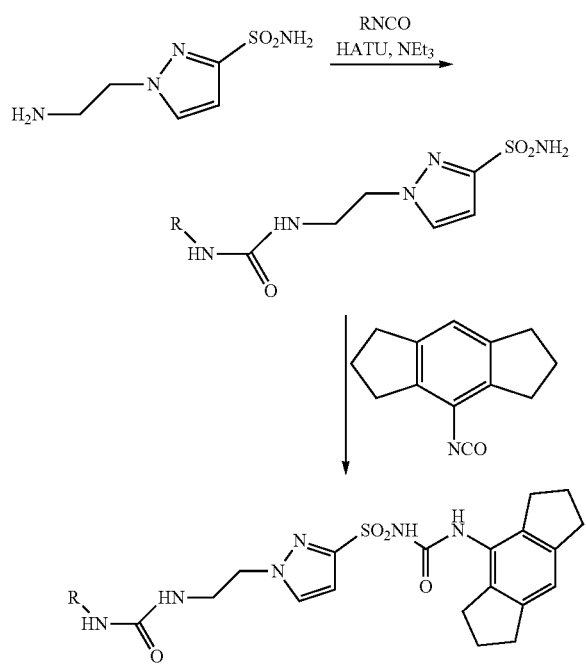

Other compounds of Formula I wherein R¹ is a pyrazole moiety having a different regiochemistry may be prepared by methods analogous to general methods D1-D3.

88
Intermediate Synthesis

Intermediate I-3: 5-Methyl-N-(4-sulfamoylphenethyl)pyrazine-2-carboxamide

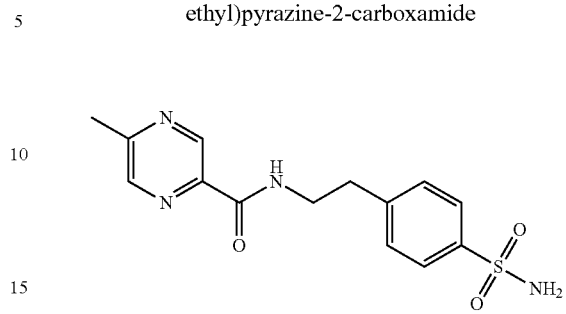

N-(4-(N-(Cyclohexylcarbamoyl)sulfamoyl)phenethyl)-5-methylpyrazine-2-carboxamide (250 mg, 0.56 mmol) dissolved in pyridine (8 mL) was treated with phthalic anhydride (83 mg, 0.56 mmol) and DMAP (10 mg, 0.082 mmol), then heated at reflux for 5 h under $N_2$ atmosphere. The reaction mixture was purified by MPLC affording the titled compound as an amorphous white solid (113 mg, 63%): $^1$H NMR (600 MHz, DMSO-$d_6$) δ 9.03 (d, J=1.4 Hz, 1H), 8.96 (t, J=6.0 Hz, 1H), 8.61 (m, 1H), 7.73 (d, J=8.4 Hz, 2H, 7.42 (d, J=8.4 Hz, 2H), 7.30 (s, 2H), 3.57 (dt, J=7.3, 6.0 Hz, 2H, 2.95 (t, J=7.3 Hz, 2H), 2.58 (s, 3H); $^{13}$C NMR (151 MHz, DMSO-$d_6$) δ 162.8, 156.7, 143.4 (C-1), 142.7 (C-11), 142.3 (C-14), 141.9 (C-12), 141.9 (C-6), 129.0 (C-4, 5), 125.6, 39.8, 34.6, 21.2; HRMS (ESI-TOF) m/z calcd for $C_{14}H_{17}N_4O_3S$ [M+H]$^+$ 321.1016, found 321.1029; LC-MS m/z 321.0 [M+H]$^+$, purity>95% (ELSD).

Intermediate I-4: 5-Methyl-N-(4-sulfamoylphenethyl)isoxazole-3-carboxamide

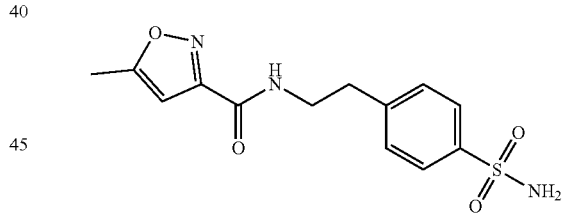

5-Methylisoxazole-3-carboxylic acid (150 mg, 1.18 mmol) dissolved in toluene (2 mL) was treated with DMF (1 drop) and thionyl chloride (1.42 mmol, 103 μL) then heated to reflux for 5 h. The solvent was removed in vacuo to afford crude 5-methylisoxazole-3-carbonyl chloride (155 mg, 1.06 mmol) as a brown oil. The crude acid chloride without purification was dissolved in THF (4 mL), treated with Et$_3$N (155 μL, 1.06 mmol) and stirred for 5 min, before adding 4-(2-aminoethyl)benzenesulfonamide (220 mg, 1.10 mmol) and stirring at room temperature for 15 h under $N_2$ atmosphere. The reaction mixture was concentrated in vacuo and purified by MPLC, affording the titled compound as an amorphous white solid (205 mg, 62%): $^1$H NMR (600 MHz, DMSO-$d_6$) δ 8.79 (t, J=5.8 Hz, 1H), 7.74 (d, J=8.3 Hz, 2H), 7.41 (d, J=8.3 Hz, 2H), 7.30 (s, 2H), 6.50 (q, J=0.8 Hz, 1H), 3.49 (m, 2H), 2.91 (t, J=7.2 Hz, 2H), 2.45 (d, J=0.8 Hz, 3H); $^{13}$C NMR (151 MHz, DMSO-$d_6$) δ 171.0, 158.8, 158.5, 143.3, 142.0, 129.0, 125.6, 101.1, 39.8, 34.3, 11.7; HRMS

Intermediate I-5: 4-(2-(7-Methoxy-4,4-dimethyl-1,3-dioxo-3,4-dihydroisoquinolin-2(1H)-yl)ethyl)benzenesulfonamide

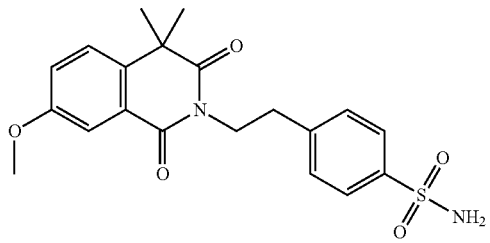 [SMILES: COc1ccc2c(c1)C(=O)N(CCc1ccc(S(N)(=O)=O)cc1)C(=O)C2(C)C]

N-(Cyclohexylcarbamoyl)-4-(2-(7-methoxy-4,4-dimethyl-1,3-dioxo-3,4-dihydroisoquinolin-2(1H)-yl)ethyl)benzenesulfonamide (504 mg, 0.96 mmol) dissolved in pyridine (8 mL) was treated with phthalic anhydride (143 mg, 0.97 mmol) and DMAP (11.8 mg, 0.097 mmol), then heated at reflux for 5 h under $N_2$ atmosphere. The reaction mixture was purified by MPLC, affording the titled compound as an amorphous white solid (291 mg, 77%): $^1$H NMR (600 MHz, DMSO-$d_6$) δ 7.72 (d, J=8.5 Hz, 2H), 7.61 (d, J=8.8 Hz, 1H), 7.53 (d, J=2.9 Hz, 1H), 7.40 (d, J=8.5 Hz, 2H), 7.33-7.26 (m, 3H), 4.13 (t, J=7.4 Hz, 2H), 3.84 (s, 3H), 2.93 (t, J=7.4 Hz, 2H), 1.45 (s, 6H); $^{13}$C NMR (151 MHz, DMSO-$d_6$) δ 176.3, 163.1, 158.0, 142.6, 142.2, 137.2, 129.1, 127.4, 125.6, 124.1, 121.5, 110.5, 55.3, 42.3, 40.4, 32.9, 28.8; HRMS (ESI-TOF) m/z calcd for $C_{20}H_{21}N_2O_5S$ [M−H]⁻ 401.1177, found 401.1174; LC-MS m/z: 403.1 [M+H]⁺, purity>95% (ELSD).

Intermediate I-9: Methyl 3-sulfamoylbenzoate

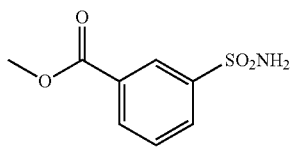

Methyl 3-(chlorosulfonyl)benzoate (1.00 g, 4.26 mmol) was dissolved in anhydrous tetrahydrofuran (15 mL) and the solution was cooled to 0° C. Aqueous ammonia (5.0 mL) was added drop-wise and the mixture stirred at ambient temperature for 2 h. Upon completion the reaction mixture was poured into chilled water and extracted with ethyl acetate. The combined organic extracts were washed with brine, dried ($Na_2SO_4$) and concentrated in vacuo. The resulting solid was triturated with pentane to afford the titled compound as a light brown solid (0.75 g, 82%). $^1$H NMR (400 MHz, DMSO-$d_6$): δ=8.40 (s, 1H), 8.19 (d, J=8 Hz, 1H), 8.1 (d, J=8 Hz, 1H), 7.77 (t, J=8 Hz, 1H), 7.6 (s, 2H), 3.92 (s, 3H); m/z 214.0 [M−H⁺]⁻.

Intermediate I-12: N-(3-Sulfamoylphenyl)pent-4-ynamide

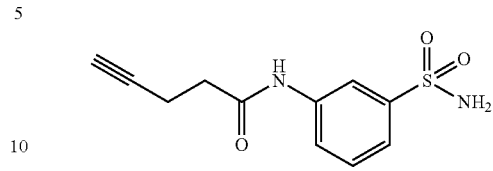

To a solution of pent-4-ynoic acid (0.1 g, 1.02 mmol) and 3-aminobenzenesulfonamide (0.21 g, 1.22 mmol) in dry DMF (5.0 ml) was added HBTU (0.46 g, 1.22 mmol) followed by DIPEA (212 uL, 1.22 mmol). The reaction mixture was stirred at ambient temperature for 2 h, or until completion. The mixture was diluted with EtOAc (30 mL), washed with $H_2O$ (20 mL), brine (20 mL) then the organics dried (MgSO₄) and concentrated in vacuo. The crude product was purified by column chromatography on silica gel using 100% hexanes eluant to give the titled compound as a to give the titled compound as a pale-yellow solid (0.2 g, 79%). $^1$H NMR (400 MHz, CD₃OD) δ=8.22 (dd, J=2.2, 1.7 Hz, 1H), 7.75-7.68 (m, 1H), 7.65-7.58 (m, 1H), 7.51-7.42 (m, 2H), 2.64-2.59 (m, 2H), 2.58-2.54 (m, 2H), 2.32-2.25 (m, 1H). $^{13}$C NMR (101 MHz, CD₃OD) δ=171.3, 143.8, 138.9, 129.2, 122.9, 121.0, 117.1, 82.1, 69.1, 35.4, 14.0.

Intermediate I-13: N-(Prop-2-yn-1-yl)-3-(4-sulfamoylphenyl)propanamide

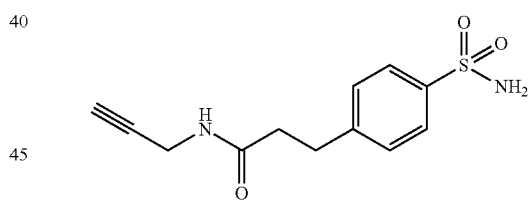

To a solution of 3-(4-sulfamoylphenyl)propanoic acid (0.3 g, 1.5 mmol) and propargyl amine (0.11 g, 1.5 mmol) in dry DMF (5.0 ml) was added HBTU (0.74 g, 1.5 mmol) followed by DIPEA (342 uL, 1.22 mmol). The reaction mixture was stirred at RT for 2 h. The reaction was monitored by LCMS and after the completion of reaction, it was diluted with EtOAc (30 mL) washed with H2O (20 mL), brine (20 mL). The organic layer was separated; dried (MgSO₄) and evaporated to give the crude product. The crude product was purified by silica gel column chromatography (1:1, EtOAc:Hexane) to isolate the title compound as a white solid (0.22 g, 63%). $^1$H NMR (400 MHz, CD₃OD) δ=7.85 (d, J=7.9 Hz, 2H), 7.38 (d, J=7.9 Hz, 2H), 3.97 (t, J=2.4 Hz, 2H), 3.04 (t, J=7.6 Hz, 2H), 2.55 (t, J=7.6 Hz, 2H), 2.33 (d, J=2.8 Hz, 1H).

91

Intermediate I-14: 2-(Methyl(7-nitrobenzo[c][1,2,5]oxadiazol-4-yl)amino)-N-(4-sulfamoylphenethyl)acetamide

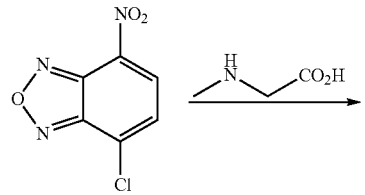

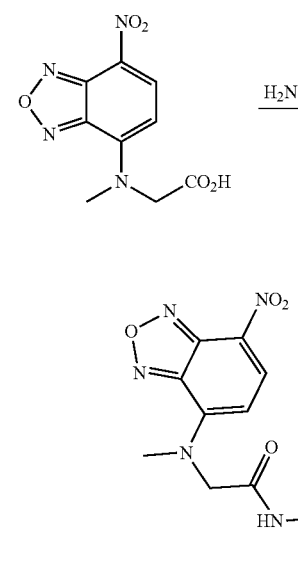

2-(Methylamino)acetic acid (0.24 g, 2.75 mmol) and sodium hydrogencarbonate (0.694 g, 8.26 mmol) were dissolved in a mixture of water (10 mL) and MeOH (20 mL). Then, 4-chloro-7-nitrobenzo[c][1,2,5]oxadiazole (0.50 g, 2.50 mmol) was added and the mixture stirred at 60° C. for 2 h. Upon completion of the reaction, volatiles were removed under reduced pressure and the crude residue obtained was purified by column chromatography on silica gel using 0-5% gradient of methanol in dichloromethane to obtain 2-(methyl(7-nitrobenzo[c][1,2,5]oxadiazol-4-yl)amino)acetic acid as a brick-red solid (1.10 g, 87%).

2-(Methyl(7-nitrobenzo[c][1,2,5]oxadiazol-4-yl)amino)acetic acid (1.00 g, 3.96 mmol) was dissolved in anhydrous tetahydrofuran (25 mL) under nitrogen atmosphere and the solution was cooled to 0° C. Diisopropylethylamine (0.76 g, 5.55 mmol) and 1,1'-carbonyldiimidazole (0.90 g, 4.75 mmol) were added and the mixture stirred at 50° C. until all of the 2-(methyl(7-nitrobenzo[c][1,2,5]oxadiazol-4-yl)amino)acetic acid had reacted. The reaction mixture was then cooled to 0° C., 4-(2-aminoethyl)-benzenesulfonamide (0.95 g, 4.75 mmol) was added and stirred at ambient temperature until completion, typically 6 h. The solvents were removed in vacuo and the residue was purified by reverse phase preparative HPLC to afford the titled compound as a brick-red solid (1.20 g, 70%). LCMS (m/z): 435.4 (M+1)+.

92

Intermediate I-15: 2-(7-(Dimethylamino)-2-oxo-2H-chromen-4-yl)-N-(4-sulfamoylphenethyl)acetamide

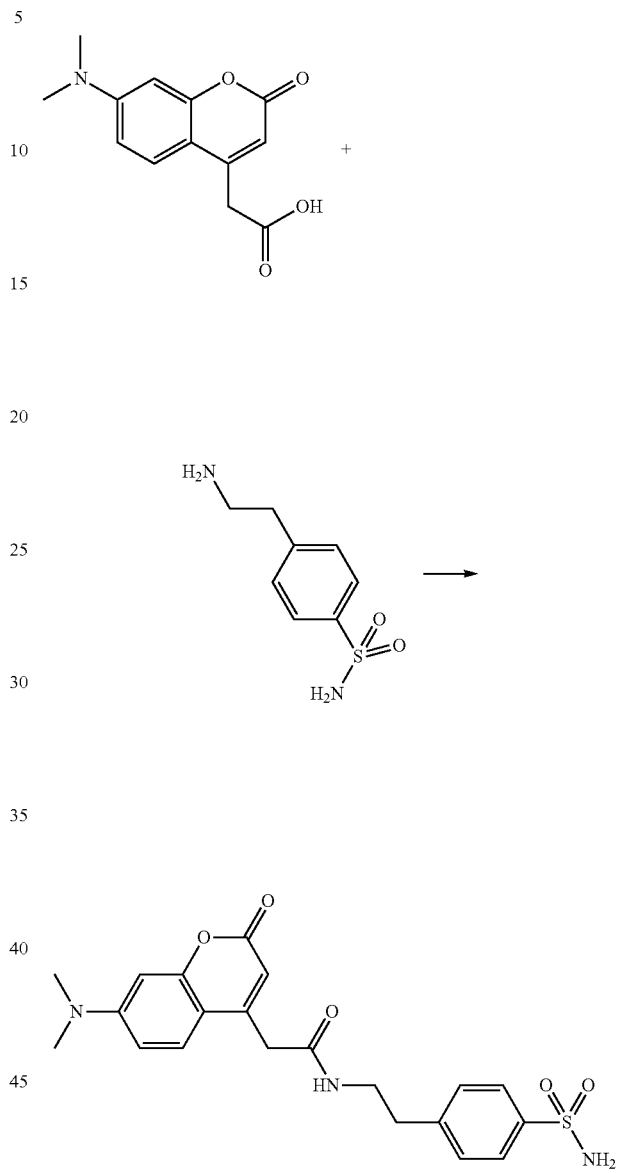

2-(7-(dimethylamino)-2-oxo-2H-chromen-4-yl)acetic acid (0.50 g, 2.02 mmol), EDC-HC (0.47 g, 3.03 mmol), HOBt (0.464 g, 3.03 mmol) and N-methylmorpholine (0.409 g, 4.04 mmol) were mixed in anhydrous tetrahydrofuran (5 mL) and stirred at 0° C. for 30 min. 4-(2-Aminoethyl)benzenesulfonamide (0.445 g, 2.224 mmol) was added and stirring continued at ambient temperature for 18 h. Upon completion, the reaction was poured onto chilled water and extracted with ethyl acetate. The solvent was removed in vacuo and the residue was purified by column chromatography on silica gel using a gradient of 0-5% methanol in dichloromethane to give 2-(7-(dimethylamino)-2-oxo-2H-chromen-4-yl)-N-(4-sulfamoylphenethyl)acetamide as a greenish-yellow solid (0.25 g, 29%). LCMS (m/z): 430.2 (M+1)+.

Intermediate 1-16: 3,5,6,7-Tetrahydro-2H-indeno[5,6-b]furan-8-amine

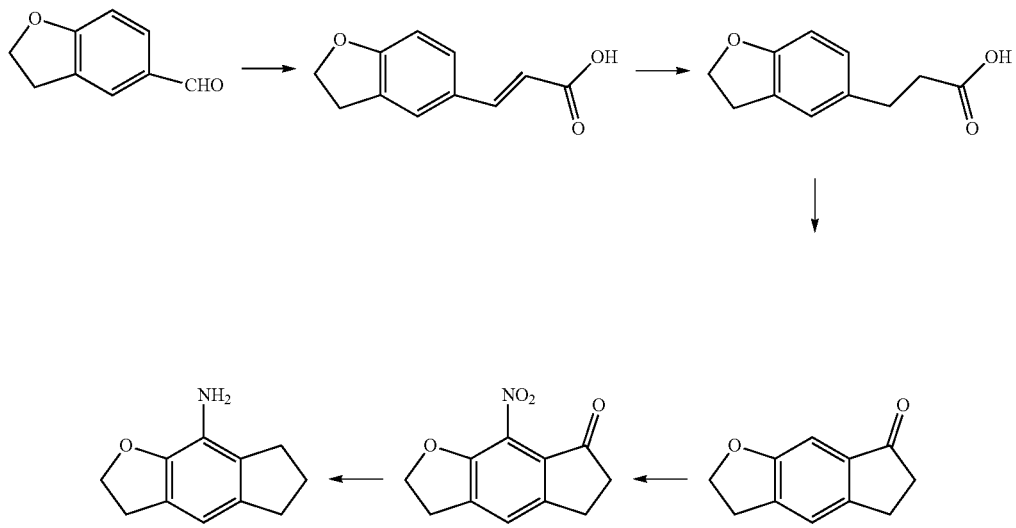

A solution of 2,3-dihydrobenzofuran-5-carbaldehyde (10 g, 67.6 mmol), malonic acid (10.5 g, 101.35 mmol) and piperidine (0.47 mL, 4.73 mmol, 0.07 eq) was heated in pyridine (60 mL) at 100° C. for 5 h. The reaction mixture was acidified to ~pH 3 using 1N HCl and the product extracted using 10% IPA/chloroform (2×250 mL). The combined organic extracts were washed with water (250 mL), brine (250 mL), dried ($Na_2SO_4$) and concentrated in vacuo. The crude product was triturated using diethyl ether to give (E)-3-(2,3-dihydrobenzofuran-5-yl)acrylic acid as a yellow solid (10 g, 78%). $^1$H NMR (300 MHz, Chloroform-d) δ=7.73 (d, J=15.9 Hz, 1H), 7.43 (s, 1H), 7.33 (dd, J=8.1, 1.8 Hz, 1H), 6.80 (d, J=8.1 Hz, 1H), 6.29 (d, J=15.9 Hz, 1H), 4.64 (t, J=8.7 Hz, 2H), 3.24 (t, J=8.7 Hz, 2H).

A solution of (E)-3-(2,3-dihydrobenzofuran-5-yl)acrylic acid (8.0 g, 42.1 mmol) in acetic acid (80 mL) and water (1.0 mL) was treated with 10% palladium on carbon (1.0 g) in two portions. The reaction mixture was stirred under an atmosphere or hydrogen gas (balloon) until completion, typically 4 h. The mixture was diluted using ethyl acetate (100 mL) and filtered through a bed of celite washing through with further ethyl acetate. The solvents were removed in vacuo and the crude residue azeotroped using toluene (2×50 mL) to give an off white solid which was triturated using diethyl ether (50 mL) to give 3-(2,3-dihydrobenzofuran-5-yl)propanoic acid as a white solid (6.5 g, 80%). $^1$H NMR (400 MHz, CDCl$_3$) δ=7.04 (s, 1H), 6.93 (d, J=8.4, 1H), 6.7 (d, J=8.4 Hz, 1H), 4.55 (t, J=8.4 Hz, 2H), 3.18 (t, J=8.4 Hz, 2H), 2.89 (t, J=7.6 Hz, 2H), 2.64 (t, J=7.6 Hz, 2H).

A solution of 3-(2,3-dihydrobenzofuran-5-yl)propanoic acid (6.0 g, 31 mmol) in thionyl chloride (8 mL) was heated at 80° C. for 1 h. On completion of the reaction the thionyl chloride was removed in vacuo and the crude 3-(2,3-dihydrobenzofuran-5-yl)propanoyl chloride dissolved in anhydrous 1,2-dichloroethane (30 mL). In a separate flask aluminium trichloride (2 g, 15 mmol) was added to anhydrous 1,2-dichloroethane (40 mL) at 0° C. followed by the acid chloride solution (10 mL) drop-wise over 5 min and the resulting solution was stirred for 30 min at 0° C. A further portion of aluminium trichloride (3 g, 22.5 mmol) was added followed by drop-wise addition of the remaining acid chloride solution (20 mL) at 0° C. The reaction mixture was stirred at room temperature for 1 h or until completion, diluted with water and extracted using EtOAc (2×50 mL). The combined organic extracts were washed with 1N HCl (50 mL), 1N NaOH (50 mL), water (25 mL), brine (25 mL), dried ($Na_2SO_4$) and concentrated in vacuo. The crude product was purified by column chromatography on silica gel using 10% EtOAc-hexanes eluent to give 2,3,5,6-tetrahydro-7H-indeno[5,6-b]furan-7-one as a white solid (3.8 g, 70%). $^1$H NMR (300 MHz, CD$_3$OD) δ=7.36 (s, 1H), 6.91 (s, 1H), 4.61 (t, J=8.6 Hz, 3H), 3.26 (t, J=8.6 Hz, 2H), 3.05 (t, J=5.5 Hz, 3H), 2.68 (t, J=5.5 Hz, 2H).

2,3,5,6-tetrahydro-7H-indeno[5,6-b]furan-7-one (1.5 g, 8.61 mmol) was dissolved in c·H$_2$SO$_4$ (6.0 mL) at 0° C. followed by drop-wise addition of f·HNO$_3$:c·H$_2$SO$_4$, 1:1 (1.2 mL) stirring was continued at 0° C. for 1 h. The reaction mixture was added to ice-cold water (60 mL) and stirred for 10 min, the resulting light brown ppt was removed by filtration, washed with ice cold water (20 mL) and dried in vacuo to give 8-nitro-2,3,5,6-tetrahydro-7H-indeno[5,6-b]furan-7-one (1.2 g, 64%). $^1$H NMR (300 MHz, CD$_3$OD) δ=7.54 (s, 1H), 4.80 (t, J=8.6 Hz, 2H), 3.42 (t, J=8.6 Hz, 2H), 3.09 (t, J=5.6 Hz, 2H), 2.74 (t, J=5.6 Hz, 2H).

A solution of 8-nitro-2,3,5,6-tetrahydro-7H-indeno[5,6-b]furan-7-one (1.0 g, 4.57 mmol) in methanol (20 mL) 0° C. was treated with methane sulfonic acid (0.2 mL) followed by 20% palladium hydroxide (0.5 g). The reaction mixture was stirred under an atmosphere or hydrogen gas at 60 psi until completion. The reaction mixture was filtered through a bed of celite washing through with methanol (50 mL) and concentrated in vacuo. The residue was diluted with ethyl acetate (50 mL) and washed using sat. aq. NaHCO$_3$ (50 mL), water (20 mL), brine (20 mL), dried (Na$_2$SO$_4$) and concentrated in vacuo. The crude product was purified by column chromatography on silica gel using 10% EtOAc-hexanes eluent to give 3,5,6,7-tetrahydro-2H-indeno[5,6-b]furan-8-amine as a white solid (0.5 g, 63%). $^1$H NMR (300 MHz, CDCl$_3$) δ=6.54 (s, 1H), 5.30 (s, 2H), 4.61 (t, J=8.7 Hz, 2H), 3.21 (t, J=8.7 Hz, 2H), 2.95 (t, J=5.5 Hz, 2H), 2.66 (t, J=5.5 Hz, 2H).

Intermediate I-17:
Benzo[1,2-b:4,5-b']difuran-4-amine

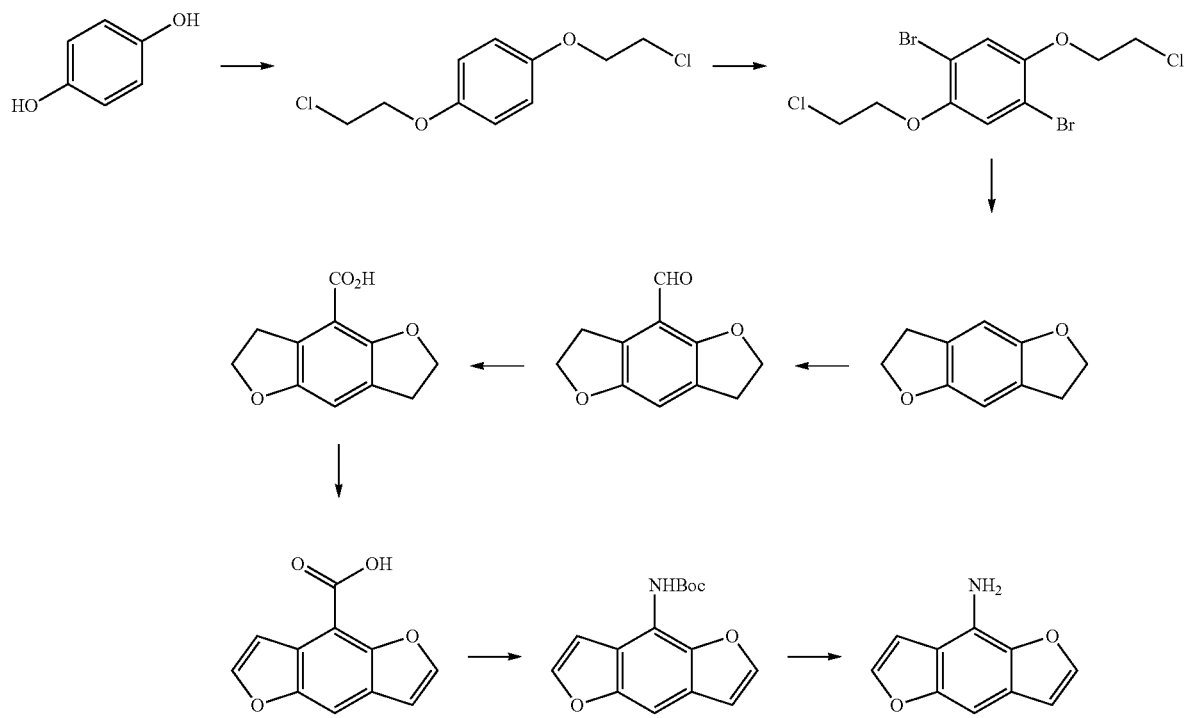

Synthesis of 2,3,6,7-tetrahydrobenzo[1,2-b:4,5-b']difuran-4-carboxylic acid was carried out from hydroquinone using procedures detailed by Monte et al., J. Med. Chem., 1996, 39, 2953-2961 to give the 2,3,6,7-tetrahydrobenzo[1,2-b:4,5-b']difuran-4-carbaldehyde as a bright yellow solid; $^1$H NMR (400 MHz, CDCl$_3$): δ=10.27 (s, 1H), 6.87 (s, 1H), 4.67 (t, J=8.8 Hz, 2H), 4.59 (t, J=8.8 Hz, 2H), 4.59 (t, J=8.8 Hz, 2H), 3.46 (t, J=8.8 Hz, 2H), 3.18 (t, J=8.8 Hz, 2H).

The aldehyde (0.68 g, 3.58 mmol) was oxidized using silver (I) oxide (1.5 eq.) in 5% aqueous sodium hydroxide at rt for 20 days. The crude reaction mixture was filtered through celite, extracted using diethyl ether (2×50 mL) to remove unreacted aldehyde then the aqueous phase was acidified to pH 1 using 3.0 M aqueous HCl drop-wise at 0° C. The product was extracted using dichloromethane (2×50 mL) and the combined organics washed using brine (50 mL), dried (MgSO$_4$) and concentrated in vacuo to give 2,3,6,7-tetrahydrobenzo[1,2-b:4,5-b']difuran-4-carboxylic acid as a white solid (0.44 g; 60%).

Alternatively, the aldehyde (0.5 g, 2.77 mmol) in acetone (5.0 mL) was treated with sulfamic acid (0.4 g, 4.17 mmol) in two portions at 0° C. After 2 min a solution of sodium chlorite (0.32 g, 3.6 mmol) in water (1.0 mL) was added drop-wise and stirring continued at 0° C. for 4 h. The reaction mixture was diluted with water (20 mL) and extracted using 10% IPA/chloroform (2×20 mL). The combined organics were washed with water (25 mL), brine (25 mL), dried (Na$_2$SO$_4$) and concentrated in vacuo. The crude solid was triturated with diethyl ether to give 2,3,6,7-tetrahydrobenzo[1,2-b:4,5-b']difuran-4-carboxylic acid (0.4 g; 70%). $^1$H NMR (400 MHz, DMSO-d$_6$): δ=6.86 (s, 1H), 4.52 (t, J=8.8 Hz, 2H), 4.47 (t, J=8.8 Hz, 2H), 3.30 (t, J=8.8 Hz, 2H), 3.10 (t, J=8.8 Hz, 2H). $^{13}$C (100 MHz, DMSO-d$_6$): δ=166.4, 154.2, 153.9, 128.9, 127.2, 111.4, 110.43, 71.9, 71.6, 31.5, 29.5.

2,3,6,7-tetrahydrobenzo[1,2-b:4,5-b']difuran-4-carboxylic acid (0.8 g, 3.88 mmol), 2,3-dichloro-5,6-dicyanobenzoquinone (2.64 g, 11.65 mmol) in anhydrous dioxane (20 mL) was heated in a sealed tube at 120° C. for 18 h. The reaction mixture was cooled to room temperature and sat. aq. Na$_2$S$_2$O$_3$ (30 mL) added before extraction with ethyl acetate (2×25 mL). The combined organics dried (Na$_2$SO$_4$) and concentrated in vacuo to give the crude benzo[1,2-b:4,5-b']difuran-4-carboxylic acid (1.5 g). The crude acid (1.5 g), triethylamine (2.05 mL) and diphenylphosphoryl azide (4.08 g, 14.85 mmol) in tertiary butanol (20 mL) was heated in a sealed tube at 90° C. for 12 h. The solution was cooled to room temperature, diluted with water (50 mL) and extracted using EtOAc (2×50 mL). The combined organic extracts were washed with water (25 mL), brine (25 mL), dried (Na$_2$SO$_4$) and concentrated in vacuo. The crude product was purified by column chromatography on silica gel using 10% EtOAc-hexanes eluent to give tert-butyl benzo[1,2-b:4,5-b']difuran-4-ylcarbamate (0.75 g) with minor impurities from the phosphine reagent, the product was dissolved in DCM (10 mL) and TFA (3.0 mL) added drop-wise over 5 min at 0° C. The reaction was stirred at ambient temperature for 2 h then added carefully to sat. aq. NaHCO$_3$ (50 mL). The aqueous phase was extracted using DCM (2×30 mL) and the combined organic extracts were washed with water (25 mL), brine (25 mL), dried (Na$_2$SO$_4$) and concentrated in vacuo. The crude product was purified by column chromatography on silica gel using 10% EtOAc-hexanes eluent to give benzo[1,2-b:4,5-b']difuran-4-amine as an off-white solid (0.2 g, 30% over three steps). $^1$H NMR (400 MHz, CDCl$_3$): δ=7.6 (d, J=2.2 Hz, 1H), 7.53 (d, J=2.2 Hz, 1H), 7.12 (s, 1H), 6.78 (m, 2H), 4.17 (br.s., 1H).

Intermediate I-23: 4-(2-Aminoethyl)-N-((1,2,3,5,6,7-hexahydro-s-indacen-4-yl)carbamoyl)benzenesulfonamide Step A: tert-Butyl (4-sulfamoylphenethyl)carbamate

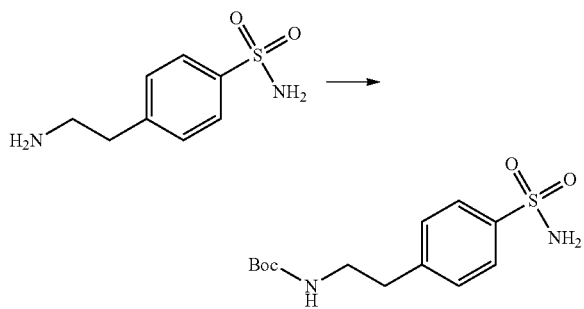

To a solution of 4-(2-aminoethyl)benzenesulfonamide (5 g, 24.97 mmol) in THF (100 mL) was added Boc$_2$O (6.5 g, 29.96 mmol, 6.88 mL) and triethylamine (5-18, 49.94 mmol, 6.95 mL). The mixture was stirred at 25° C. for 2 hours before the reaction was quenched with water (100 mL) and extracted into dichloromethane (3×150 mL). The combined organic extracts were washed with brine (2×100 mL), dried (Na$_2$SO$_4$), filtered and concentrated in vacuo. The crude product was triturated with ethyl acetate (100 mL) and then isolated by filtration to afford the title compound as yellow solid (7.0 g, 93% yield). The crude product was used in next step directly without further purification.

$^1$H NMR (DMSO-d$_6$) δ 7.75-7.73 (d, 2H), 7.39-7.37 (d, 2H), 7.30 (s, 2H), 6.93 (s, 1H), 3.17-3.14 (m, 2H), 2.79-2.75 (m, 2H) and 1.37 (s, 9H).

LCMS: m/z 323.0 (M+Na)$^+$

Step B: tert-Butyl 4-(N-((1,2,3,5,6,7-hexahydro-s-indacen-4-yl)carbamoyl)sulfamoyl)-phenethylcarbamate

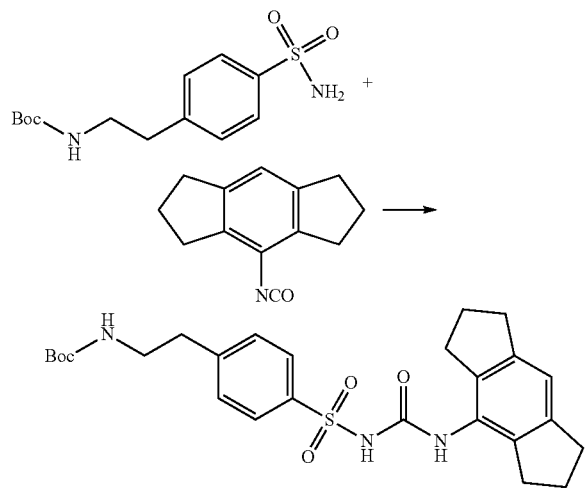

To a mixture of tert-butyl (4-sulfamoylphenethyl)carbamate (3.0 g, 10.0 mmol) in THF (30 mL) was added sodium methoxide (539.6 mg, 10.0 mmol). The mixture was stirred at 25° C. for 2 hours and then 4-isocyanato-1,2,3,5,6,7-hexahydro-s-indacene (3.0 g, 12.0 mmol) in THF (10 mL) was added drop-wise. The mixture was stirred at 70° C. for another 0.5 hours before the reaction was quenched with water (30 mL) and then adjusted pH to 5-6 with hydrochloric acid (1 M). The resulting solid was filtered and dried in vacuo to afford the title compound as white solid (4.2 g, 84% yield). The crude product was used in next step directly without further purification.

$^1$H NMR (DMSO-d$_6$) δ 10.64 (s, 1H) 8.08 (s, 1H), 7.86-7.84 (d, 2H), 7.44-7.42 (d, 2H), 6.93 (s, 2H), 3.18-3.17 (m, 2H), 2.81-2.75 (m, 7H), 2.54-2.52 (m, 3H), 1.98-1.88 (m, 4H) and 1.35 (s, 9H)

LCMS: m/z 444.1 (M+H−56)$^+$

Step C: 4-(2-Aminoethyl)-N-((1,2,3,5,6,7-hexahydro-s-indacen-4-yl)-carbamoyl)-benzenesulfonamide

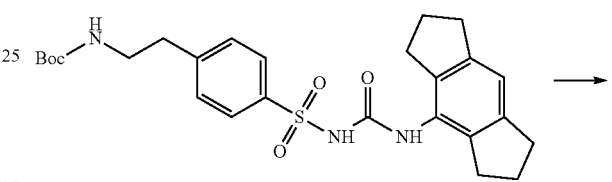

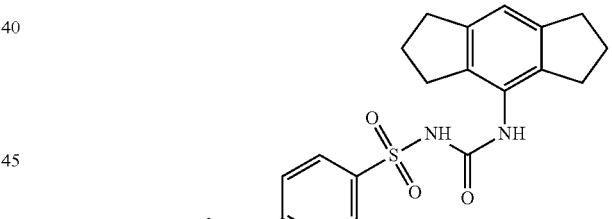

To a solution of tert-butyl 4-(N-((1,2,3,5,6,7-hexahydro-s-indacen-4-yl)carbamoyl)-sulfamoyl)phenethylcarbamate (4.2 g, 8.4 mmol) in dichloromethane (25 mL) was added a solution of hydrogen chloride in ethyl acetate (25 mL, 100.0 mmol). The reaction was allowed to stir at 25° C. for 2 hours before the mixture was poured into water (50 mL) and then adjusted to pH 7 with aqueous sodium hydroxide solution (1 M). The resulting precipitate was filtered and washed with methanol (20 mL) to afford the title compound, Intermediate I-23 (2.8 g, 75% yield) as a white solid. 1H NMR (DMSO-d$_6$) δ 10.97 (s, 1H) 8.55 (s, 1H), 7.92 (s, 2H) 7.82-7.80 (d, 2H), 7.44-7.42 (d, 2H), 6.83 (s, 2H), 2.98-2.91 (m, 2H), 2.89-2.70 (m, 2H), 2.68-2.63 (m, 5H), 2.61-2.59 (m, 2H) and 1.85-1.81 (m, 4H).

LCMS m/z 400.1 (M+H)$^+$

Sulfonylurea Synthesis

Example 1: 4-Acetyl-N-((1,2,3,5,6,7-hexahydro-s-indacen-4-yl)carbamoyl) benzenesulfonamide

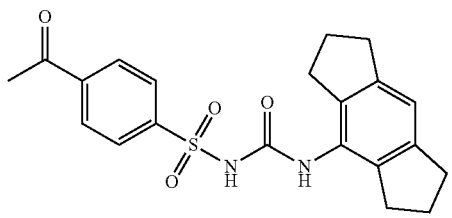 [SMILES: CC(=O)c1ccc(S(=O)(=O)NC(=O)Nc2c3c(cc4c2CCC4)CCC3)cc1]

4-Acetylbenzenesulfonamide (100 mg, 0.50 mmol) was treated as per general method A to afford the titled compound as a white solid (31 mg, 16%): $^1$H NMR (600 MHz, DMSO-$d_6$) δ 11.03 (br s, 1H), 8.08 (d, J=8.5 Hz, 2H), 7.99 (d, J=8.5 Hz, 2H), 7.07 (br s, 1H), 6.87 (s, 1H), 2.75 (t, J=7.4 Hz, 4H), 2.62 (s, 3H), 2.56 (t, J=7.4 Hz, 4H), 1.90 (p, J=7.4 Hz, 4H); $^{13}$C NMR (151 MHz, DMSO-$d_6$) δ 197.3, 151.8, 142.6, 138.9, 136.9, 129.7, 128.2, 127.2, 117.1, 32.4, 30.1, 26.9, 24.9; HRMS (ESI-TOF) m/z calcd for $C_{21}H_{21}N_2O_4S$ [M−H]$^−$ 397.1228, found 397.1225; LC-MS m/z 399.1 [M+H]$^+$, purity>95% (ELSD).

Example 2: 5-Chloro-N-(4-(N-((1,2,3,5,6,7-hexahydro-s-indacen-4-yl)carbamoyl) sulfamoyl)phenethyl)-2-methoxybenzamide

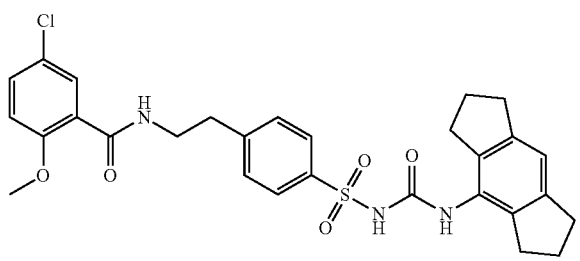 [SMILES: COc1ccc(Cl)cc1C(=O)NCCc1ccc(S(=O)(=O)NC(=O)Nc2c3c(cc4c2CCC4)CCC3)cc1]

5-Chloro-2-methoxy-N-(4-sulfamoylphenethyl) benzamide (300 mg, 0.81 mmol) was treated as per general method A to afford the titled compound as a white solid (325 mg, 70%); $^1$H NMR (600 MHz, DMSO-$d_6$) δ 10.74 (br s, 1H), 8.27 (t, J=5.7 Hz, 1H), 8.01 (s, 1H), 7.86 (d, J=8.3 Hz, 2H), 7.65 (d, J=2.8 Hz, 1H), 7.50 (dd, J=8.9, 2.8 Hz, 1H), 7.47 (d, J=8.3 Hz, 2H), 7.13 (d, J=8.9 Hz, 1H), 6.89 (s, 1H), 3.78 (s, 3H), 3.59-3.49 (m, 2H), 2.92 (t, J=7.1 Hz, 2H), 2.75 (t, J=7.4 Hz, 4H), 2.53 (t, J=7.4 Hz, 4H), 1.89 (p, J=7.5 Hz, 4H); $^{13}$C NMR (151 MHz, DMSO-$d_6$) δ 163.5, 155.6, 153.8, 144.4, 142.8, 136.9, 136.9, 131.4, 129.4, 129.4, 128.9, 127.1, 124.6, 124.2, 117.4, 114.0, 56.1, 40.2, 34.6, 32.3, 30.0, 24.9; HRMS (ESI-TOF) m/z calcd for $C_{29}H_{29}ClN_3O_5S$ [M−H]$^−$ 566.1522, found 566.1543; LC-MS m/z 566.2 [M−H]$^−$, purity>95% (ELSD).

Example 3: N-(4-(N-((1,2,3,5,6,7-Hexahydro-s-indacen-4-yl)carbamoyl)sulfamoyl) phenethyl)-5-methylpyrazine-2-carboxamide

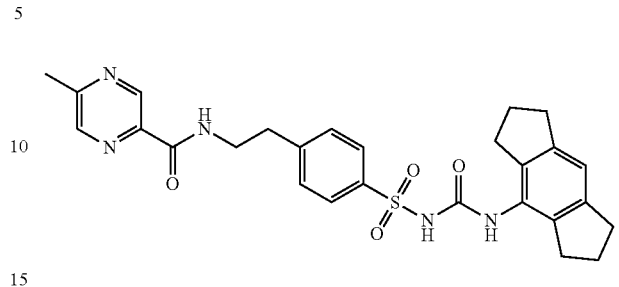

5-Methyl-N-(4-sulfamoylphenethyl)pyrazine-2-carboxamide (Intermediate I-3) (100 mg, 0.312 mmol) was treated as per general method A to afford a crude white solid (72 mg). Further purification by HPLC yielded a white solid (14 mg, 9%). $^1$H NMR (600 MHz, DMSO-$d_6$) δ 10.79 (br s, 1H), 9.03 (d, J=1.4 Hz, 1H), 8.96 (t, J=6.0 Hz, 1H), 8.59 (m, 1H), 7.79 (d, J=8.3 Hz, 2H), 7.47 (d, J=8.3 Hz, 2H), 7.30 (s, 1H), 6.86 (s, 1H), 3.58-3.52 (m, 2H), 2.94 (t, J=7.3 Hz, 2H), 2.75 (t, J=7.5 Hz, 4H), 2.58 (br s, 3H), 2.54 (t, J=7.5 Hz, 4H), 1.88 (p, J=7.5 Hz, 4H); $^{13}$C NMR (151 MHz, DMSO-$d_6$) δ 162.8, 156.7, 152.1, 143.4, 142.7, 142.6, 142.3, 141.9, 136.8, 129.9, 129.0, 128.5, 126.9, 125.6, 117.0, 40.0, 34.6, 32.4, 30.1, 24.9, 21.2; HRMS (ESI-TOF) m/z calcd for $C_{27}H_{30}N_5O_4S$ [M+H]$^+$ 520.2020, found 520.2030; LC-MS m/z 518.2 [M−H]$^−$, purity>95% (ELSD).

Example 4: N-(4-(N-((1,2,3,5,6,7-Hexahydro-s-indacen-4-yl)carbamoyl)sulfamoyl) phenethyl)-5-methylisoxazole-3-carboxamide

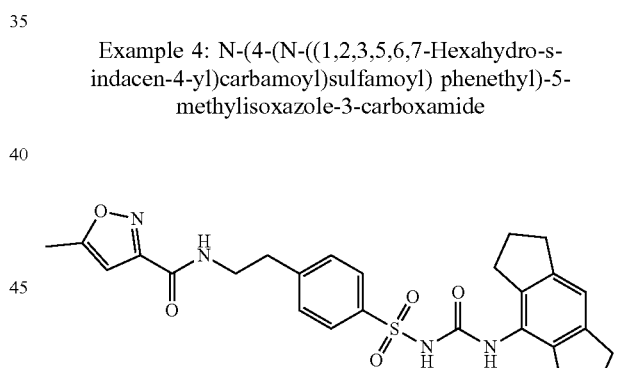

5-Methyl-N-(4-sulfamoylphenethyl) isoxazole-3-carboxamide (Intermediate I-4) (14 mg, 0.044 mmol) was treated as per general method A. Further MPLC purification using 0.05% formic acid$_{(aq)}$/0.05% formic acid in CH$_3$CN gradient elution. Lyophilisation of the appropriate fractions afforded the titled compound as a white solid (14 mg, 62%): $^1$H NMR (600 MHz, DMSO-$d_6$) δ 10.73 (br s, 1H), 8.81 (t, J=5.8 Hz, 1H) 8.09 (s, 1H), 7.86 (d, J=8.2 Hz, 2H), 7.47 (d, J=8.2 Hz, 2H), 6.92 (s, 1H), 6.49 (s, 1H), 3.49 (m, 2H), 2.93 (t, J=7.2 Hz, 2H), 2.76 (t, J=7.2 Hz, 4H), 2.52 (m, 4H), 2.44 (s, 3H), 1.90 (p, J=7.2 Hz, 4H); $^{13}$C NMR (151 MHz, DMSO) δ 171.0, 158.7, 158.5, 148.9, 145.0, 142.9, 137.8, 137.1, 129.1, 128.5, 127.2, 117.9, 101.1, 39.7, 34.4, 32.3, 29.9, 24.9, 11.70; HRMS (ESI-TOF) m/z calcd for $C_{26}H_{27}N_4O_5S$ [M−H]$^−$ 507.1708, found 507.1709; LC-MS m/z 509.4 [M+H]$^+$, purity>95% (ELSD).

Example 5: N-((1,2,3,5,6,7-Hexahydro-s-indacen-4-yl)carbamoyl)-4-(2-(7-methoxy-4,4-dimethyl-1,3-dioxo-3,4-dihydroisoquinolin-2(1H)-yl)ethyl)benzenesulfonamide

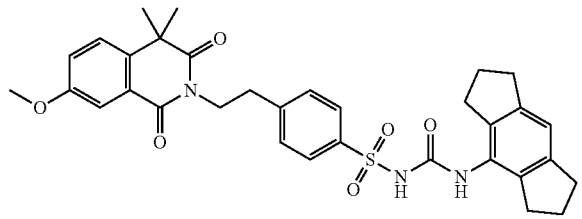 [SMILES: COc1ccc2c(c1)C(=O)N(CCc1ccc(S(=O)(=O)NC(=O)Nc3c4c(cc5c3CCC5)CCC4)cc1)C(=O)C2(C)C]

4-(2-(7-Methoxy-4,4-dimethyl-1,3-dioxo-3,4-dihydroisoquinolin-2(1H)-yl)ethyl)benzene sulfonamide (Intermediate I-5) (111 mg, 0.276 mmol) was treated as per general method A to afford the titled compound as a white solid (85 mg, 52%): $^1$H NMR (600 MHz, DMSO-d$_6$) δ 10.72 (br s, 1H), 7.91 (s, 1H), 7.80 (d, J=8.0 Hz, 2H), 7.58 (d, J=8.7 Hz, 1H), 7.53 (d, J=2.9 Hz, 1H), 7.39 (d, J=8.0 Hz, 2H), 7.29 (dd, J=8.7, 2.9 Hz, 1H), 6.88 (s, 1H), 4.13 (t, J=7.5 Hz, 2H), 3.83 (s, 3H), 2.93 (t, J=7.4 Hz, 2H), 2.76 (t, J=7.4 Hz, 4H), 2.55 (t, J=7.4 Hz, 4H), 1.90 (p, J=7.4 Hz, 4H), 1.42 (s, 6H); $^{13}$C NMR (151 MHz, DMSO) δ 176.3, 163.1, 158.0, 150.1, 143.5, 142.8, 137.1, 136.9, 129.1, 129.0, 127.4, 127.1, 125.6, 124.1, 121.4, 117.4, 110.4, 55.3, 42.3, 40.3, 33.0, 32.3, 30.0, 28.8, 24.9; HRMS (ESI-TOF) m/z calcd for C$_{33}$H$_{34}$N$_3$O$_6$S [M−H]$^-$ 600.2174, found 600.2183; LC-MS m/z 602.4 [M+H]$^+$, purity>95% (ELSD).

Example 6: 3-Ethyl-N-(4-(N-((1,2,3,5,6,7-hexahydro-s-indacen-4-yl)carbamoyl) sulfamoyl)phenethyl)-4-methyl-2-oxo-2,5-dihydro-1H-pyrrole-1-carboxamide

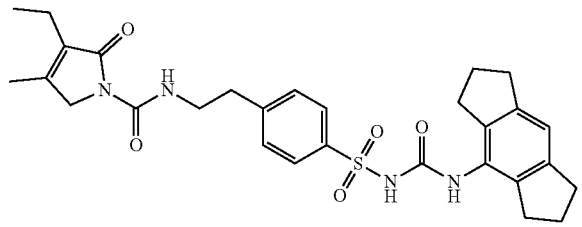 [SMILES: CCC1=C(C)CN(C(=O)NCCc2ccc(S(=O)(=O)NC(=O)Nc3c4c(cc5c3CCC5)CCC4)cc2)C1=O]

3-Ethyl-4-methyl-2-oxo-N-(4-sulfamoylphenethyl)-2,5-dihydro-1H-pyrrole-1-carboxamide (100 mg, 0.29 mmol) was treated as per general method A to afford the titled compound as a white solid (78 mg, 50%). $^1$H NMR (600 MHz, DMSO-d$_6$) δ 10.73 (br s, 1H), 8.38 (t, J=5.8 Hz, 1H), 8.04 (s, 1H), 7.84 (d, J=8.4 Hz, 2H,), 7.45 (d, J=8.4 Hz, 2H), 6.90 (s, 1H), 4.16 (s, 2H), 3.52-3.45 (m, 2H), 2.89 (t, J=7.2 Hz, 2H), 2.75 (t, J=7.5 Hz, 4H), 2.52 (d, J=7.4 Hz, 4H), 2.18 (q, J=7.5 Hz, 2H,), 2.00 (s, 3H), 1.90 (p, J=7.5 Hz, 4H), 0.97 (t, J=7.5 Hz, 3H). $^{13}$C NMR (151 MHz, DMSO-d$_6$) δ 171.8, 152.1, 151.7, 149.8, 144.7, 143.0, 138.6, 137.2, 131.9, 129.1, 129.0, 127.4, 117.8, 51.9, 40.2, 35.3, 32.5, 30.1, 25.0, 16.0, 12.9, 12.8. HRMS (ESI-TOF) m/z: calcd for C$_{29}$H$_{33}$N$_4$O$_5$S [M−H]$^-$ 549.2177; found 549.2169. LCMS: m/z 573.47 [M+Na]$^+$, purity>95% (ELSD).

Example 7: Ethyl 5-(N-((1,2,3,5,6,7-hexahydro-s-indacen-4-yl)carbamoyl)sulfamoyl)-furan-3-carboxylate

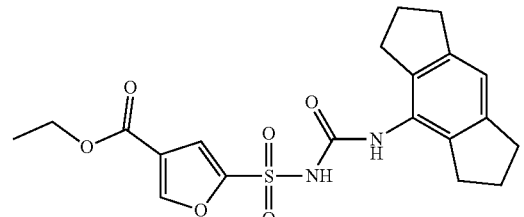

4-Isocyanato-1,2,3,5,6,7-hexahydro-s-indacene (prepared using general method A2) and ethyl 5-sulfamoylfuran-3-carboxylate were used in general method B1. The reaction mixture was quenched using water (50 mL), extracted using ethyl acetate (2×25 mL) and the organics washed with brine (25 mL), dried (Na$_2$SO$_4$) and concentrated in vacuo. The crude product was purified by column chromatography on silica gel using 50% EtOAc-hexanes eluent to give the titled compound as a white solid (0.45 g, 63%). $^1$H NMR (300 MHz, DMSO-d$_6$) δ=8.31 (s, 1H), 7.59 (s, 1H), 6.77 (s, 1H), 4.22 (q, J=7.2 Hz, 2H), 2.75 (t, J=7.3 Hz, 4H), 2.65 (t, J=7.3 Hz, 4H) 1.90 (pent, J=7.6 Hz, 4H), 1.26 (t, J=7.2 Hz, 3H).

Example 8: 5-(N-((1,2,3,5,6,7-hexahydro-s-indacen-4-yl)carbamoyl)sulfamoyl)furan-3-carboxylic acid

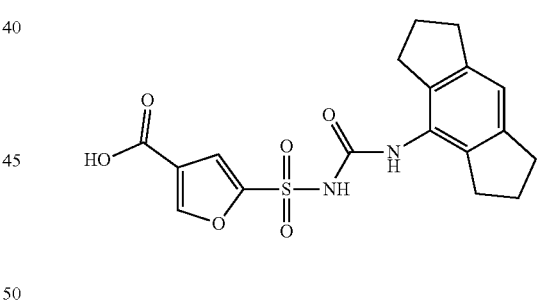

Ethyl 5-(N-((1,2,3,5,6,7-hexahydro-s-indacen-4-yl)carbamoyl)sulfamoyl)furan-3-carboxylate (Example 7) (0.1 g, 0.24 mmol) in THF (8 mL) at 0° C. was treated with a solution of LiOH (0.1 g, 2.4 mmol) in water (2 mL). The cooling bath was removed and the reaction mixture stirred for 3 h. The solution was acidified using 10% citric acid and immediately extracted using ethyl acetate (2×25 mL). The organics were washed using water (20 mL), brine (20 mL), dried (Na$_2$SO$_4$) and concentrated in vacuo. The crude product was purified by reversed phase HPLC to give the titled compound as a white solid (5.0 mg, 5%). $^1$H NMR (400 MHz, CD$_3$OD): δ=8.14 (s, 1H), 7.28 (s, 1H), 6.93 (s, 1H), 2.85 (t, J=7.6 Hz, 4H), 2.74 (t, J=7.6 Hz, 4H), 2.04 (quin, J=7.6 Hz, 4H).

Example 9: Methyl 3-(N-((1,2,3,5,6,7-hexahydro-s-indacen-4-yl)carbamoyl)-sulfamoyl)benzoate

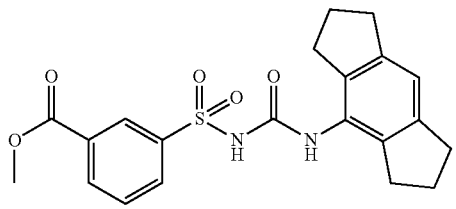 [SMILES: COC(=O)c1cccc(S(=O)(=O)NC(=O)Nc2c3c(cc4c2CCC4)CCC3)c1]

4-Isocyanato-1,2,3,5,6,7-hexahydro-s-indacene (prepared using general method A1) was added directly to methyl 3-sulfamoylbenzoate (Intermediate I-9) (0.447 g, 2.07 mmol, 1.20 equiv) at ambient temperature and the mixture was stirred overnight. The reaction mixture was poured into chilled water and extracted with ethyl acetate. The combined organic extracts were washed with brine, dried ($Na_2SO_4$) and concentrated in vacuo. The residue obtained was purified by column chromatography on silica gel using 0-10% gradient of methanol in dichloromethane to give methyl 3-(N-((1,2,3,5,6,7-hexahydro-s-indacen-4-yl)carbamoyl)sulfamoyl)benzoate as a light-brown solid (0.36 g, 50%).

Example 10: 3-(N-((1,2,3,5,6,7-Hexahydro-s-indacen-4-yl)carbamoyl)sulfamoyl)-benzoic acid

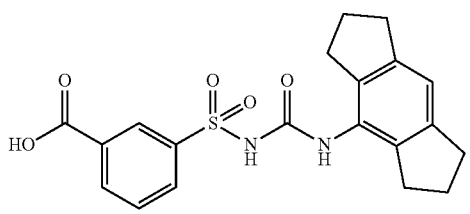 [SMILES: O=C(Nc1c2c(cc3c1CCC3)CCC2)NS(=O)(=O)c1cccc(C(=O)O)c1]

Methyl 3-(N-(1,2,3,5,6,7-hexahydro-s-indacen-4-ylcarbamoyl)sulfamoyl)benzoate (Example 9) (0.25 g, 0.603 mmol) was dissolved in a mixture of tetrahydrofuran:methanol:water (9 mL, 1:1:1) and the mixture was cooled to 0° C. Lithium hydroxide monohydrate (0.75 g, 1.81 mmol, 3 eq) was added and the mixture stirred at ambient temperature for 3 h. Upon completion, the reaction mixture was poured into chilled water and extracted with ethyl acetate. The combined organic extracts were washed with brine, dried ($Na_2SO_4$) and concentrated in vacuo. The product was purified by reverse phase preparative HPLC to afford the titled compound as a white solid (0.017 g, 3%). $^1$H NMR (400 MHz, DMSO-$d_6$): δ=13.26 (bs, 1H), 8.43 (s, 1H), 8.13-8.08 (m, 2H), 7.99 (bs, 1H), 7.67 (t, J=8.0 Hz, 1H), 6.87 (s, 1H), 6.52 (s, 1H), 2.75 (t, J=7.2 Hz, 4H), 2.55 (t, J=7.6 Hz, 4H), 1.89 (quin, J=7.6 Hz, 4H). LCMS, Purity: 96%, m/z 400.98 (M+H$^+$). HRMS (FAB$^+$) calcd for $C_{20}H_{20}N_2O_5S$ [M+H]$^+$: 401.1093, found: 401.4514.

Example 11: 3-(N-(1,2,3,5,6,7-Hexahydro-s-indacen-4-ylcarbamoyl)sulfamoyl)-benzamide

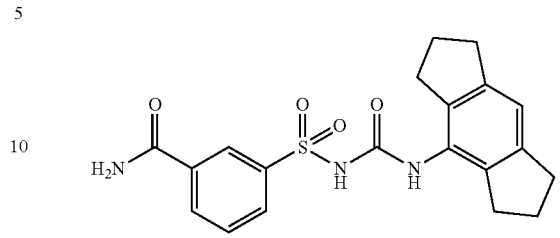

3-(N-((1,2,3,5,6,7-hexahydro-s-indacen-4-yl)carbamoyl)sulfamoyl)benzoic acid (Example 10) (0.06 g, 0.074 mmol) was dissolved in anhydrous N,N-dimethylformamide (4 mL) and the solution cooled to 0° C. Diisopropylethylamine (3.0 eq) and HATU (2.0 eq) were added and the mixture stirred at 0° C. for 15 min. Ammonium chloride (3.0 eq) was added and the mixture stirred at ambient temperature for 5 h. Upon completion the reaction mixture was poured into brine (20 mL) and extracted with ethyl acetate (2×10 mL). The combined organic extracts were washed with brine (10 mL), dried ($Na_2SO_4$) and concentrated in vacuo. The crude residue was purified by reverse phase preparative HPLC to afford the titled compound as a white solid (0.011 g, 37%). $^1$H NMR (400 MHz, DMSO-$d_6$): δ=8.23 (d, J=9.2 Hz, 2H), 8.02 (s, 1H), 7.89 (d, J=7.6 Hz, 1H), 7.84 (d, J=7.6 Hz, 1H), 7.42 (t, J=8.0 Hz, 1H), 7.38 (s, 1H), 7.33 (s, 1H). 6.74 (s, 1H), 2.73 (t, J=6.8 Hz, 4H), 2.62 (t, J=6.8 Hz, 4H), 1.87 (quin, J=7.6 Hz, 4H). LCMS, Purity: 93%, m/z 400.05 (M+H$^+$). HRMS (FAB$^+$) calcd for $C_{20}H_{21}N_3O_4S$ [M+H]$^+$: 400.1253, found: 400.1378.

Example 12: N-(3-(N-((1,2,3,5,6,7-hexahydro-s-indacen-4-yl)carbamoyl)sulfamoyl)-phenyl)pent-4-ynamide

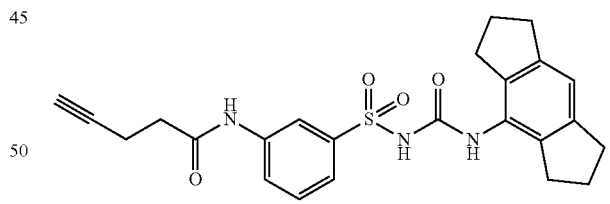

4-Isocyanato-1,2,3,5,6,7-hexahydro-s-indacene (prepared using general method A2) and N-(3-sulfamoylphenyl)pent-4-ynamide (Intermediate 1-12) were used in general method B3 to give the titled compound as a white solid (116 mg, 61%). $^1$H NMR (400 MHz, CD$_3$OD) δ=8.18 (s, 1H), 7.81 (d, J=8.3 Hz, 1H), 7.68 (d, J=8.3 Hz, 1H), 7.43 (dd, J=8.3, 7.8 Hz, 1H), 6.87 (s, 1H), 2.79 (t, J=7.2 Hz, 4H), 2.67-2.60 (m, 4H), 2.60-2.48 (m, 4H), 2.28-2.22 (m, 1H), 2.04-1.89 (m, 4H). $^{13}$C NMR (101 MHz, CD$_3$OD) δ=170.9, 143.3, 143.0, 138.8, 137.7, 128.7, 128.3, 126.4, 122.8, 122.0, 117.9, 117.7, 82.0, 68.9, 35.4, 32.4, 29.9, 25.1, 13.9. HRMS (ESI) calcd. for $C_{24}H_{26}N_3O_4S$ [M+H] 452.1639, found 452.1658.

Example 13: 3-(4-(N-((1,2,3,5,6,7-Hexahydro-s-indacen-4-yl)carbamoyl)sulfamoyl)-phenyl)-N-(prop-2-yn-1-yl)propanamide

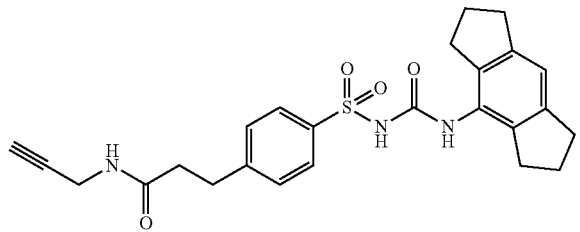 [SMILES: C#CCNC(=O)CCc1ccc(S(=O)(=O)NC(=O)Nc2c3c(cc4c2CCC4)CCC3)cc1]

4-Isocyanato-1,2,3,5,6,7-hexahydro-s-indacene (prepared using general method A2) and N-(prop-2-yn-1-yl)-3-(4-sulfamoylphenyl)propanamide (Intermediate 1-13) were used in general method B3 to give the titled compound as a white solid (120 mg, 68%). $^1$H NMR (400 MHz, CD$_3$OD) δ=7.91 (d, J=7.8 Hz, 2H), 7.39 (d, J=7.8 Hz, 2H), 6.98 (s, 1H), 3.95 (d, J=2.9 Hz, 2H), 3.03 (t, J=7.7 Hz, 2H), 2.85 (t, J=7.4 Hz, 4H), 2.62 (t, J=6.9 Hz, 4H), 2.55-2.46 (m, 2H), 2.25 (t, J=2.6 Hz, 1H), 2.02 (m, 4H). $^{13}$C NMR (101 MHz, CD$_3$OD) δ=172.0, 147.2, 144.1, 143.8, 137.5, 129.0, 128.8, 128.1, 127.4, 126.5, 118.9, 79.2, 71.0, 36.8, 32.8, 32.8, 31.2, 30.7, 28.8, 28.7, 25.4, 25.3. HRMS (ESI) calcd. for C$_{25}$H$_{28}$N$_3$O$_4$S [M+H] 466.1795, found 466.1794.

Example 14: N-(4-(N-(1,2,3,5,6,7-Hexahydro-s-indacen-4-ylcarbamoyl)sulfamoyl)-phenethyl)-2-(methyl(7-nitrobenzo[c][1,2,5]oxadiazol-4-yl)amino)acetamide

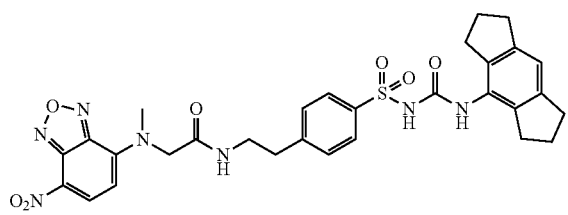 [SMILES: CN(CC(=O)NCCc1ccc(S(=O)(=O)NC(=O)Nc2c3c(cc4c2CCC4)CCC3)cc1)c1ccc([N+](=O)[O-])c2nonc12]

4-Isocyanato-1,2,3,5,6,7-hexahydro-s-indacene (prepared using general method A1) and 2-(methyl(7-nitrobenzo[c][1,2,5]oxadiazol-4-yl)amino)-N-(4-sulfamoylphenethyl)acetamide (Intermediate 1-14) were used in general method B2 to give the titled compound as an orange solid (0.003 g, 1%). $^1$H NMR (400 MHz, DMSO-d$_6$): δ=10.74 (s, 1H), 8.51 (d, J=8.8 Hz, 1H), 8.31 (t, J=7.6 Hz, 1H), 8.09-7.96 (m, 1H), 7.82 (d, J=8.4 Hz, 2H), 7.41 (d, J=7.6 Hz, 2H), 6.89 (s, 1H), 6.42-6.32 (m, 1H), 4.74 (bs, 2H), 3.44-3.30 (m, 5H), 2.80 (t, J=7.6 Hz, 2H), 2.73-2.69 (m, 4H), 2.61-2.50 (m, 4H), 1.92-1.88 (m, 4H). LCMS, Purity: 92.20%, m/z 632.35 (M−H$^+$).

Example 15: 2-(7-(Dimethylamino)-2-oxo-2H-chromen-4-yl)-N-(4-(N-(1,2,3,5,6,7-hexahydro-s-indacen-4-ylcarbamoyl)sulfamoyl)phenethyl)acetamide

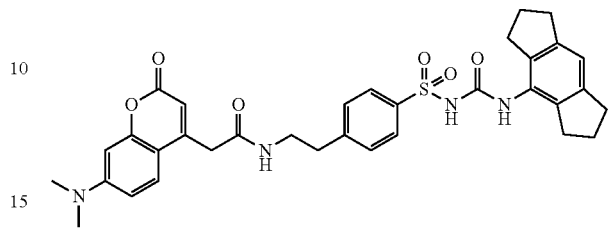

4-Isocyanato-1,2,3,5,6,7-hexahydro-s-indacene (prepared using general method A1) and 2-(7-(dimethylamino)-2-oxo-2H-chromen-4-yl)-N-(4-sulfamoylphenethyl)acetamide (Intermediate 1-15) were used in general method B2 to give the titled compound as a pale-yellow solid (0.008 g, 0.44%). $^1$H NMR (400 MHz, DMSO-d$_6$): δ=9.53 (s, 1H), 8.29 (t, J=4.8 Hz, 1H), 8.22 (s, 1H), 7.68 (d, J=8.0 Hz, 2H), 7.46 (d, J=8.8 Hz, 1H), 8.42 (s, 1H), 7.16 (d, J=8.0 Hz, 2H), 6.74-6.70 (m, 2H), 6.54 (d J=2.4 Hz, 1H), 5.99 (s, 1H), 3.56-3.52 (m, 2H), 3.48 (t, J=6.0 Hz, 2H), 3.31-3.24 (m, 2H), 2.76-2.70 (m, 4H), 3.02 (s, 6H), 2.63 (t, J=7.2 Hz, 4H), 1.88 (quin, J=7.6 Hz, 4H). LCMS, Purity: 92.26%, m/z 629.40 (MH$^+$).

Example 16: Ethyl 5-(N-((3,5,6,7-tetrahydro-2H-indeno[5,6-b]furan-8-yl)carbamoyl)-sulfamoyl)furan-3-carboxylate

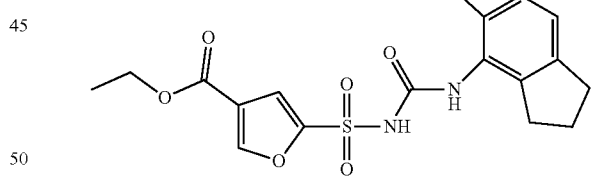

8-Isocyanato-3,5,6,7-tetrahydro-2H-indeno[5,6-b]furan (prepared using general method A1 from Intermediate 1-16) and ethyl 5-sulfamoylfuran-3-carboxylate were used in general method B1 to give ethyl 5-(N-((3,5,6,7-tetrahydro-2H-indeno[5,6-b]furan-8-yl)carbamoyl)sulfamoyl)furan-3-carboxylate as a pale-brown solid (0.25 g, 50%). $^1$H NMR (300 MHz, DMSO-d$_6$) δ 8.32 (s, 1H), 7.17 (s, 1H), 6.77 (d, J=5.2 Hz, 1H), 4.43 (t, J=8.6 Hz, 2H), 4.23 (q, J=7.1 Hz, 2H), 3.07 (t, J=8.6 Hz, 2H), 2.71 (t, J=7.3 Hz, 2H), 2.63 (t, J=7.3 Hz, 2H), 1.89 (p, J=7.4 Hz, 2H), 1.26 (t, J=7.1 Hz, 3H).

Example 17: Ethyl 5-(N-(benzo[1,2-b:4,5-b']difuran-4-ylcarbamoyl)sulfamoyl)furan-3-carboxylate

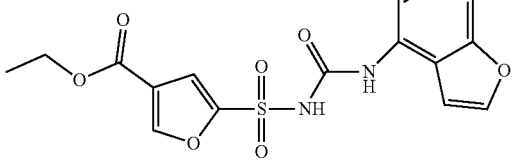

4-isocyanatobenzo[1,2-b:4,5-b']difuran (prepared using general method A1 from Intermediate 1-17) and ethyl 5-sulfamoylfuran-3-carboxylate were used in general method B1 to give ethyl 5-(N-(benzo[1,2-b:4,5-b']difuran-4-ylcarbamoyl)sulfamoyl)furan-3-carboxylate as a white solid (0.05 g, 53%). $^1$H NMR (300 MHz, CD$_3$OD) δ=8.25 (s, 1H), 7.72 (d, J 2.1 Hz, 1H), 7.63 (d, J 2.1 Hz, 1H), 7.46 (s, 1H), 7.27 (s, 1H), 6.93 (s, 1H), 6.89 (d, J 2.1 Hz, 1H), 6.86 (d, J 2.1 Hz, 1H), 4.30 (q, J 6.9 Hz, 2H), 1.4 (t, J 6.9 Hz, 3H).

Example 18: Methyl 2-(N-(1,2,3,5,6,7-hexahydro-s-indacen-4-ylcarbamoyl)sulfamoyl)-isonicotinate

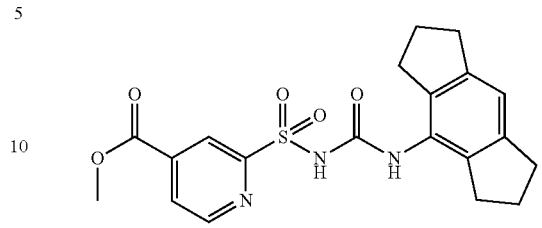

To a solution of 1,2,3,5,6,7-hexahydro-s-indacen-4-amine (0.20 g, 1.15 mmol) in anhydrous THF (5 mL), triethylamine (0.35 g, 3.47 mmol, 3.0 eq) was added followed by triphosgene (0.265 g, 0.86 mmol, 0.5 eq) at 0° C. and the mixture was stirred at ambient temperature for 3 h. The mixture was cooled to 0° C., methyl 2-sulfamoylisonicotinate (0.27 g, 1.27 mmol, 1.1 eq) added and stirring continued at ambient temperature overnight. Upon completion the reaction mixture was poured into brine and extracted with ethyl acetate. The combined organic extracts were washed with brine, dried (Na$_2$SO$_4$) and concentrated in vacuo. The crude product was purified by column chromatography on silica gel using 20-50% gradient of EtOAc-hexanes eluent to give methyl 2-(N-(1,2,3,5,6,7-hexahydro-s-indacen-4-ylcarbamoyl)sulfamoyl)isonicotinate as a light brown solid (0.31 g, 65%).

Example 19: 3-(1-(3-Aminopropyl)-1H-1,2,3-triazol-4-yl)-N-(3-(N-((1,2,3,5,6,7-hexahydro-s-indacen-4-yl)carbamoyl)sulfamoyl)phenyl)propanamide

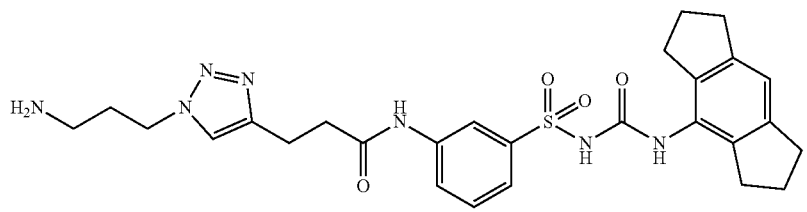 [SMILES: NCCCn1cc(CCC(=O)Nc2cccc(S(=O)(=O)NC(=O)Nc3c4c(cc5c3CCC5)CCC4)c2)nn1]

N-(3-(N-((1,2,3,5,6,7-hexahydro-s-indacen-4-yl)carbamoyl)sulfamoyl)phenyl)pent-4-ynamide (Example 12) and 3-azidopropan-1-amine were used in general method C to give the titled compound as a white solid (6 mg, 43%). $^1$H NMR (600 MHz, CD$_3$OD) δ=7.85 (s, 1H), 7.55 (t, J=3.8 Hz, 2H), 7.50 (d, J=8.0 Hz, 2H), 7.29 (t, J=7.9 Hz, 1H), 6.78 (s, 1H), 4.26 (t, J=6.4 Hz, 2H), 3.00 (t, J=6.6 Hz, 2H), 2.71 (t, J=7.3 Hz, 4H), 2.64-2.50 (m, 8H), 1.94-2.02 (m, 2H), 1.92-1.83 (m, 4H). $^{13}$C NMR (151 MHz, CD$_3$OD) δ=173.0, 147.4, 146.8, 144.7, 144.6, 139.5, 139.2, 131.6, 130.0, 129.8, 124.2, 123.9, 123.2, 119.5, 118.6, 48.3, 37.7, 34.0, 31.6, 26.7, 26.6, 22.9. HRMS (ESI) calcd. for C$_{27}$H$_{34}$N$_7$O$_4$S [M+H] 552.2387, found 552.2368.

Example 20: N-(3-(N-((1,2,3,5,6,7-hexahydro-s-indacen-4-yl)carbamoyl)sulfamoyl)-phenyl)-3-(1-(3-((7-nitrobenzo[c][1,2,5]oxadiazol-4-yl)amino)propyl)-1H-1,2,3-triazol-4-yl)propanamide

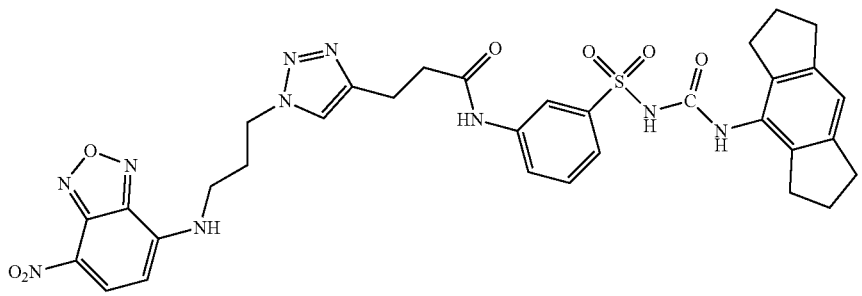 [SMILES: O=C(CCc1cn(CCCNc2ccc([N+](=O)[O-])c3nonc23)nn1)Nc1cccc(S(=O)(=O)NC(=O)Nc2c3c(cc4c2CCC4)CCC3)c1]

N-(2-Azidopropyl)-7-nitrobenzo[c][1,2,5]oxadiazol-4-amine was synthesized by the methods contained in Chun Li, Etienne Henry, Naresh Kumar Mani, Jie Tang, Jean-Claude Brochon, Eric Deprez, and Juan Xie, Eur. J. Org. Chem., 2010, 2395-2405. To a solution of 4-chloro-7-nitrobenzo[c][1,2,5]oxadiazole (300 mg, 1.5 mmol) in THF (10 mL) was added 3-azidopropyl amine (160 mg, 1.65 mmol) and $Cs_2CO_3$ (480 mg, 1.5 mmol). The reaction mixture was stirred at 50° C. for 4 h. The reaction mixture was partitioned between EtOAc (50 mL) concentrated in vacuo. The residue was purified by column chromatography on silica gel using 30% EtOAc-petroleum ether eluent to afford N-(2-Azidopropyl)-7-nitrobenzo[c][1,2,5]oxadiazol-4-amine (240 mg, 76%). $^1$H NMR (400 MHz, CDCl$_3$): δ=8.50 (d, J=8.8 Hz, 1H), 6.57 (s, 1H, NH), 6.23 (d, J=8.8 Hz, 1H), 3.66 (q, J=6.8 Hz, 2H), 3.59 (J=6.0 Hz, 2H), 2.00-2.16 (m, 2H). $^{13}$C NMR (101 MHz, CDCl$_3$) δ 144.2, 144.0, 143.8, 136.7, 123.7, 98.8, 49.1, 41.6, 27.6. HRMS (ESI): calcd. for $C_9H_{10}N_7O_3$ 264.0840; found 264.0711.

N-(3-(N-((1,2,3,5,6,7-Hexahydro-s-indacen-4-yl)carbamoyl)sulfamoyl)phenyl)pent-4-ynamide (Example 12) (10 mg, 0.022 mmol) and N-(2-azidopropyl)-7-nitrobenzo[c][1,2,5]oxadiazol-4-amine (7.0 mg, 0.026 mmol), 10 mol % THPTA, 5 mol % CuSO$_4$, 10 mol % sodium ascorbate in DMSO (500 uL) were stirred at room temperature for 12 h. The reaction mixture was subjected to purification using reverse phase (Reveleris flash column chromatography, 4 g, 18 mL/min., mobile phase; 10 mmol aqu. NH$_4$CO$_3$, MeCN) and freeze dried to give the product as a white solid (7.0 mg, 44%). $^1$H NMR (600 MHz, CD$_3$OD) δ=8.46 (d, J=8.7 Hz, 1H), 8.18 (s, 1H), 7.79 (d, J=8.4 Hz, 1H), 7.67 (d, J=7.9 Hz, 1H), 7.61 (s, 1H), 6.94 (s, 1H), 6.15 (d, J=9.0 Hz, 1H), 4.46 (t, J=6.7 Hz, 2H), 3.09 (t, J=7.0 Hz, 2H), 2.82 (t, J=7.4 Hz, 4H), 2.77 (t, J=7.0 Hz, 2H), 2.70-2.56 (m, 6H), 2.37-2.26 (m, 2H), 1.99 (q, J=7.3 Hz, 4H). $^{13}$C NMR (151 MHz, CD$_3$OD) δ=172.9, 147.9, 145.4, 140.5, 139.0, 138.4, 130.6, 129.1, 128.0, 125.6, 124.2, 123.6, 120.3, 119.6, 112.4, 70.6, 48.9, 37.2, 34.3, 34.2, 31.7, 30.2, 26.8, 22.3; HRMS (ESI) calcd. for $C_{33}H_{34}N_{10}O_7S$ [M−H] 713.2260, found 713.2290.

Example 21: N-(3-(4-(3-((3-(N-((1,2,3,5,6,7-hexahydro-s-indacen-4-yl)carbamoyl)sulfamoyl)phenyl)amino)-3-oxopropyl)-1H-1,2,3-triazol-1-yl)propyl)-5-((3aS,4S,6aR)-2-oxohexahydro-1H-thieno[3,4-d]imidazol-4-yl)pentanamide

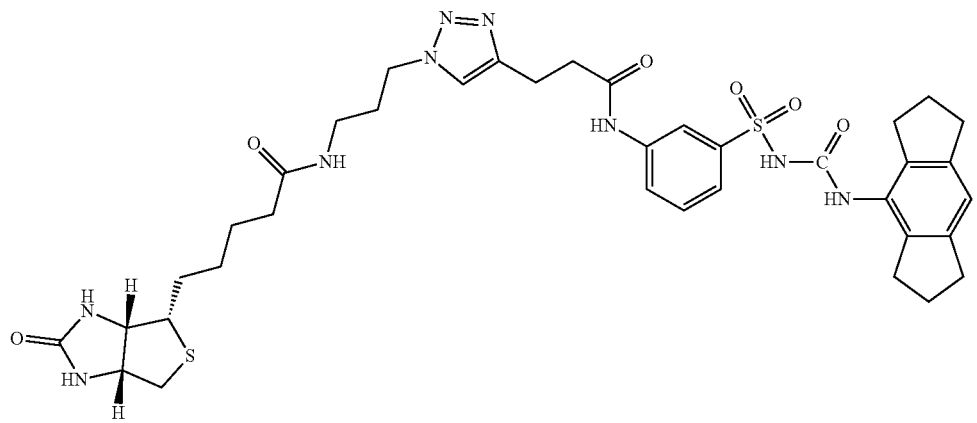 [SMILES: O=C(CCCC[C@@H]1SC[C@@H]2NC(=O)N[C@@H]21)NCCCn1cc(CCC(=O)Nc2cccc(S(=O)(=O)NC(=O)Nc3c4c(cc5c3CCC5)CCC4)c2)nn1]

To a solution of biotin (0.4 g, 1.63 mmol) and 3-azidopropylamine (0.2 g, 1.96 mmol) in dry DMF (10.0 ml) was added HBTU (0.93 g, 2.45 mmol) followed by DIPEA (428 uL, 2.45 mmol). The reaction mixture was stirred at RT for 12 h. The reaction was monitored by LCMS and after the completion of reaction, it was diluted with EtOAc (50 mL) washed with H$_2$O (25 mL), brine (25 mL). The organic layer was separated; dried (MgSO$_4$) and evaporated to give the crude product. The crude product was purified by column Example 22: N-((1-(3-(N-((1,2,3,5,6,7-hexahydro-s-indacen-4-yl)carbamoyl)sulfamoyl)phenyl)-1H-1,2,3-triazol-4-yl)methyl)-5-((3aS,4S,6aR)-2-oxohexahydro-1H-thieno[3,4-d]imidazol-4-yl)pentanamide

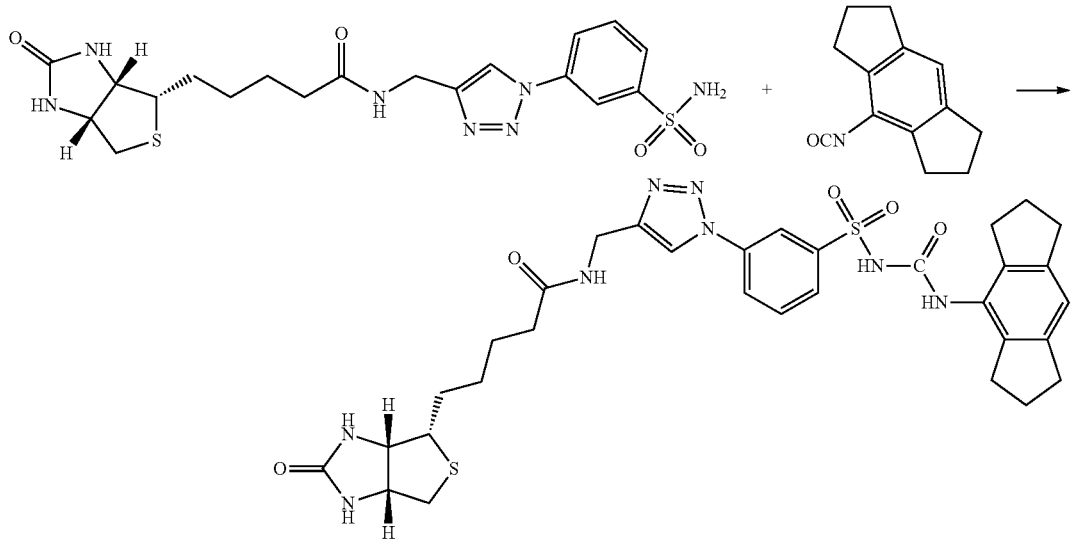

chromatography on silica gel using 50% EtOAc-Hexane eluent to isolate N-(3-azidopropyl)-5-((3aS,4S,6aR)-2-oxohexahydro-1H-thieno[3,4-d]imidazol-4-yl)pentanamide as a white solid (0.13 g, 24%). $^1$H NMR (400 MHz, CD$_3$OD) δ=4.52 (dd, J=7.9, 5.0 Hz, 1H), 4.32 (dd, J=7.9, 4.5 Hz, 1H), 3.36 (t, J=6.7 Hz, 2H), 3.28 (d, J=6.8 Hz, 2H), 3.21-3.14 (m, 1H), 2.93 (dd, J=12.8, 5.0 Hz, 1H), 2.75 (d, J=12.8 Hz, 1H), 2.20 (t, J=7.3 Hz, 2H), 1.78 (q, J=6.8 Hz, 2H), 1.74-1.57 (m, 4H), 1.45 (q, J=7.5 Hz, 2H). $^{13}$C NMR (101 MHz, CD$_3$OD) δ=173.5, 163.4, 61.0, 59.3, 54.7, 48.2, 39.4, 35.8, 34.8, 27.7, 27.5, 27.2, 24.6.

N-(3-(N-((1,2,3,5,6,7-hexahydro-s-indacen-4-yl)carbamoyl)sulfamoyl)phenyl)pent-4-ynamide (Example 12) (1.0 mmol) and N-(3-azidopropyl)-5-((3aS,4S,6aR)-2-oxohexahydro-1H-thieno[3,4-d]imidazol-4-yl)pentanamide (2.0 mmol), 10 mol % THPTA, 5 mol % CuSO$_4$, 10 mol % sodium ascorbate in DMSO were stirred at room temperature for 12 h. The reaction mixture was purified using reverse phase column chromatography to give the titled compound as a white solid (8.0 mg, 31%); $^1$H NMR (600 MHz, CD$_3$OD) δ=8.26 (s, 1H), 7.83-7.68 (m, 3H), 7.50-7.43 (m, 1H), 6.92 (s, 1H), 4.48 (dd, J=8.0, 4.8 Hz, 1H), 4.41-4.22 (m, 3H), 3.18 (dd, J=6.9, 3.5 Hz, 1H), 3.14 (td, J=6.7, 1.7 Hz, 2H), 3.12-3.06 (m, 2H), 2.90 (dd, J=12.8, 4.9 Hz, 1H), 2.81 (t, J=7.7 Hz, 4H), 2.77 (d, J=7.1 Hz, 1H), 2.71 (s, 1H), 2.62 (t, J=7.3 Hz, 4H), 2.19 (td, J=7.4, 1.7 Hz, 2H), 2.05-2.01 (m, 2H), 2.00-1.95 (m, 4H), 1.76-1.57 (m, 4H), 1.43 (q, J=7.6, 7.1 Hz, 2H). $^{13}$C NMR (151 MHz, CD$_3$OD) δ=174.8, 174.8, 171.6, 171.5, 164.5, 146.2, 143.6, 139.1, 137.7, 129.1, 129.1, 128.7, 128.1, 126.5, 123.7, 122.9, 122.4, 122.2, 120.9, 118.4, 118.4, 118.3, 118.2, 117.2, 110.5, 69.0, 61.9, 60.2, 55.6, 39.8, 36.1, 36.0, 35.8, 35.4, 35.4, 32.6, 32.6, 30.0, 29.7, 29.7, 28.6, 28.3, 28.0, 25.3, 25.2, 25.2, 20.9. HRMS (ESI) calcd. for C$_{37}$H$_{48}$N$_9$O$_6$S$_2$[M+H] 778.3163, found 778.3145.

5-((3aS,4S,6aR)-2-oxohexahydro-1H-thieno[3,4-d]imidazol-4-yl)-N-((1-(3-sulfamoylphenyl)-1H-1,2,3-triazol-4-yl)methyl)pentanamide was synthesized using 5-((3aS,4S,6aR)-2-oxohexahydro-1H-thieno[3,4-d]imidazol-4-yl)-N-(prop-2-yn-1-yl)pentanamide (1.0 mmol) and 3-azidobenzenesulfonamide (2.0 mmol), 10 mol % THPTA, 5 mol % CuSO$_4$, 10 mol % NaAsc in DMSO were stirred at room temperature for 12 h. The formation of product was observed in LCMS. After completion of the reaction, the reaction mixture was subjected to HPLC purification (Reveleris flash column chromatography, 4 g, 18 mL/min., mobile phase; 10 mmol aq. NH$_4$CO$_3$, MeCN) to isolate 5-((3aS,4S,6aR)-2-oxohexahydro-1H-thieno[3,4-d]imidazol-4-yl)-N-((1-(3-sulfamoylphenyl)-1H-1,2,3-triazol-4-yl)methyl)pentanamid as a white solid (24 mg, 47%) which was used directly.

To a solution of 5-((3aS,4S,6aR)-2-oxohexahydro-1H-thieno[3,4-d]imidazol-4-yl)-N-((1-(3-sulfamoylphenyl)-1H-1,2,3-triazol-4-yl)methyl)pentanamide (15 mg, 0.031 mmol) in THF (5.0 mL) under a nitrogen atmosphere was added DIPEA (605 μL, 0.037 mmol). This mixture was stirred at room temperature for 15 min. A solution of 4-isocyanato-1,2,3,5,6,7-hexahydro-s-indacene (prepared using general method A2) (705 mg, 0.037 mmol) in THF was added drop-wise. The reaction mixture was stirred at room temperature overnight then the solvent was removed in vacuo to give crude compound which was purified by reversed phase column chromatography using 10 mM aq. (NH$_4$)$_2$CO$_3$ and MeCN mobile phase to isolate the titled compound as a white solid (5.2 mg, 24%). $^1$H NMR (600 MHz, CD$_3$OD) δ=8.53 (d, J=2.4 Hz, 1H), 8.50 (d, J=7.5 Hz, 1H), 8.22-8.11 (m, 2H), 7.86-7.78 (m, 1H), 6.99 (s, 1H), 4.62 (s, 2H), 4.57-4.49 (m, 1H), 4.38-4.31 (m, 1H), 3.27-3.20 (m, 1H), 3.00-2.84 (m, 4H), 2.78-2.70 (m, 4H), 2.36 (t, J=7.2 Hz, 2H), 2.06 (q, J=7.4 Hz, 4H), 1.83-1.73 (m, 3H), 1.71-1.63 (m, 1H), 1.54-1.43 (m, 3H). $^{13}$C NMR (151 MHz, CD$_3$OD) δ=174.6, 164.5, 146.1, 145.4, 143.6, 137.7, 137.2, 130.5, 125.9, 123.4, 121.1, 117.8, 110.6, 61.8, 60.2, 55.5, 47.7, 47.6, 39.8, 3.2, 34.3, 32.6, 30.14, 28.2, 27.9, 25.3, 25.2. HRMS (ESI) calcd. for C$_{32}$H$_{39}$N$_8$O$_5$S$_2$[M+H] 679.2479, found 679.2456.

Example 23: N-(4-(N-((1,2,3,5,6,7-hexahydro-s-indacen-4-yl)carbamoyl)sulfamoyl)-phenethyl)-2-methoxybenzamide

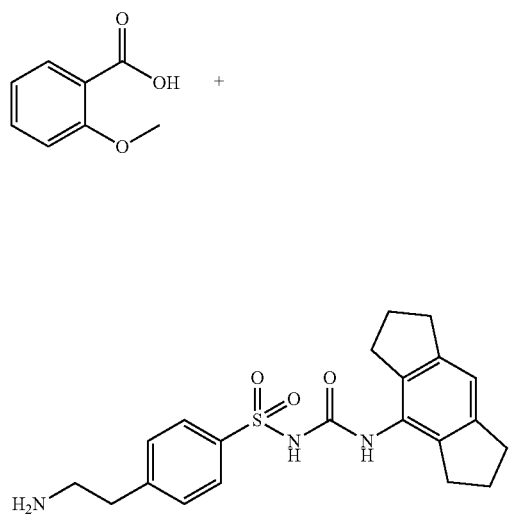

To a solution of 4-(2-aminoethyl)-N-((1,2,3,5,6,7-hexahydro-s-indacen-4-yl)carbamoyl)-benzenesulfonamide (Intermediate 1-23; 50 mg, 125.2 umol) in DMF (1 mL) was added 2-methoxybenzoic acid (21 mg, 137.7 umol), HATU (57 mg, 150.2 umol) and triethylamine (25 mg, 250 umol). The mixture was stirred at 25° C. for 1 hour before the reaction was quenched with water (5 mL) and extracted into dichloromethane (3×15 mL). The combined organic layers were washed with brine (3×15 mL), dried (Na$_2$SO$_4$), filtered and the volatiles removed under reduced pressure. The residue was purified by prep-HPLC to afford the title compound as a white (5.3 mg, 8% yield).

$^1$H NMR (CD$_3$OD) δ 7.97-7.95 (d, 2H), 7.92-7.90 (dd, 1H), 7.48-7.43 (m, 3H), 7.06-7.03 (m, 2H), 6.87 (s, 1H), 3.77 (s, 3H), 3.74-3.70 (t, 2H), 3.01 (t, 2H), 2.82-2.78 (m, 4H), 2.69-2.65 (m, 4H) and 1.00-1.92 (m, 4H).

LCMS: m/z 534.2 (M+H)$^+$

Example 24: N-(4-(N-((1,2,3,5,6,7-hexahydro-s-indacen-4-yl)carbamoyl)sulfamoyl)-phenethyl)-2,3-dihydrobenzofuran-7-carboxamide

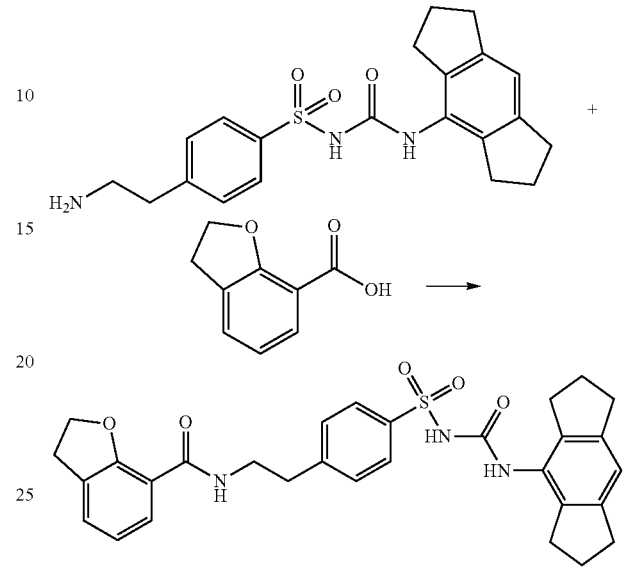

Prepared as described for N-(4-(N-((1,2,3,5,6,7-hexahydro-s-indacen-4-yl)carbamoyl)-sulfamoyl)phenethyl)-2-methoxybenzamide (Example 23) to afford the title compound (17%) as a white solid.

$^1$H NMR (CD$_3$OD) δ 8.00-7.98 (d, 2H), 7.73-7.71 (d, 1H), 7.51-7.49 (d, 2H), 7.36-7.34 (d, 1H), 6.97-6.93 (m, 1H), 6.90 (s, 1H), 4.59-4.55 (t, 2H), 3.74-3.72 (m, 2H), 3.15-3.11 (m, 2H), 3.05-3.03 (m, 2H), 2.80-2.79 (t, 4H), 2.62-2.58 (t, 4H) and 1.98-1.92 (m, 4H).

LCMS: m/z 546.3 (M+H)$^+$

Example 25: N-(4-(N-((1,2,3,5,6,7-hexahydro-s-indacen-4-yl)carbamoyl)-sulfamoyl)phenethyl)-5,6,7,8-tetrahydroimidazo[1,2-a]pyridine-2-carboxamide

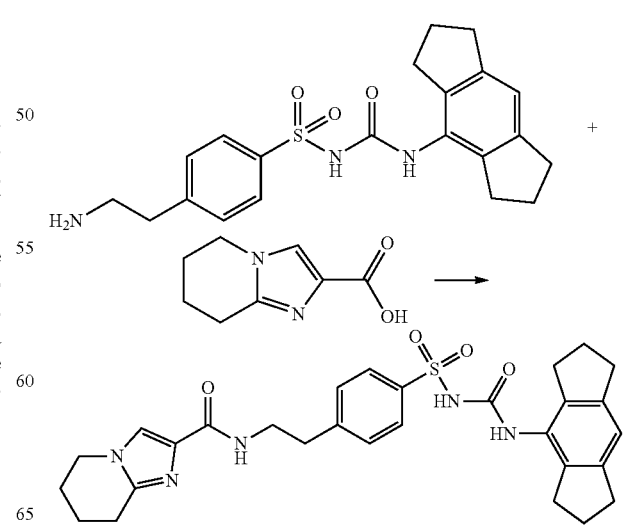

Prepared as described for N-(4-(N-((1,2,3,5,6,7-hexahydro-s-indacen-4-yl)carbamoyl)-sulfamoyl)phenethyl)-2-methoxybenzamide (Example 23) to afford the title compound (17%) as a white solid.

$^1$H NMR (CD$_3$OD) δ7.96-7.94 (d, 2H), 7.49-7.47 (m, 3H), 6.94 (s, 1H), 4.05-4.02 (t, 2H), 3.66-3.62 (t, 2H), 3.03-3.00 (m, 2H), 2.85-2.82 (m, 6H), 2.64-2.61 (m, 4H) and 2.03-1.97 (m, 8H).

LCMS: m/z 548.3 (M+H)$^+$

Example 26: 4-(2-(3-cyclopentylureido)ethyl)-N-((1,2,3,5,6,7-hexahydro-s-indacen-4-yl)carbamoyl)benzenesulfonamide

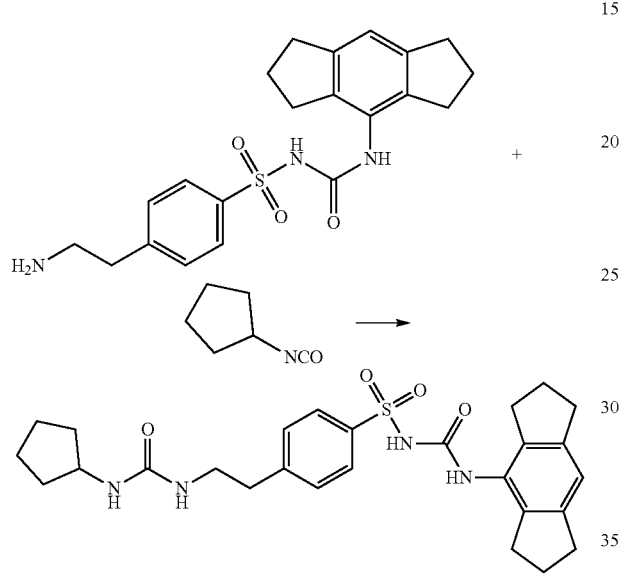

To a solution of 4-(2-aminoethyl)-N-((1,2,3,5,6,7-hexahydro-s-indacen-4-yl)carbamoyl)-benzenesulfonamide (Intermediate 1-23; 60 mg, 150.2 umol) in THF (1.5 mL) was added isocyanatocyclopentane (17 mg, 150.2 umol). The mixture was stirred at 25° C. for 2 hours before the reaction mixture was concentrated in vacuo. The residue was purified by prep-HPLC to afford the title compound as a white solid (5.1 mg, 7% yield).

$^1$H NMR (CD$_3$OD) δ7.93-7.91 (d, 2H), 7.38-7.36 (d, 2H), 6.90 (s, 1H), 3.98-3.95 (m, 1H), 3.41-3.38 (m, 2H), 2.92-2.78 (m, 6H), 2.67 (t, 4H), 2.04-1.96 (m, 4H), 1.93-1.84 (m, 2H), 1.76-1.52 (m, 4H) and 1.42-1.29 (m, 2H).

LCMS: m/z 511.2 (M+H)$^+$

Example 27: 4-(2-(3-Benzylureido)ethyl)-N-((1,2,3,5,6,7-hexahydro-s-indacen-4-yl)carbamoyl)benzenesulfonamide

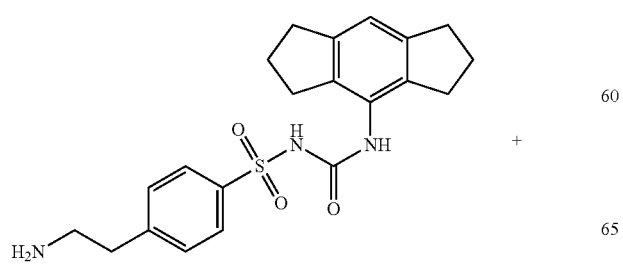

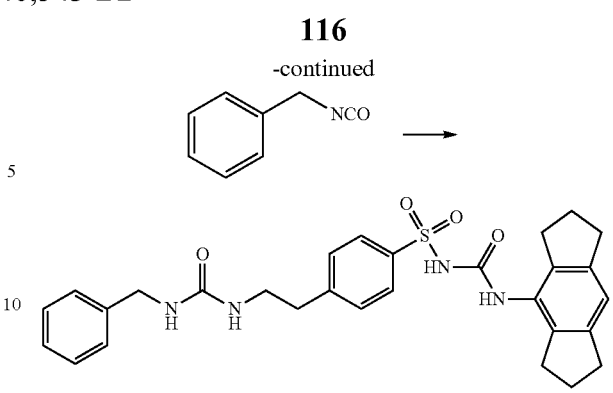

Prepared as described for 4-(2-(3-cyclopentylureido)ethyl)-N-((1,2,3,5,6,7-hexahydro-s-indacen-4-yl)carbamoyl)benzenesulfonamide (Example 26) to afford the title compound as a white solid (15%).

$^1$H NMR (CD$_3$OD) δ7.93-7.91 (d, 2H), 7.38-7.23 (m, 7H), 6.90 (s, 1H), 4.30 (s, 2H), 3.44-3.42 (m, 2H), 2.89-2.80 (m, 6H), 2.68-2.66 (m, 4H) and 2.03-1.97 (m, 4H).

LCMS: m/z 533.3 (M+H)$^+$

Example 28: N-((1,2,3,5,6,7-Hexahydro-s-indacen-4-yl)carbamoyl)-4-(2-(3-phenethylureido)ethyl)benzenesulfonamide

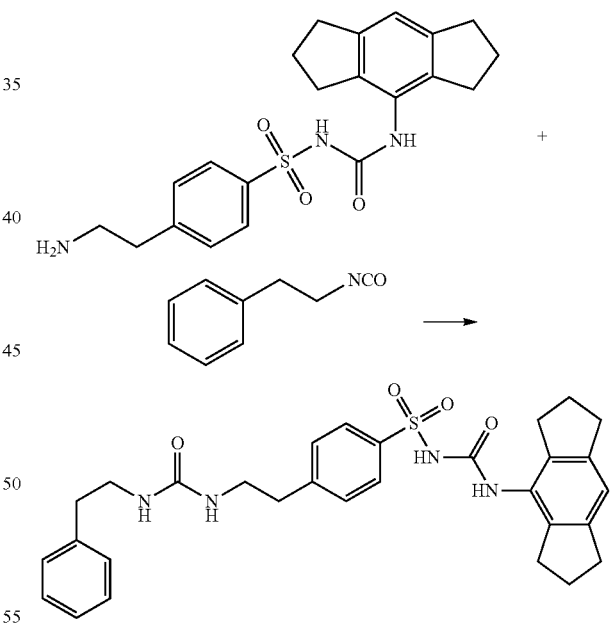

Prepared as described for 4-(2-(3-cyclopentylureido)ethyl)-N-((1,2,3,5,6,7-hexahydro-s-indacen-4-yl)carbamoyl)benzenesulfonamide (Example 26) to afford the title compound as a white solid (8%).

$^1$H NMR (DMSO-d$_6$) δ 7.82 (s, 1H), 7.78-7.76 (d, 2H), 7.31-7.27 (m, 4H), 7.20-7.17 (m, 3H), 6.84 (s, 1H), 5.92-5.88 (m, 2H), 3.25-3.20 (m, 4H), 2.76-2.72 (m, 6H), 2.68-2.66 (m, 2H), 2.60-2.56 (m, 4H), and 1.92-1.89 (m, 4H).

LCMS: m/z 547.2 (M+H)$^+$

Example 29: 2-Ethyl-N-(4-(N-((1,2,3,5,6,7-hexa-hydro-s-indacen-4-yl)carbamoyl)-sulfamoyl)phenethyl)pyrimidine-5-carboxamide

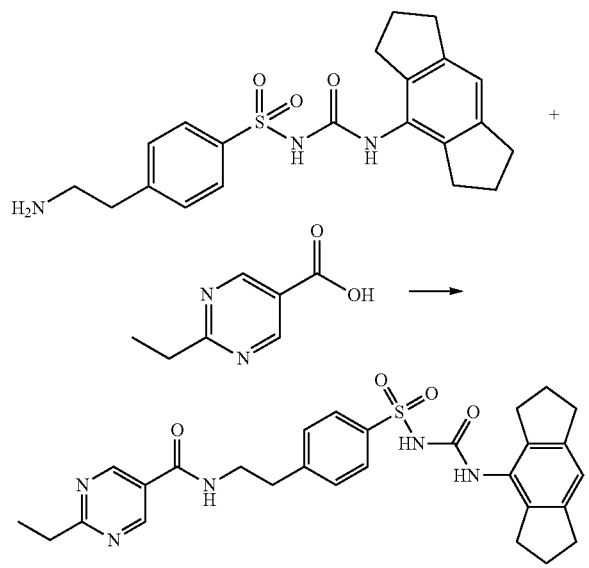

Prepared as described for N-(4-(N-((1,2,3,5,6,7-hexahydro-s-indacen-4-yl)carbamoyl)-sulfamoyl)phenethyl)-2-methoxybenzamide (Example 23) to afford the title compound as a white solid (8%).
$^1$H NMR (DMSO-d$_6$) δ 10.75 (s, 1H), 9.03 (s, 2H), 8.90-8.87 (br t, 1H), 8.03 (s, 1H), 7.86-7.84 (d, 2H), 7.48-7.46 (d, 2H), 6.90 (s, 1H), 3.55-3.53 (m, 2H), 3.01-2.88, (m, 4H), 2.76-2.74 (m, 4H), 2.54-2.51 (m, 4H), 1.92-1.88 (m, 4H) and 1.31-1.27 (t, 3H).
LCMS: m/z 534.1 (M+H)$^+$ Example 30: N-(4-(N-((1,2,3,5,6,7-Hexahydro-s-indacen-4-yl)carbamoyl)-sulfamoyl)-phenethyl)-4-methoxybenzamide

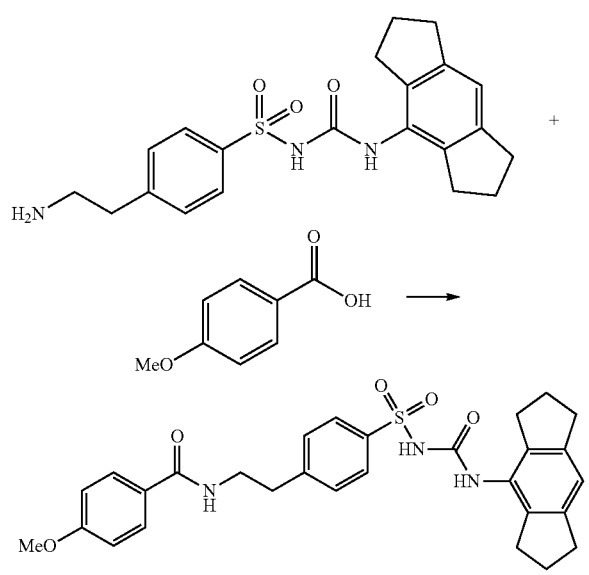

Prepared as described for N-(4-(N-((1,2,3,5,6,7-hexahydro-s-indacen-4-yl)carbamoyl)-sulfamoyl)phenethyl)-2-methoxybenzamide (Example 23) to afford the title compound as a white solid (15%).
$^1$H NMR (DMSO-d$_6$) δ 10.80 (br, s, 1H), 8.46-7.43 (m, 1H), 8.01-8.00 (m, 1H), 7.85-7.78 (m, 4H), 7.46-7.44 (m, 2H), 7.01-6.99 (d, 2H), 6.90 (s, 1H), 3.79 (s, 3H), 3.51-3.47, (m, 2H), 2.92 (br t, 2H), 2.77-2.73 (m, 4H), 2.53-2.51 (m, 4H) and 1.94-1.89 (m, 4H).
LCMS: m/z 534.2 (M+H)$^+$ Example 31: N-((1,2,3,5,6,7-hexahydro-s-indacen-4-yl)carbamoyl)-4-(2-(3-(4-methoxyphenyl)ureido)ethyl)benzenesulfonamide

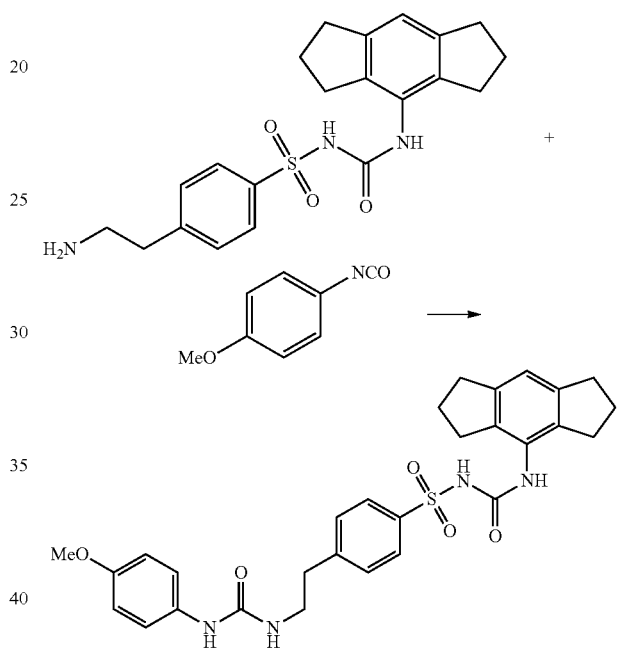

Prepared as described for 4-(2-(3-cyclopentylureido)ethyl)-N-((1,2,3,5,6,7-hexahydro-s-indacen-4-yl)carbamoyl)benzenesulfonamide (Example 26) to afford the title compound as a white solid (8%).
$^1$H NMR (DMSO-d$_6$) δ 8.27 (s, 1H), 7.94 (s, 1H), 7.84-7.82 (d, 2H), 7.42-7.40 (d, 2H), 7.28-7.26 (d, 2H), 6.88 (s, 1H), 6.81-6.79 (d, 2H), 6.05-6.02 (t, 1H), 3.69 (s, 3H), 3.30-3.32 (m, 2H), 2.83-2.80 (t, 2H), 2.78-2.74 (t, 4H), 2.58-2.55 (m, 4H) and 1.98-1.87 (m, 4H).
LCMS: m/z 549.2 (M+H)$^+$

EXAMPLES—BIOLOGICAL STUDIES

NLRP3 Inhibition

The NLRP3-inhibitory effect of a number of the above compounds was tested by measuring the IL-1β secretion from murine bone marrow derived macrophages (BMDM) primed with lipopolysaccharide (LPS), treated with test compound (to a maximum concentration of 200 μM) and finally stimulated with the NLRP3 stimulus ATP. The half-maximal inhibitory concentration (IC$_{50}$) was determined for each compound and compared to a number of comparative examples (CE 1-10) including commercially available oral sulphonylureas (CE1-6) and the known NLRP3 inhibitor MCC 950 (CE7). The experimental protocol was as follows. The results are shown in Table 1 below.

MOUSE PRIMARY MACROPHAGE CELL CULTURE: Macrophages from C57BL/6 mice were differentiated from bone marrow as previously described (Schroder et al. Proceedings of the National Academy of Sciences, 2012, 109, E944-E953). The University of Queensland Animal Ethics Committee approved all experimental protocols involving mice. Murine bone marrow-derived macrophages (BMDM) were cultured in RPMI 1640 medium (Life Technologies) supplemented with 10% heat inactivated fetal calf serum, 2 mM GlutaMAX (Life Technologies) and 50 U/mL penicillin-streptomycin (Life Technologies) and 100 ng/mL recombinant human M-CSF (endotoxin free, expressed and purified by the University of Queensland Protein Expression Facility).

NLRP3 INFLAMMASOME ASSAY: BMDM were seeded at $1 \times 10^6$ cells/mL in 96 well plates. The following day the overnight medium was replaced with Opti-MEM® reduced serum medium (Life Technologies) and cells were stimulated with 100 ng/mL ultrapure *E. coli* K12 LPS (Invivogen) for 3 h. Compounds were prepared from a 10 mM stock by serial dilution in 80% DMSO/20% 10 mM ammonium bicarbonate. Compounds (0.001-200 µM) or vehicle control were added to the LPS primed cells for 30 mins before stimulation with 2.5 mM adenosine 5'-triphosphate disodium salt hydrate (ATP) (Sigma Aldrich) for 1 h. IL-1β levels in cell-free supernatants were analysed by ELISA (ReadySetGo!® eBioscience).

NLRP3 DATA ANALYSIS: $IC_{50}$ values were determined from ELISA data by performing non-linear regression analysis of inhibitor vs. normalized response (variable slope) using Prism Software (GraphPad).

TABLE 1

| Example | Structure | $IC_{50}$ |
|---|---|---|
| 1 | 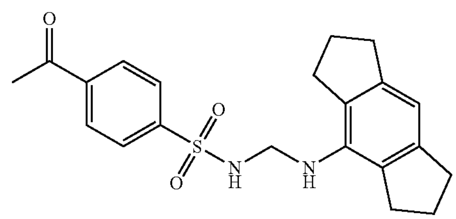 [SMILES: CC(=O)c1ccc(S(=O)(=O)NCNc2c3c(cc4c2CCC4)CCC3)cc1] | +++ |
| 2 | 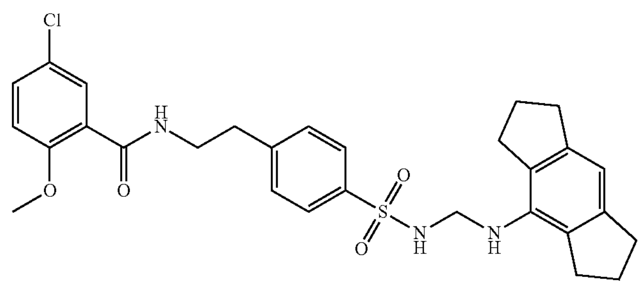 [SMILES: COc1ccc(Cl)cc1C(=O)NCCc1ccc(S(=O)(=O)NCNc2c3c(cc4c2CCC4)CCC3)cc1] | +++ |
| 3 | 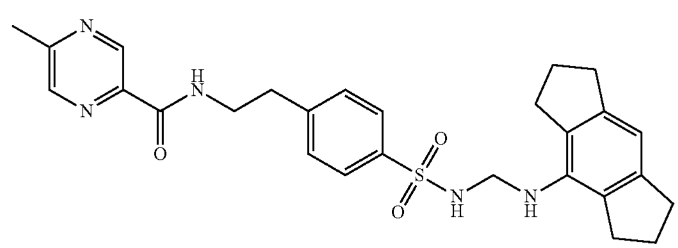 [SMILES: Cc1cnc(C(=O)NCCc2ccc(S(=O)(=O)NCNc3c4c(cc5c3CCC5)CCC4)cc2)cn1] | +++ |
| 4 | 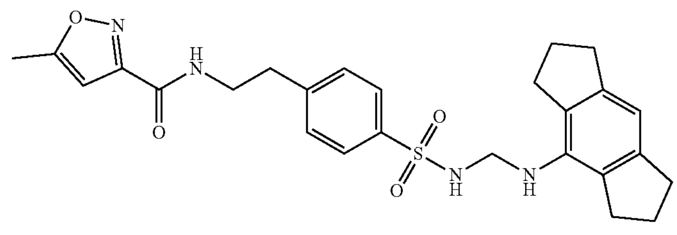 [SMILES: Cc1cc(C(=O)NCCc2ccc(S(=O)(=O)NCNc3c4c(cc5c3CCC5)CCC4)cc2)no1] | +++ |

TABLE 1-continued

| Example | Structure | IC$_{50}$ |
|---|---|---|
| 5 | 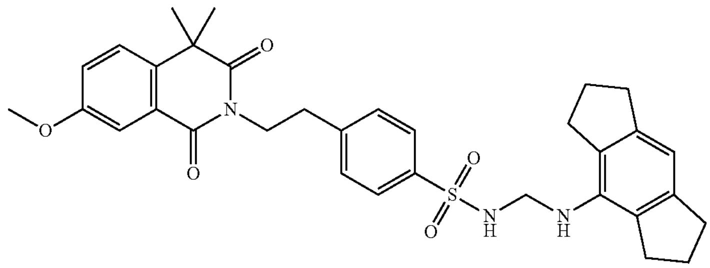 [SMILES: COc1ccc2c(c1)C(=O)N(CCc1ccc(S(=O)(=O)NCNc3c4c(cc5c3CCC5)CCC4)cc1)C(=O)C2(C)C] | +++ |
| 6 | 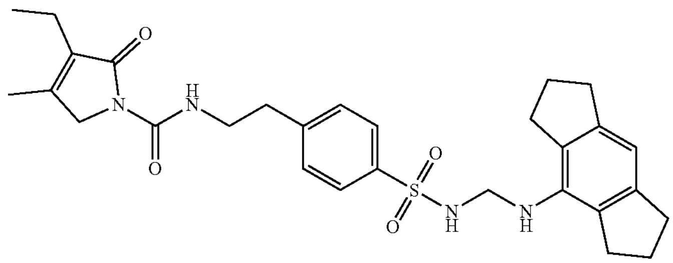 [SMILES: CCC1=C(C)CN(C(=O)NCCc2ccc(S(=O)(=O)NCNc3c4c(cc5c3CCC5)CCC4)cc2)C1=O] | +++ |
| CE$_1$ (Acetohexamide) | 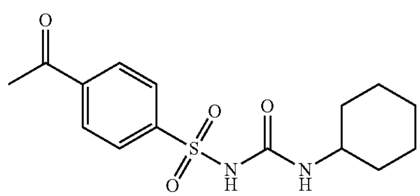 [SMILES: CC(=O)c1ccc(S(=O)(=O)NC(=O)NC2CCCCC2)cc1] | xx |
| CE$_2$ (Glyburide) | 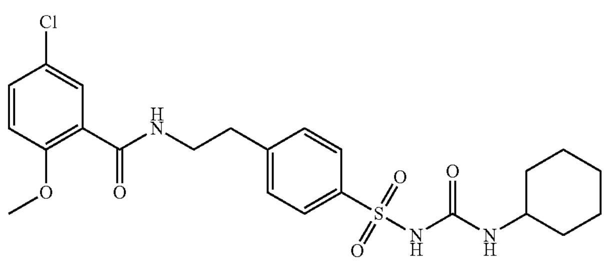 [SMILES: COc1ccc(Cl)cc1C(=O)NCCc1ccc(S(=O)(=O)NC(=O)NC2CCCCC2)cc1] | + |
| CE$_3$ (Glipizide) | 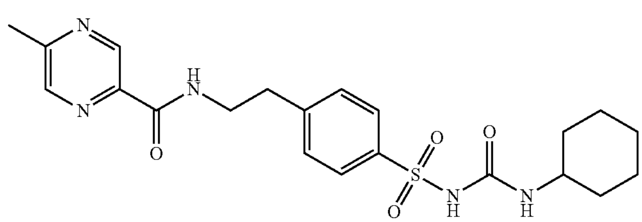 [SMILES: Cc1cnc(C(=O)NCCc2ccc(S(=O)(=O)NC(=O)NC3CCCCC3)cc2)cn1] | xx |
| CE$_4$ (Glisoxepide) | 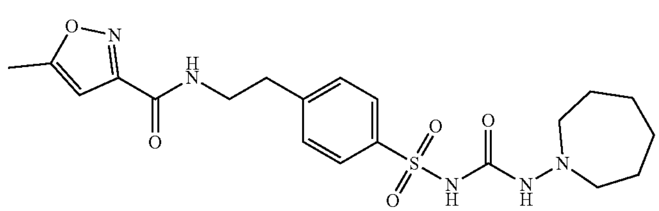 [SMILES: Cc1cc(C(=O)NCCc2ccc(S(=O)(=O)NC(=O)NN3CCCCCC3)cc2)no1] | x |

TABLE 1-continued

| Example | Structure | IC$_{50}$ |
|---|---|---|
| CE$_5$ (Gliquidone) | 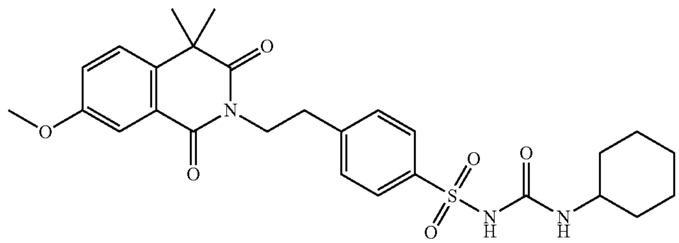 [SMILES: COc1ccc2c(c1)C(=O)N(CCc1ccc(S(=O)(=O)NC(=O)NC3CCCCC3)cc1)C(=O)C2(C)C] | x |
| CE6 (Glimepiride) | 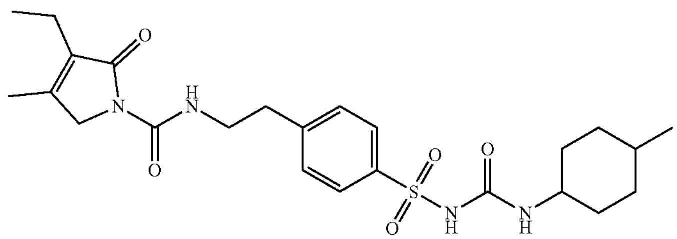 | x |
| CE$_7$ (MCC $_{950}$) | 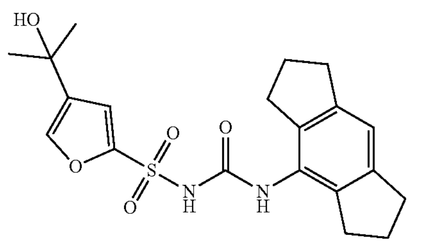 [SMILES: CC(C)(O)c1coc(S(=O)(=O)NC(=O)Nc2c3c(cc4c2CCC4)CCC3)c1] | +++ |
| CE8 | 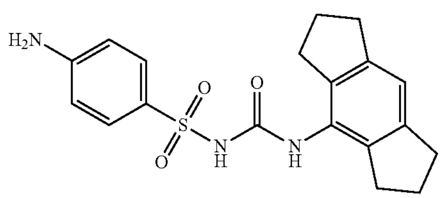 | +++ |
| CE$_9$ | 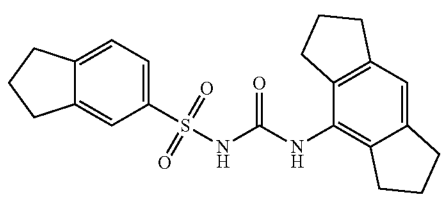 [SMILES: O=C(Nc1c2c(cc3c1CCC3)CCC2)NS(=O)(=O)c1ccc2c(c1)CCC2] | +++ |
| CE$_{10}$ | 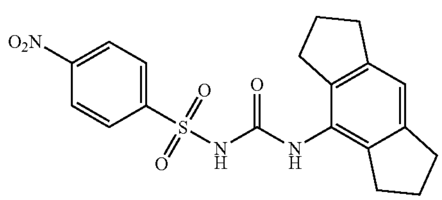 [SMILES: O=C(Nc1c2c(cc3c1CCC3)CCC2)NS(=O)(=O)c1ccc([N+](=O)[O-])cc1] | +++ |

NLRP$_3$ inhibitory activity (<1 μM = '+++', <10 μM = '++', <50 μM = '+', >50 μM = 'x', >200 μM = 'xx').

As is evident from the above, surprisingly in spite of the structural differences the compounds of the invention show comparable NLRP3 inhibitory activity to the known NLRP3 inhibitor MCC 950, and show vastly superior inhibitory activity to the commercially available sulphonyl ureas of comparative examples CE 1-6. The compounds of the invention will therefore find application in the treatment of disorders associated with the over-activity of NLRP3.

To further confirm the NLRP3 inhibitory activity of compounds of the invention, additional assays were performed by measuring the IL-1β secretion, using either murine bone marrow derived macrophages (BMDM) or human monocyte derived macrophages (HMDM), in accordance with the following protocols. The results are shown in Table 2 below. As can be seen, the compounds of the invention show a high level of efficacy.

HMDM CELL CULTURE: To generate HMDM, human monocytes are isolated from buffy coat blood using Ficoll-Plaque Plus (GE Healthcare) and density centrifugation. CD14+ cell selection is performed using MACS magnetic beads (Miltenyl Biotec). Isolated CD14+ monocytes are differentiated in culture for 7 days with 10 ng/ml human CSF-1 (Miltenyl Biotec) in Iscove's modified Dulbecco's medium (IMDM) containing L-glutamine supplemented with 10% FBS and 1% penicillin/streptomycin (Life Technologies) as described by Croker et al., Immunol Cell Biol 2013, vol. 91, p. 625.

BMDM CELL CULTURE: Mouse bone marrow-derived macrophages (BMDM) were derived from bone marrow progenitors isolated from the femurs and tibias of C57BL/6 mice. Bones were flushed with medium, and bone marrow cells were cultured for 7 days in RPMI 1640 medium supplemented with 10% heat inactivated FCS, 2 mM GlutaMAX (Life Technologies), 50 U/ml penicillin-streptomycin (Life Technologies) and 150 ng/ml recombinant human M-CSF (endotoxin-free, expressed and purified by The University of Queensland Protein Expression Facility).

HMDM NLRP3 INFLAMMASOME ASSAY: HMDM are seeded at $1\times10^5$/ml. The following day the overnight medium is replaced and cells are stimulated with *Escherichia coli* serotype 0111:B4 (Sigma Aldrich) for 3 h. Medium is removed and replaced with serum free medium (SFM) containing test compound 30 min prior to NLRP3 stimulation. Cells are then stimulated with: adenosine 5'-triphosphate disodium salt hydrate (5 mM 1 h), nigericin (10 µM 1 h), LeuLeu-OMe (1 mM 2 h) or MSU (200 µg/ml 15 h). ATP can be sourced from Sigma Aldrich, nigericin and MSU from Invivogen and LeuLeu-Ome from Chem-Impex International.

BMDM NLRP3 INFLAMMASOME ASSAY: BMDM are seeded at $1\times10^5$/ml. The following day the overnight medium is replaced and cells are stimulated with Ultrapure lipopolysaccharide from *Escherichia coli* K12 strain (InvivoGen) for 3 h. Medium is removed and replaced with serum free medium (SFM) containing test compound 30 min prior to NLRP3 stimulation. Cells are then stimulated with: adenosine 5'-triphosphate disodium salt hydrate (1.25-5 mM 1 h), nigericin (5 µM 1 h), LeuLeu-OMe (1 mM 2 h) or MSU (200 µg/ml 15 h). ATP can be sourced from Sigma Aldrich, nigericin and MSU from Invivogen and LeuLeu-Ome from Chem-Impex International.

MEASUREMENT OF IL-1β SECRETION: For ELISA assays cells are seeded in 96 well plates. Supernatants are removed and analysed using ELISA kits according to the manufacturer's instructions (DuoSet® R&D Systems, ReadySetGo!® eBioscience, BD OptEIA™, or Perkin Elmer AlphaLISA®).

TABLE 2

| Example | Structure | Avg. IL-1β $IC_{50}$ BMDM | Avg. IL-1β $IC_{50}$ HMDM |
|---|---|---|---|
| 7 | 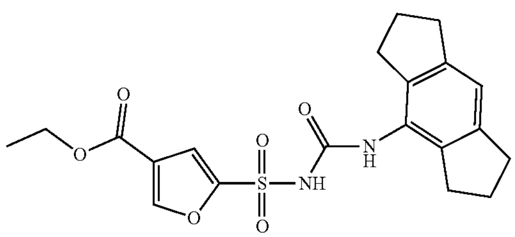 [SMILES: CCOC(=O)c1coc(S(=O)(=O)NC(=O)Nc2c3c(cc4c2CCC4)CCC3)c1] | +++ | ND |
| 8 | 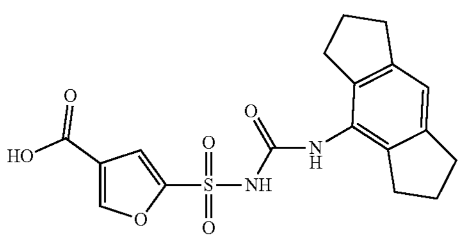 [SMILES: O=C(Nc1c2c(cc3c1CCC3)CCC2)NS(=O)(=O)c1cc(C(=O)O)co1] | ++ | ND |
| 10 | 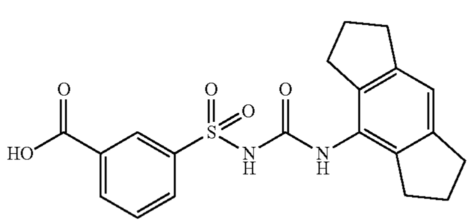 [SMILES: O=C(Nc1c2c(cc3c1CCC3)CCC2)NS(=O)(=O)c1cccc(C(=O)O)c1] | ND | +++ |

TABLE 2-continued

| Example | Structure | Avg. IL-1β IC$_{50}$ BMDM | Avg. IL-1β IC$_{50}$ HMDM |
|---------|-----------|---------------------------|---------------------------|
| 11 | 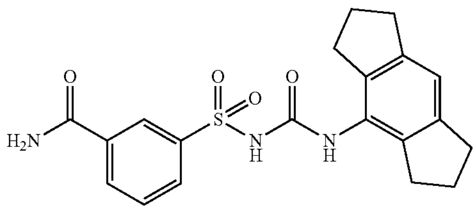 [SMILES: NC(=O)c1cccc(S(=O)(=O)NC(=O)Nc2c3c(cc4c2CCC4)CCC3)c1] | ND | +++ |
| 12 | 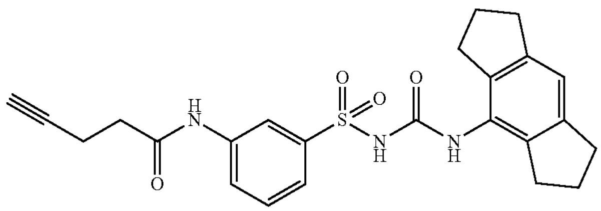 [SMILES: C#CCCC(=O)Nc1cccc(S(=O)(=O)NC(=O)Nc2c3c(cc4c2CCC4)CCC3)c1] | ND | +++ |
| 13 | 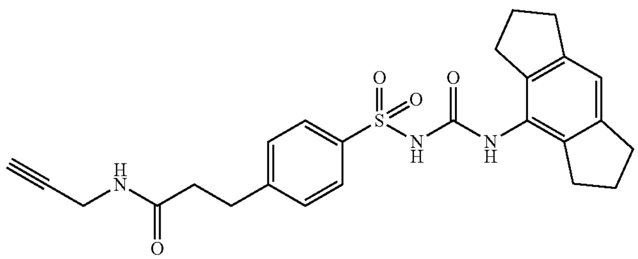 [SMILES: C#CCNC(=O)CCc1ccc(S(=O)(=O)NC(=O)Nc2c3c(cc4c2CCC4)CCC3)cc1] | ND | +++ |
| 14 | 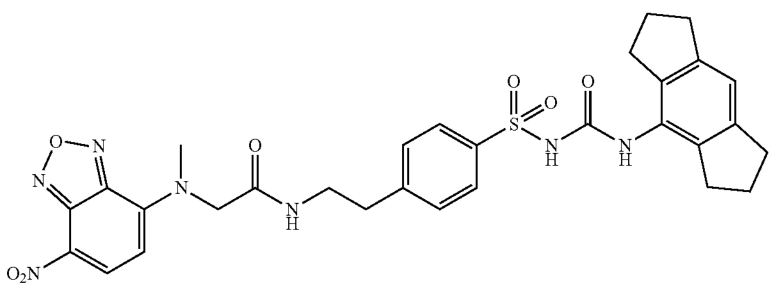 [SMILES: CN(CC(=O)NCCc1ccc(S(=O)(=O)NC(=O)Nc2c3c(cc4c2CCC4)CCC3)cc1)c1ccc([N+](=O)[O-])c2nonc12] | ND | ++ |
| 15 | 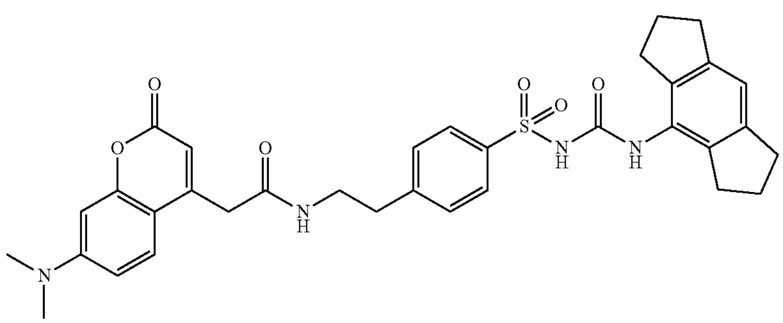 [SMILES: CN(C)c1ccc2c(CC(=O)NCCc3ccc(S(=O)(=O)NC(=O)Nc4c5c(cc6c4CCC6)CCC5)cc3)cc(=O)oc2c1] | ND | +++ |
| 19 | 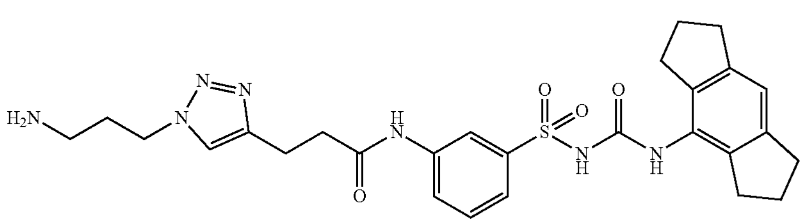 [SMILES: NCCCn1cc(CCC(=O)Nc2cccc(S(=O)(=O)NC(=O)Nc3c4c(cc5c3CCC5)CCC4)c2)nn1] | ND | +++ |

TABLE 2-continued

| Example | Structure | Avg. IL-1β IC$_{50}$ BMDM | Avg. IL-1β IC$_{50}$ HMDM |
|---------|-----------|---------------------------|---------------------------|
| 20 | [structure] | ND | ++ |
| 21 | [structure] | ++ | ++ |
| 22 | [structure] | + | ++ |

NLRP$_3$ inhibitory activity (<1 μM = '+++', <10 μM = '++', <50 μM = '+', >50 μM = 'x', >200 μM = 'xx', not determined = 'ND').

Insulin Secretion

To confirm the insulinotropic properties of the compounds of the invention, their ability to stimulate insulin secretion from MIN6 cells at a single concentration (10 μM) was tested using the following protocol. The tests were conducted by the Garvan Institute of Medical Research, Sydney, Australia.

MIN6 INSULIN ASSAY PROTOCOL: MIN6 cells (passage 29-37) were incubated for 1 h in Krebs-Ringer buffer (KRB) containing 2.8 mM glucose. The cells were then stimulated for 1 h in either 2.8 mM glucose KRB, 20 mM glucose KRB, or 2.8 mM glucose KRB plus test compound. Supernatants were collected and then assayed using rat insulin radioimmunoassay kit (RI-13K, Merck Millipore).

The ability of the compounds of the invention to stimulate insulin secretion was compared to the commercially available insulin secretion stimulator glyburide (CE2) and to a number of NLRP3 inhibitors (CE7-10), including the inhibitor MCC-950 (CE7). The results are shown in FIG. 1.

As is evident, the compounds of the invention remarkably show comparable or even superior efficacy to glyburide (CE2), in spite of the significant structural modification to the urea substituents. Glyburide is only weakly active as an NLRP3 inhibitor however. In contrast, as discussed above, the compounds of the invention are potent NLRP3 inhibitors.

FIG. 1 further demonstrates that not all NLRP3 inhibitors possess the ability to induce insulin secretion. For example, the known NLRP3 inhibitor MCC-950 (CE7) merely results in basal levels of insulin secretion, while the same can be said for the comparative NLRP3 inhibitors CE8-10. Without wishing to be bound by theory, it is believed that the presence of a carbonyl-containing group attached to the cyclic sulphonyl substituent imparts on the compounds of the invention their ability to induce insulin secretion.

It is apparent therefore that a new class of compounds has been discovered, said compounds uniquely possessing dual activity, having the ability to both inhibit NLRP3 and stimulate insulin secretion. Such compounds offer distinct pharmacokinetic, regulatory and clinical advantages in the treatment of disorders responsive to both the inhibition of NLRP3 and the stimulation of insulin secretion, as well as in the treatment of patients with appropriate comorbid conditions.

It will be understood that the present invention has been described above by way of example only. The examples are not intended to limit the scope of the invention. Various modifications and embodiments can be made without departing from the scope and spirit of the invention, which is defined by the following claims only.

The invention claimed is:

1. A compound of formula (I):

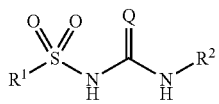

Formula (I)

or a pharmaceutically acceptable salt or solvate thereof, wherein:
Q is O or S;
$R^1$ is a 6-membered cyclic group substituted with at least one group X, wherein $R^1$ may optionally be further substituted;
X is any group comprising a carbonyl group and containing from 1 to 20 carbon atoms; and
$R^2$ is a fused aryl or fused heteroaryl group, wherein a cycloalkyl, cycloalkenyl, non-aromatic heterocyclic, aryl or heteroaryl ring is fused to the aryl or heteroaryl group across the α,β positions, wherein the aryl or heteroaryl group is further substituted at the at α'-position, and wherein $R^2$ may optionally be further substituted.

2. The compound or pharmaceutically acceptable salt or solvate of claim 1, wherein $R^2$ is a fused aryl or a fused heteroaryl group, wherein a first cycloalkyl, cycloalkenyl, non-aromatic heterocyclic, aryl or heteroaryl ring is fused to the aryl or heteroaryl group across the α,β positions and a second cycloalkyl, cycloalkenyl, non-aromatic heterocyclic, aryl or heteroaryl ring is fused to the aryl or heteroaryl group across the α',β' positions, wherein $R^2$ may optionally be further substituted.

3. The compound or pharmaceutically acceptable salt or solvate of claim 1, wherein:
(i) $R^1$ is a 6-membered cyclic group substituted at the 4-position with at least one group X, wherein X is attached to the 6-membered cyclic group only via the 4-position, and wherein the 6-membered cyclic group may optionally be further substituted; or (ii) $R^1$ is a phenyl group or a 6-membered heteroaryl group, wherein the phenyl group or the 6-membered heteroaryl group is substituted at the 4-position with a group X, wherein X is monovalent, and wherein the phenyl group or the 6-membered heteroaryl group may optionally be further substituted.

4. The compound or pharmaceutically acceptable salt or solvate of claim 1, wherein: $R^1$ is a 6-membered heterocyclic group substituted with at least one group X, wherein $R^1$ may optionally be further substituted, and wherein optionally the 6-membered heterocyclic group contains at least one nitrogen atom in the heterocyclic ring.

5. The compound or pharmaceutically acceptable salt or solvate of claim 1, wherein X— is:

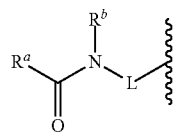

wherein:
L is a bond or an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted;
$R^a$ and $R^b$ together with the atoms to which they are attached may form a cyclic group, or $R^a$ and $R^b$ are each independently selected from hydrogen or an alkyl, alkenyl, alkynyl, Z—, Z-alkylene-, Z-alkenylene- or Z-alkynylene-group, wherein one or more carbon atoms in the backbone of the alkyl, alkenyl, alkynyl, alkylene, alkenylene or alkynylene group may optionally be replaced by one or more heteroatoms N, O or S, wherein each Z— is a cyclic group; and
wherein any $R^a$ and $R^b$ may optionally be substituted.

6. The compound or pharmaceutically acceptable salt or solvate of claim 5, wherein L is an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted.

7. The compound or pharmaceutically acceptable salt or solvate of claim 1, which is (a) a compound selected from the group consisting of:

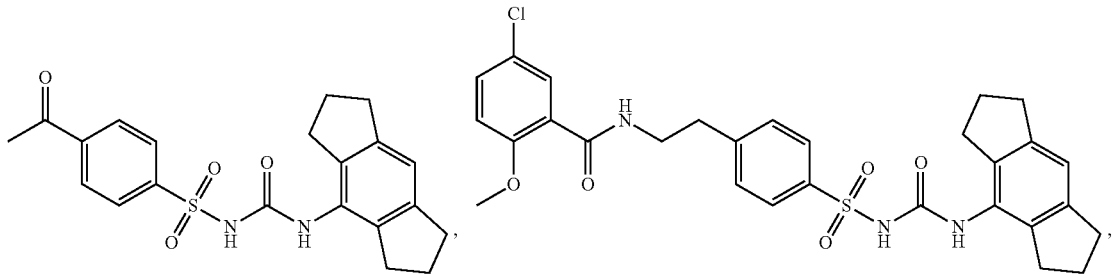

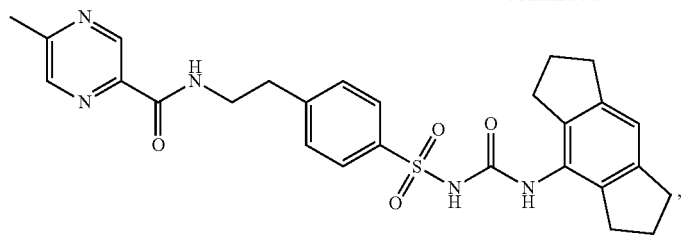
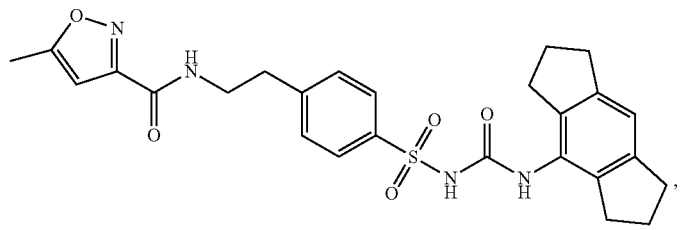
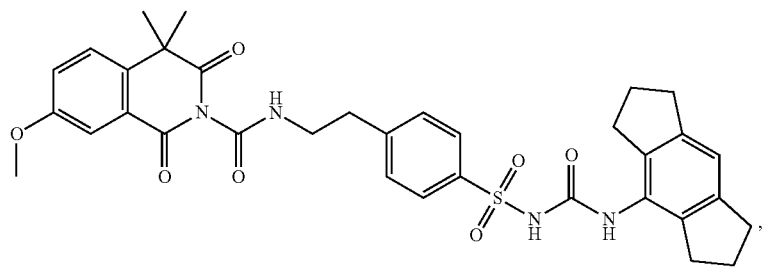
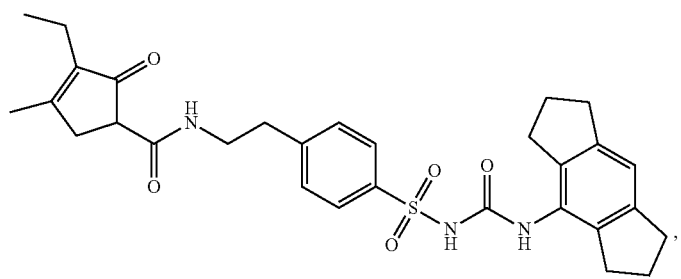
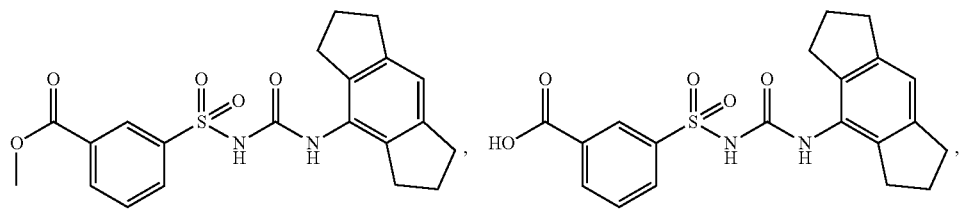
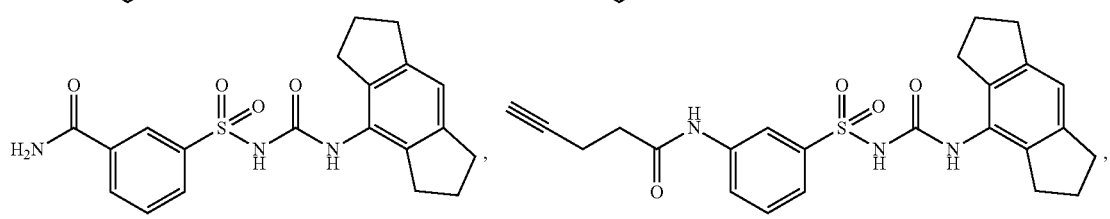
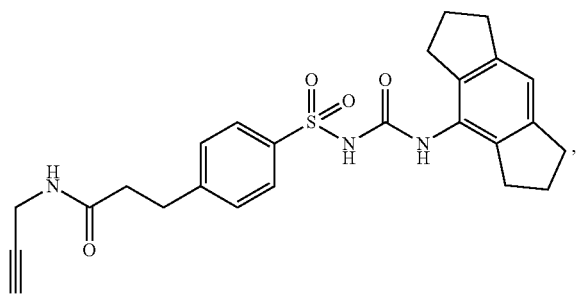

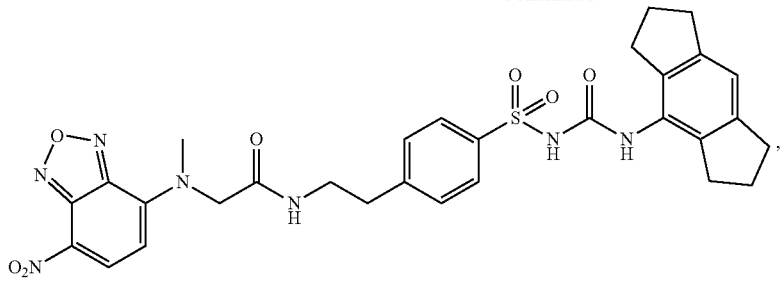
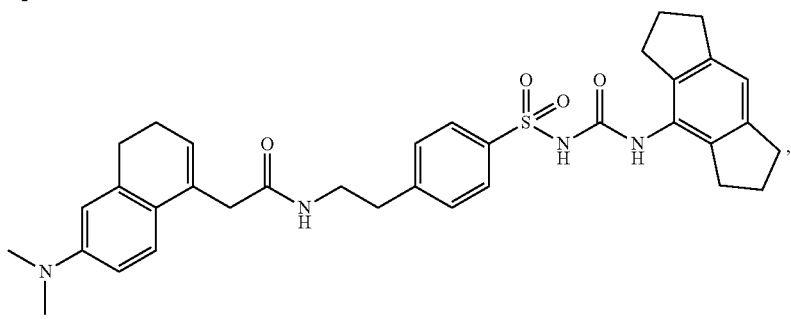
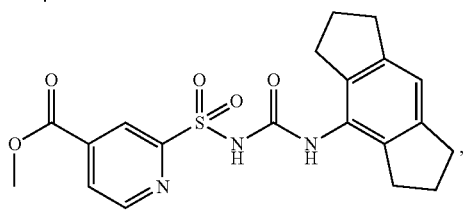
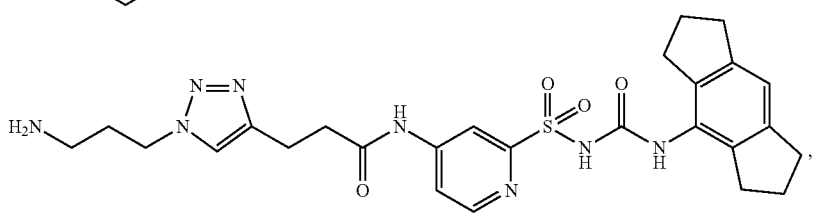
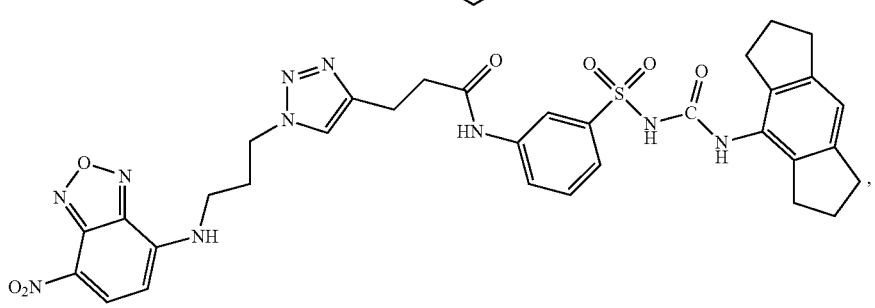
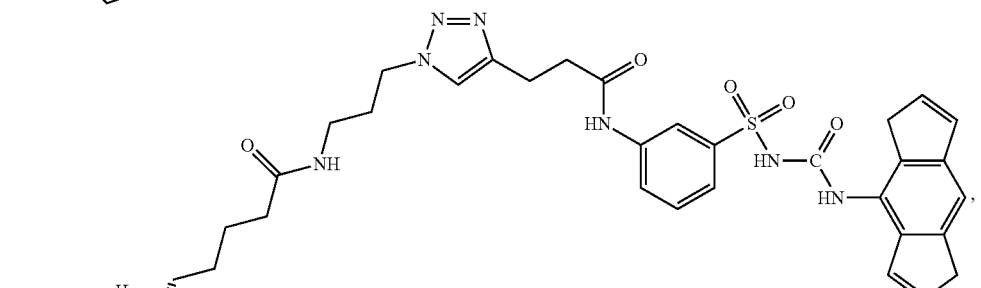
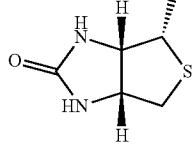

-continued
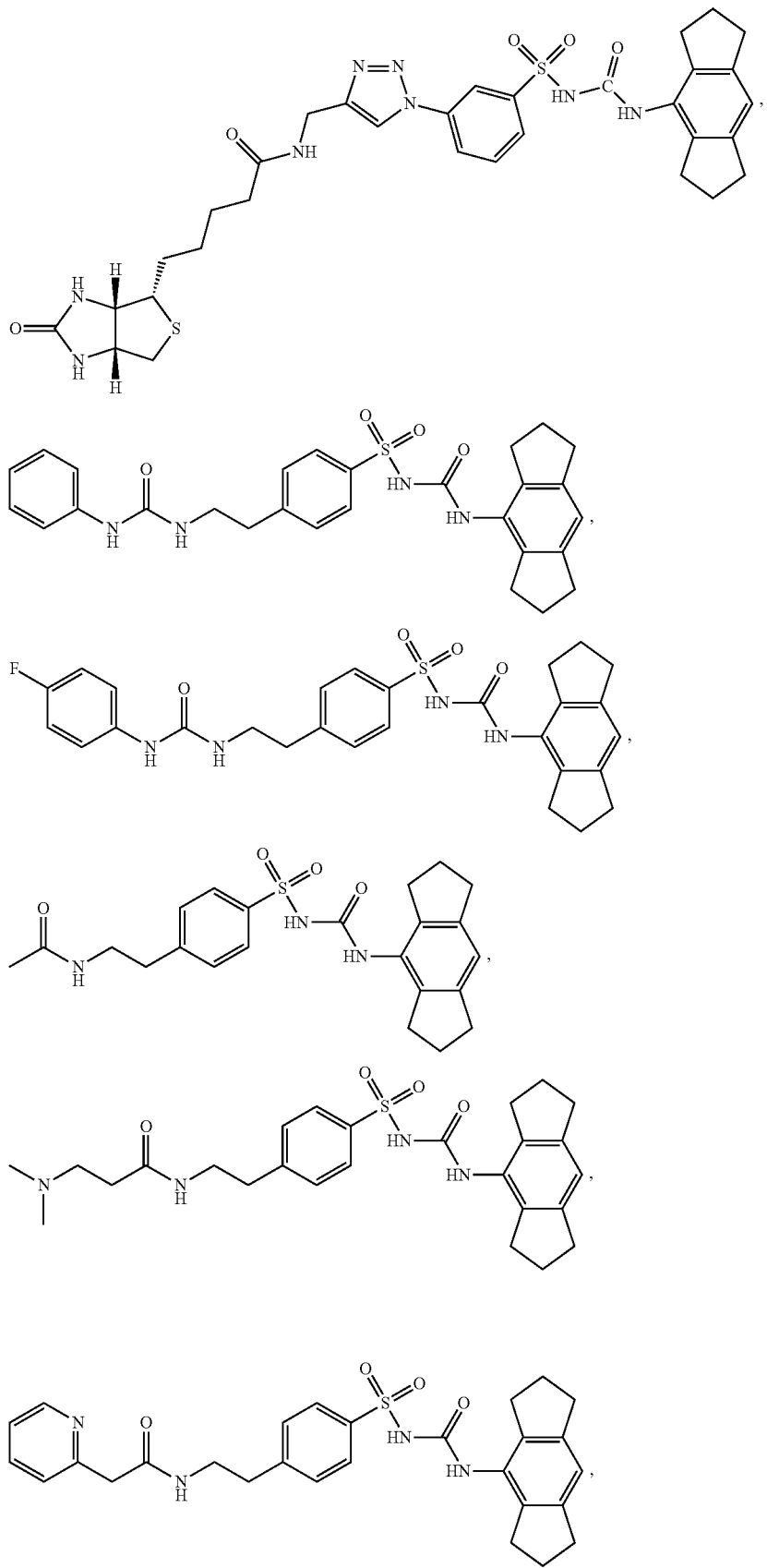

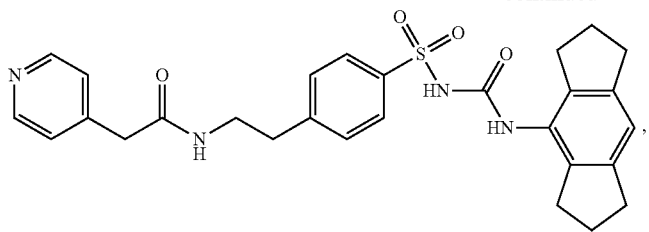,
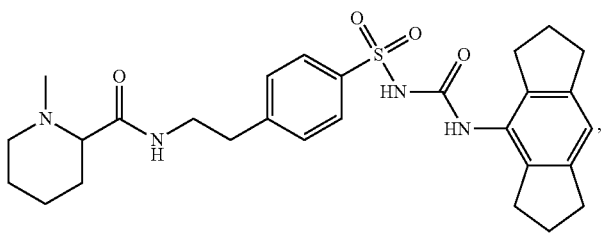,
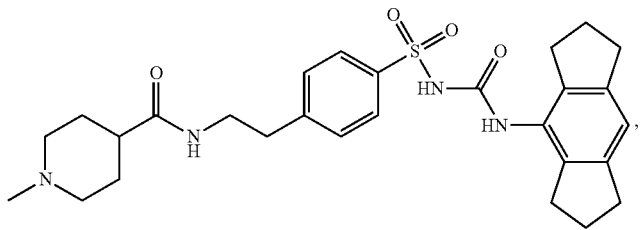,
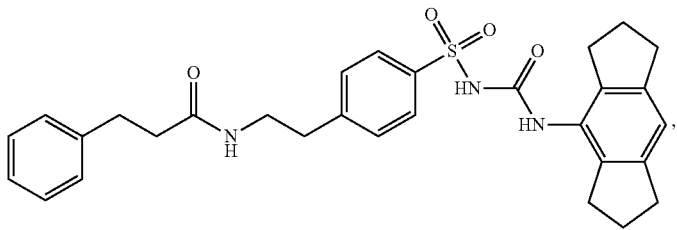,
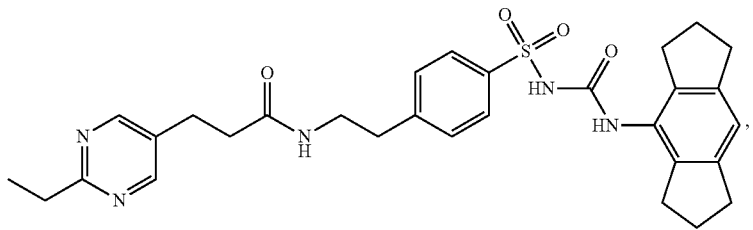,
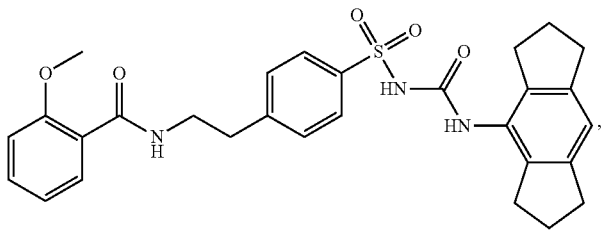,
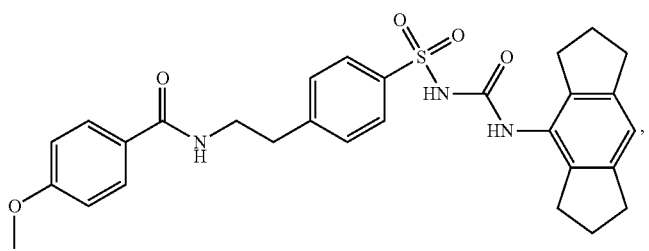, -continued
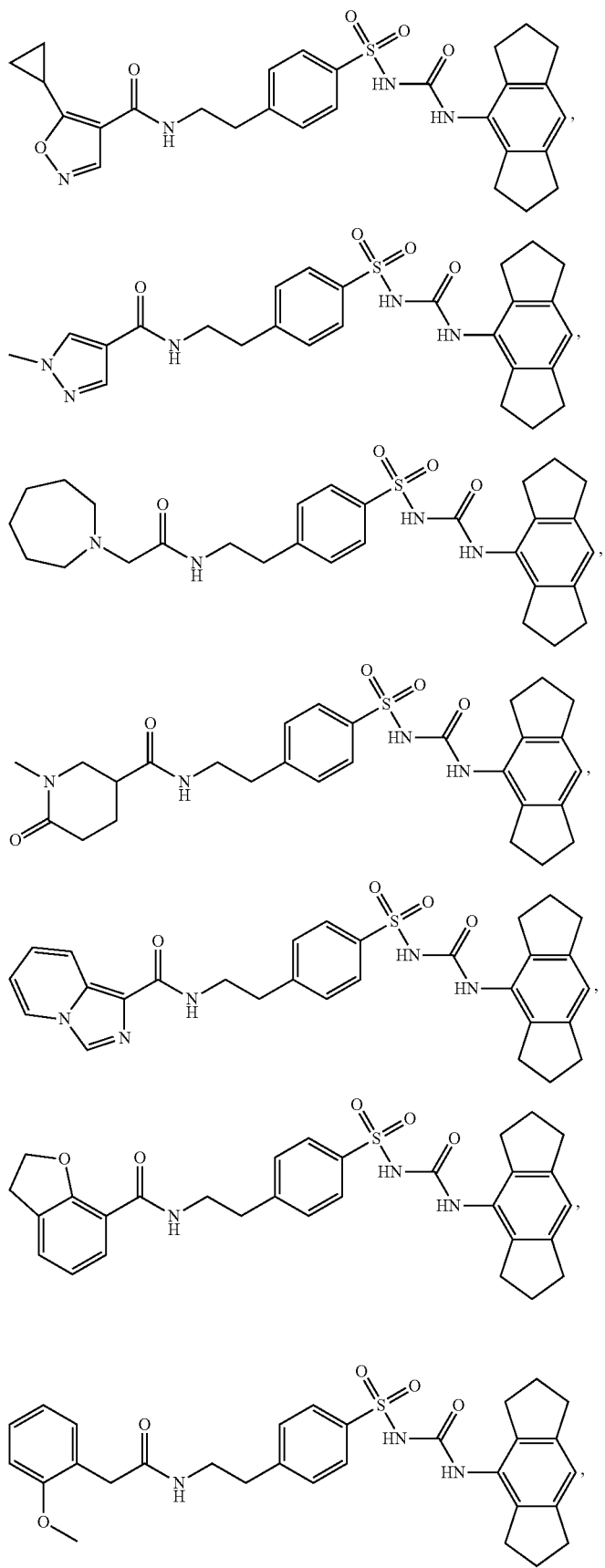

-continued
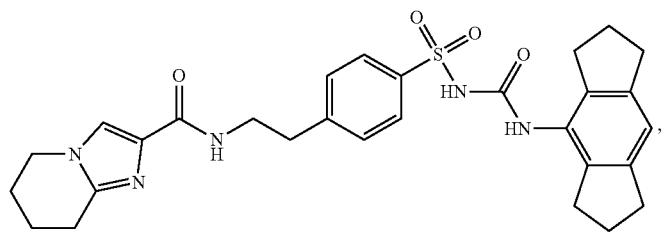
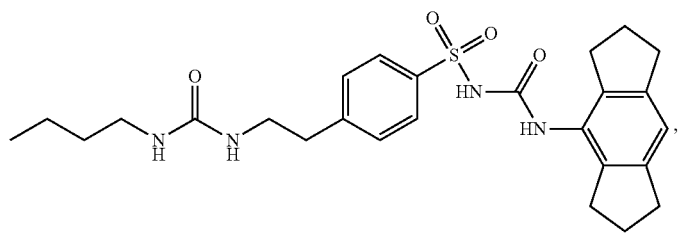
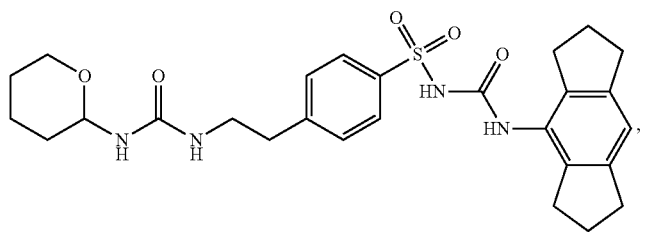
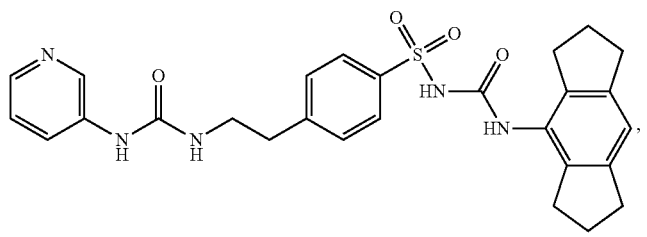
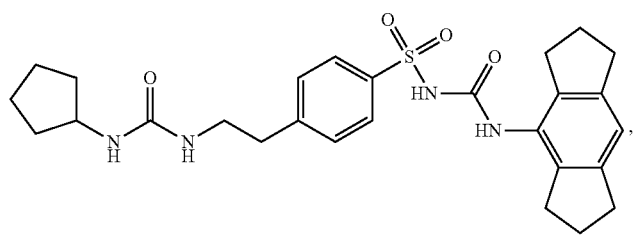
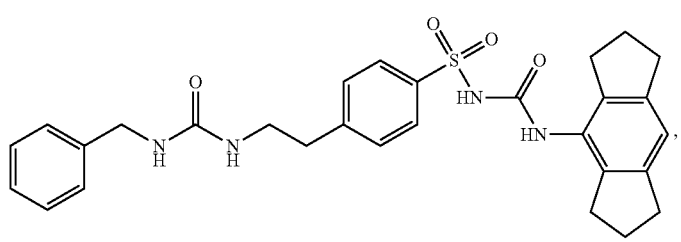
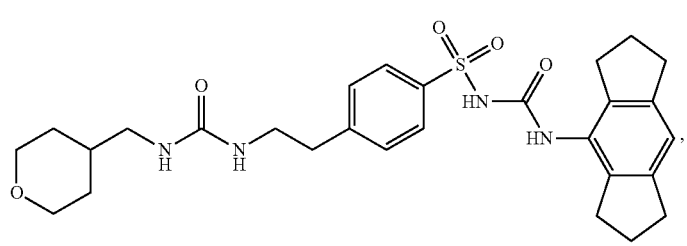

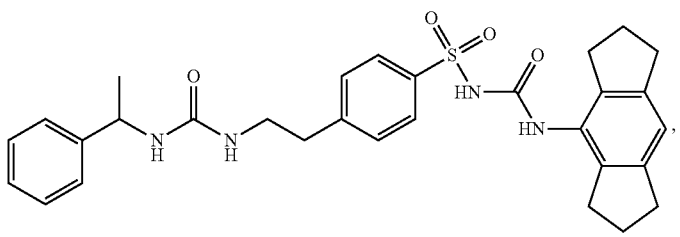,
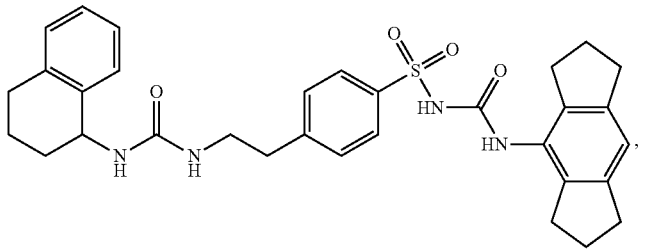,
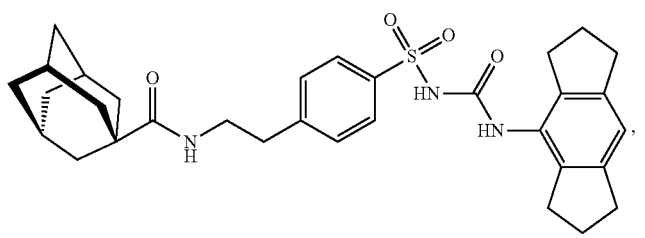,
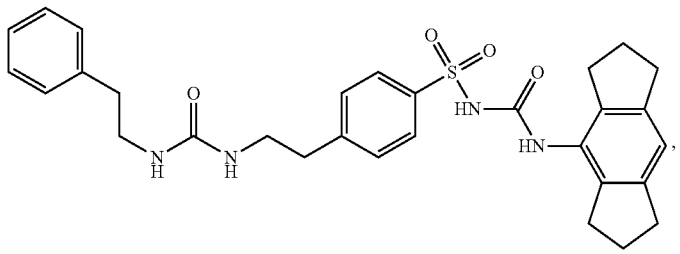,
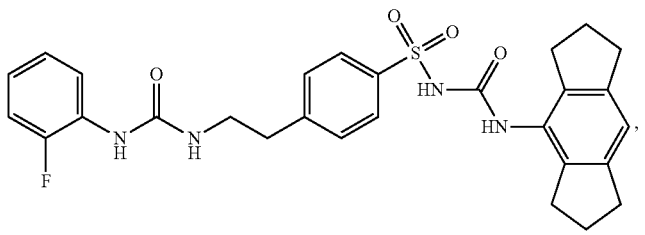,
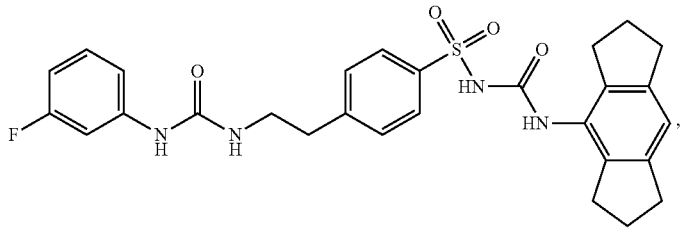,
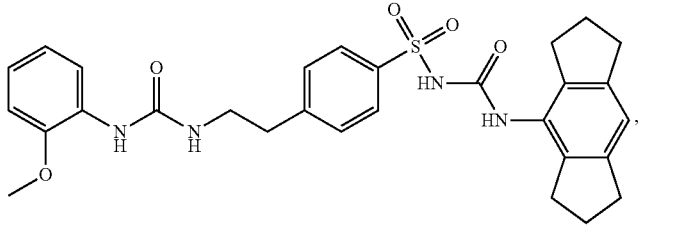, -continued
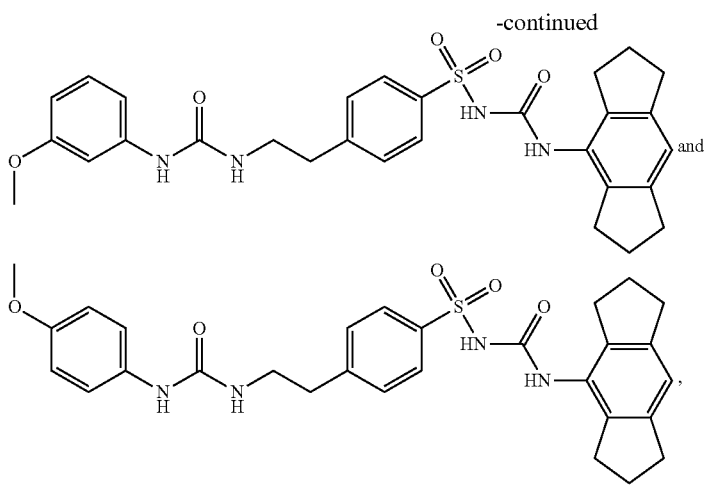
20
or (b) a pharmaceutically acceptable salt or solvate thereof.
8. A pharmaceutical composition comprising the compound or the pharmaceutically acceptable salt or solvate of claim 1, and a pharmaceutically acceptable excipient.
9. A prodrug of the compound as claimed in claim 1, or a pharmaceutically acceptable salt or solvate thereof.
* * * * *